US008404728B2

(12) United States Patent
Pang et al.

(10) Patent No.: US 8,404,728 B2
(45) Date of Patent: Mar. 26, 2013

(54) SMALL-MOLECULE BOTULINUM TOXIN INHIBITORS

(75) Inventors: Yuan-Ping Pang, Rochester, MN (US); Jewn Giew Park, Rochester, MN (US); Shaohua Wang, Rochester, MN (US); Anuradha Vummenthala, Iowa City, IA (US); Rajesh K Mishra, Iowa City, IA (US); Jon Davis, Silver Spring, MD (US); Charles B. Millard, Frederick, MD (US); James J. Schmidt, Mt. Airy, MD (US)

(73) Assignees: Mayo Foundation for Medical Education and Research, Rochester, MN (US); U.S. Army Medical Research and Material Command, Washington, DC (US)

( * ) Notice: Subject to any disclaimer, the term of this patent is extended or adjusted under 35 U.S.C. 154(b) by 224 days.

(21) Appl. No.: 12/846,187

(22) Filed: Jul. 29, 2010

(65) Prior Publication Data

US 2012/0114696 A1 May 10, 2012

Related U.S. Application Data

(60) Provisional application No. 61/229,827, filed on Jul. 30, 2009.

(51) Int. Cl.

| | |
|---|---|
| *A01N 43/78* | (2006.01) |
| *A01N 43/80* | (2006.01) |
| *A01N 43/76* | (2006.01) |
| *A01N 43/50* | (2006.01) |
| *A01N 43/56* | (2006.01) |
| *A61K 31/425* | (2006.01) |
| *A61K 31/42* | (2006.01) |
| *A61K 31/415* | (2006.01) |
| *C07D 271/00* | (2006.01) |
| *C07D 285/02* | (2006.01) |
| *C07D 285/04* | (2006.01) |
| *C07D 417/00* | (2006.01) |
| *C07D 513/00* | (2006.01) |
| *C07D 277/20* | (2006.01) |
| *C07D 275/02* | (2006.01) |
| *C07D 263/30* | (2006.01) |
| *C07D 413/00* | (2006.01) |
| *C07D 261/06* | (2006.01) |
| *C07D 257/04* | (2006.01) |
| *C07D 257/10* | (2006.01) |
| *C07D 403/00* | (2006.01) |
| *C07D 487/00* | (2006.01) |
| *C07D 249/04* | (2006.01) |
| *C07D 249/08* | (2006.01) |
| *C07D 233/61* | (2006.01) |
| *C07D 231/00* | (2006.01) |
| *C07D 207/00* | (2006.01) |

(52) U.S. Cl. ........ 514/365; 514/372; 514/374; 514/378; 514/396; 514/403; 548/125; 548/202; 548/214; 548/235; 548/254; 548/255; 548/267.2; 548/335.5; 548/375.1; 548/566; 548/247

(58) Field of Classification Search ................. 514/365, 514/372, 374, 378, 396, 403; 548/125, 202, 548/214, 235, 247, 254, 255, 267.2, 335.5, 548/375.1, 566

See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,710,795 | A | 1/1973 | Higuchi et al. |
| 3,845,770 | A | 11/1974 | Theeuwes et al. |
| 3,916,899 | A | 11/1975 | Theeuwes et al. |
| RE28,819 | E | 5/1976 | Thompson |
| 4,008,719 | A | 2/1977 | Theeuwes et al. |
| 4,044,126 | A | 8/1977 | Cook et al. |
| 4,328,245 | A | 5/1982 | Yu et al. |
| 4,358,603 | A | 11/1982 | Yu |
| 4,364,923 | A | 12/1982 | Cook et al. |
| 4,409,239 | A | 10/1983 | Yu |
| 4,410,545 | A | 10/1983 | Yu et al. |
| 4,414,209 | A | 11/1983 | Cook et al. |
| 4,522,811 | A | 6/1985 | Eppstein et al. |
| 4,710,384 | A | 12/1987 | Rotman |
| 5,033,252 | A | 7/1991 | Carter |
| 5,052,558 | A | 10/1991 | Carter |
| 5,059,595 | A | 10/1991 | Le Grazie |
| 5,073,543 | A | 12/1991 | Marshall et al. |
| 5,120,548 | A | 6/1992 | McClelland et al. |
| 5,323,907 | A | 6/1994 | Kalvelage |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,709,874 | A | 1/1998 | Hanson et al. |
| 5,733,566 | A | 3/1998 | Lewis |
| 5,759,542 | A | 6/1998 | Gurewich |
| 5,840,674 | A | 11/1998 | Yatvin et al. |

(Continued)

FOREIGN PATENT DOCUMENTS

WO WO 2008051197 A2 * 5/2008

OTHER PUBLICATIONS

Ansel, *Introduction to Pharmaceutical Dosage Forms—Fourth Edition* (Philadelphia, Lea & Febiger, 1985), p. 126.

(Continued)

*Primary Examiner* — Sreeni Padmanabhan
*Assistant Examiner* — Sarah Pihonak
(74) *Attorney, Agent, or Firm* — Fish & Richardson P.C.

(57) ABSTRACT

This disclosure relates to materials and methods for inhibiting Botulinum neurotoxin, and more particularly to materials and methods for inhibiting the zinc endopeptidase of Botulinum neurotoxin serotypes A, D and/or E (BoNTA, BoNTD and/or BoNTE).

18 Claims, 17 Drawing Sheets

U.S. PATENT DOCUMENTS

| | | | |
|---|---|---|---|
| 5,860,957 | A | 1/1999 | Jacobsen et al. |
| 5,900,252 | A | 5/1999 | Calanchi et al. |
| 5,948,433 | A | 9/1999 | Burton et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |

OTHER PUBLICATIONS

Berendsen et al., "Molecular dynamics with coupling to an external bath," *J Chem Phys.*, 1984, 81:3684-3690.

Darden et al., "Particle Mesh Ewald-an N.Log(N) method for Ewald sums in large systems," *J Chem Phys.*, 1993, 98:10089-10092.

Ekstrom et al., "Structure of HI-6*sarin-acetylcholinesterase determined by X-ray crystallography and molecular dynamics simulation: reactivator mechanism and design," *PLoS One*, 2009, 4(6):e5957, 19 pages.

Hornak et al., "Comparison of multiple Amber force fields and development of improved protein backbone parameters," *Proteins*, 2006, 65:712-725.

IUPAC-IUB Commission on Biochemical Nomenclature: Abbreviated Nomenclature of Synthetic Polypeptides (Polymerized Amino Acids), *Biochem.*, 1972, 11(5):942-944.

Jorgensen et al., "Comparison of simple potential functions for simulating liquid water," *J Chem Phys.*, 1983, 79:926-935.

Nishibata et al., "Confirmation of usefulness of a structure construction program based on three-dimensional receptor structure for rational lead generation," *J. Med. Chem.*, 1993, 36(20):2921-2928.

Nogrady, *Medicinal Chemistry A Biochemical Approach* (New York, Oxford University Press, 1985), pp. 388-392.

Oelschlaeger et al., "Modeling Domino Effects in Enzymes: Molecular Basis of the Substrate Specificity of the Bacterial Metallo-β-lactamases IMP-1 and IMP-6," *J. Biochemistry*, 2003,42:8945-8956.

Oelschlaeger et al., "Insight into the mechanism of the IMP-1 metallo-beta-lactamase by molecular dynamics simulations," *J. Protein Eng.*, 2003, 16:341-350.

Pang et al., "Computational and Experimental Studies of (2,2)-Bis(indo1-1-yl-methyl)acetate Suggest the Importance of the Hydrophobic Effect in Aromatic Stacking Interactions," *J. Am. Chem. Soc.*, 1999, 121:1717-1725.

Pang, "Novel zinc protein molecular dynamics simulations: Steps toward antiangiogenesis for cancer treatment," *J. Mol. Model.*, 1999, 5:196-202.

Pang, "Three-dimensional model of a substrate-bound SARS chymotrypsin-like cysteine proteinase predicted by multiple molecular dynamics simulations: catalytic efficiency regulated by substrate binding," *Proteins*, 2004:57:747-757.

Pang, "Successful molecular dynamics simulation of two zinc complexes bridged by a hydroxide in phosphotriesterase using the cationic dummy atom method," *Proteins*, 2001, 45(3):183-189.

Pang et al., "Successful molecular dynamics simulation of the zinc-bound farnesyltransferase using the cationic dummy atom approach," *Protein Sci.*, 2000, 9(10):1857-1865.

Park et al., "Serotype-selective, small-molecule inhibitors of the zinc endopeptidase of botulinum neurotoxin serotype A," *Bioorg Med Chem.*, 2006, 14:395-408.

Pearlman et al., "AMBER, a package of computer programs for applying molecular mechanics, normal mode analysis, molecular dynamics and free energy calculations to simulate the structural and energetic properties of molecules," *Comput Phys Commun.*, 1995, 91:1-41.

Schmidt and Stafford, "Fluorigenic substrates for the protease activities of botulinum neurotoxins serotypes A, B, and F," *Appl Environ Microbiol.*, 2003, 69:297-303.

Schmidt and Bostian, "Endoproteinase activity of type A botulinum neurotoxin: substrate requirements and activation by serum albumin," *J. Protein Chem.*, 1997, 16:19-26.

Segel, *Enzyme Kinetics* (New York, Wiley and Sons, 1975), pp. 170-178.

Shao et al., "Clustering molecular dynamics trajectories: I. Characterizing the performance of different clustering algorithms," *J Chem Theory Comput.*, 2007, 3:2312-2334.

Silvaggi et al., "Catalytic Features of the Botulinum Neurotoxin A Light Chain Revealed by High Resolution Structure of an Inhibitory Peptide Complex," *Biochemistry*, 2008, 47:5736-5745.

Tang et al., "Computer-aided lead optimization: improved small-molecule inhibitor of the zinc endopeptidase of botulinum neurotoxin serotype a," *PLoS One*, 2007, 8:e761, 8 pages.

* cited by examiner 1 2 3 4 5 6 7

E2 a. 12 N HCl/MeOH, reflux; b. NBS/THF, reflux; c. 4-iodo-3-nitrobenzoyl chloride/$AlCl_3$/$CH_2Cl_2$, rt; d. PhCCH/$Pd(PPh_3)_2Cl_2$/$K_2CO_3$/$Et_3N$/DMF, rt; e. $SnCl_2$•$2H_2O$/EtOAc, reflux; f. $InBr_3$/toluene, reflux; g. 1-(N-Phth)amino-4-bromobutane, CsF-Celite/$CH_3CN$, reflux; h. 1-fluoropyridinium triflate/DCM, rt, i.(4-OH)$C_6H_4B(OH)_2$, $Pd(PPh_3)_4$/CsF/DME, reflux; j. 50% $NH_2OH$:THF:MeOH = 0.7:1:3, rt.

E3 a. NBS/THF, 0 °C; b. 4-iodo-3-nitrobenzoyl chloride/$AlCl_3$/$CH_2Cl_2$, rt; c. PhCCH/$Pd(PPh_3)_2Cl_2$/$K_2CO_3$/$Et_3N$/DMF, rt; d. $SnCl_2 \bullet 2H_2O$/EtOAc, reflux; e. $InBr_3$/toluene, reflux; f. 1-(N-Phth)amino-4-bromobutane, CsF/$CH_3CN$, reflux; g. 1-fluoropyridinium triflate/DCM, rt; h. $(3\text{-}NH_2)C_6H_4B(OH)_2$, $Pd(PPh_3)_4$/CsF/DME, reflux; i. 50% aq $NH_2OH$:THF:MeOH = 0.7:1:3, rt.

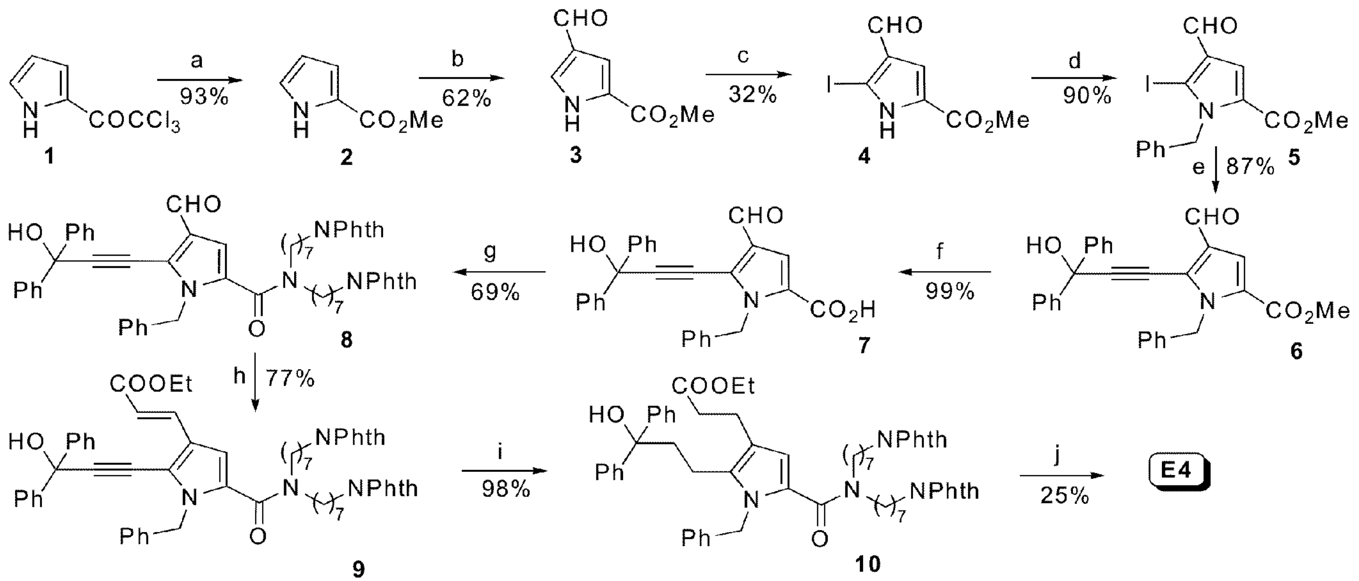

a. $K_2CO_3$/MeOH, reflux, 3 h; b. $CH_3OCHCl_2/AlCl_3$/DCM/$CH_3NO_2$, -40 °C to rt, 16 h; c. $CF_3CO_2Ag/I_2/CHCl_3$/0 °C to rt, 20 h; d. $K_2CO_3$/BnBr/Acetone, reflux, 16 h; e. 1,1-diphenylprop-2-yn-1-ol/Pd$(PPh_3)_2Cl_2$/CuI/$PPh_3/Et_3N$/DMF, 70 °C, 16 h; f. MeOH/$H_2O$/KOH, 60 °C, 2 h; g. 14/BOP/HOBt/NMM/DMF, rt, 16 h; h. $Ph_3P$=CHCOOEt/Benzene, reflux, 16 h; i. $H_2$/Pd-C/EtOAc, rt, 48 h; j. 50% aq.$NH_2OH$/KCN/MeOH/THF, 35 °C, 24 h.

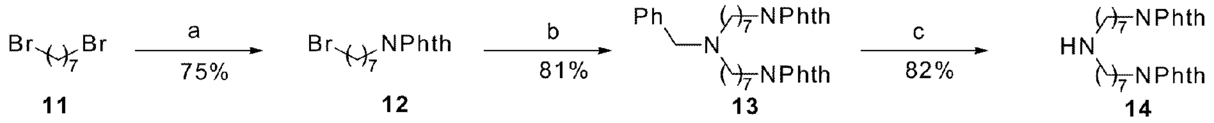

a. KNPhth/acetone, reflux, 16 h; b. $K_2CO_3/BnNH_2$/acetone, reflux, 48 h; c. $H_2$/Pd-C/MeOH, EtOAc, rt, 16 h;

FIG. 4

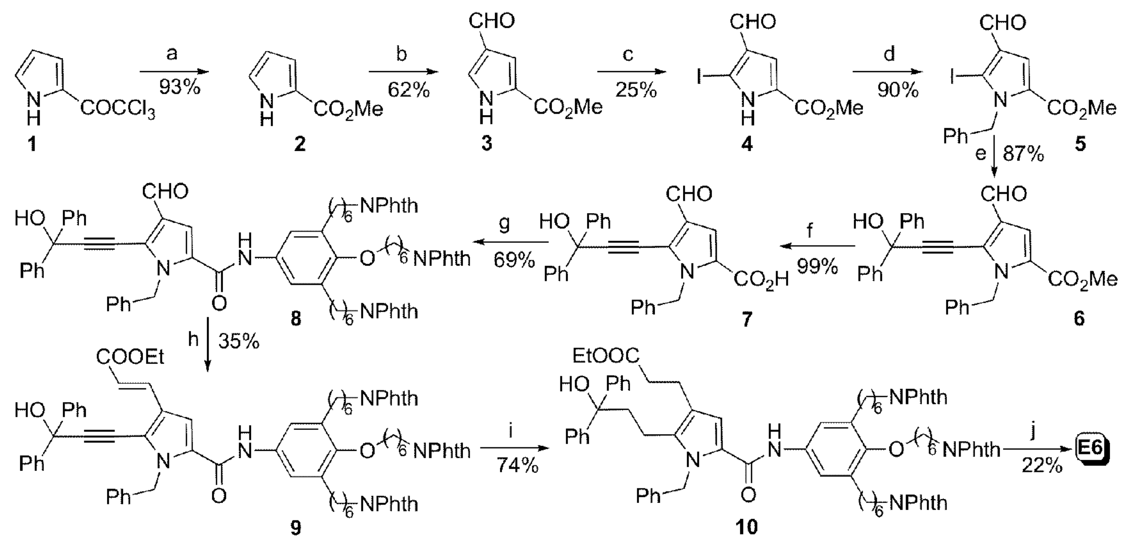

a. $K_2CO_3$/MeOH, reflux, 3 h; b. $CH_3OCHCl_2/AlCl_3/CH_2Cl_2/CH_3NO_2$, -40 °C to rt, 16 h; c. $CF_3COOAg/I_2/CHCl_3$/ 0 °C to rt, 20 h; d. $K_2CO_3$/BnBr/Acetone, reflux, 16 h; e. 1,1-diphenylprop-2-yn-1-ol/$Pd(PPh_3)_2Cl_2$/CuI/$PPh_3/Et_3N$/DMF, 70 °C, 16 h; f. MeOH/$H_2O$/KOH, 60 °C, 2 h; g. 14/BOP/HOBt/NMM/DMF, rt, 16 h; h. $PPh_3$=CHCOOEt/Benzene, reflux, 16 h; i. $H_2$/Pd-C/EtOAc, rt, 48 h; j. 50% aq.$NH_2OH$/KCN/MeOH/THF, 35 °C, 24 h;

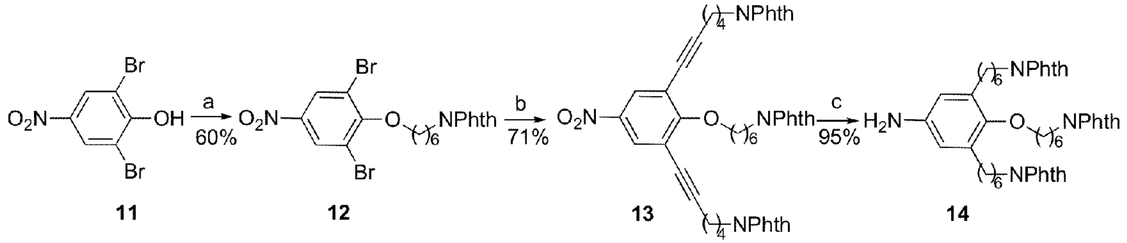

a.$K_2CO_3$/6-bromo hexylphthalimide/acetonitrile, reflux, 72 h; b.2-(hex-5-ynyl)isoindoline-1,3-dione/$Pd(PPh_3)_2Cl_2$/CuI/DMF, 80 °C, 16 h; c.$H_2$/Pd-C/EtOAc, rt, 12 h;

FIG. 6

Dixon plots

| | 1/v | | |
|---|---|---|---|
| AV42 (uM) | 1st | 2nd | 3rd |
| 4.00 | 0.830988 | 0.595863 | 0.801487 |
| 2.86 | 0.617177 | 0.477833 | 0.588132 |
| 2.04 | 0.493817 | 0.368434 | 0.454454 |
| 1.46 | 0.412335 | 0.307081 | 0.351649 |
| 1.04 | 0.353877 | 0.270789 | 0.281783 |
| 0.74 | 0.309046 | 0.233755 | 0.243175 |
| 0.53 | 0.267025 | 0.202024 | 0.201677 |
| 0.38 | 0.249122 | 0.184759 | 0.190903 |
| 0.27 | 0.218375 | 0.169311 | 0.160958 |

Ki = Km/[slope]x[substrate concentration]xVmax

Ki AV42 = 0.76 +/- 0.17 uM

Fractional inhibition (F)

Ki = [I]-(F)[I]/(F)(1+S/Km)

Ki AV42 = 0.71 +/- 0.045 uM

Cheng and Prusoff

Ki = IC50/1+S/Km

Ki AV42 = 0.71 +/- 0.035 uM

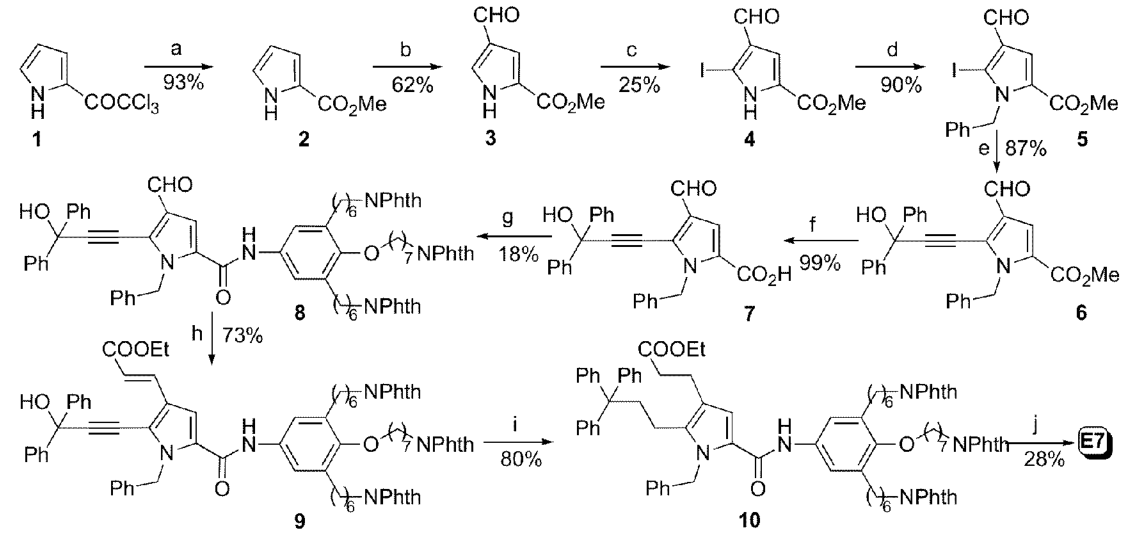

1 2 3 4 5 6 7 8 9 10 a. $K_2CO_3$/MeOH, reflux, 3 h; b. $CH_3OCHCl_2/AlCl_3/DCM/CH_3NO_2$, -40 °C to rt, 16 h; c. $CF_3COOAg/I_2/CHCl_3$/ 0 °C to rt, 20 h; d. $K_2CO_3$/BnBr/Acetone, reflux, 16 h; e. 1,1-diphenylprop-2-yn-1-ol/Pd($PPh_3$)$_2Cl_2$/CuI/$PPh_3$/$Et_3N$/DMF, 70 °C, 16 h; f. MeOH/$H_2O$/KOH, 60 °C, 2 h; g. 14/BOP/HOBt/NMM/DMF, rt, 16 h; h. $PPh_3$=CHCOOEt/Benzene, reflux, 16 h; i. $H_2$/Pd-C/EtOAc, rt, 48 h; j. 50% aq.$NH_2OH$/KCN/MeOH/THF, 35 °C, 24 h;

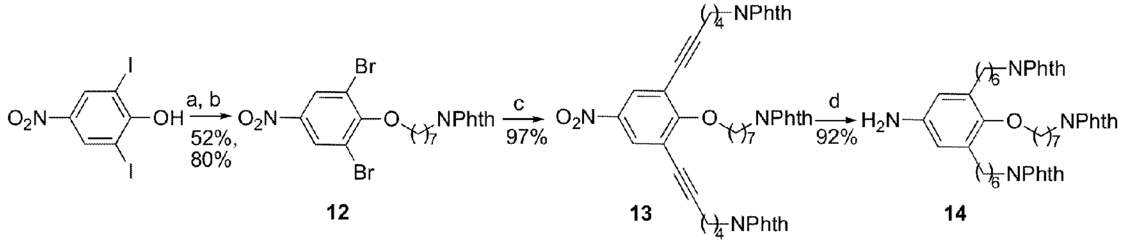

12 13 14 a.$K_2CO_3$/1,7-dibromoheptane/acetonitrilereflux, 36 h; b. potassium phthalimide, acetone, reflux, 24 h; c.2-(hex-5-ynyl)isoindoline-1,3-dione/Pd($OAc)_2$/$Cs_2CO_3$/DMF, rt, 2 h; d.$H_2$/Pd-C/EtOAc, rt, 12 h;

FIG. 15

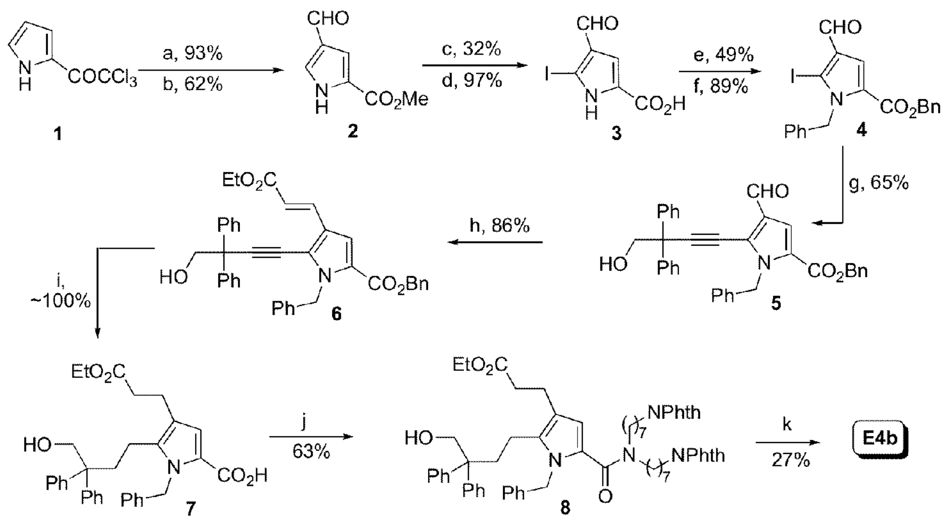

a. $MeOH/K_2CO_3$, 3 h; b. $CH_3OCHCl_2/AlCl_3/DCM/CH_3NO_2$, -40 °C; c. $CF_3CO_2Ag/I_2/CHCl_3$, 0 °C to rt, 20 h; d. $KOH/MeOH/H_2O$, 60 °C; e. BnOH/BOP/HOBt/NMM/DMF, rt, 24 h; f. $BnBr/K_2CO_3$/DMF, rt, 12 h; g. 2,2-diphenylbut-3-yn-1-ol (10)/$Pd(PPh_3)_2Cl_2$/CuI/$PPh_3$/$Et_3N$/DMF, 65 °C, 17 h; h. $Ph_3P=CHCO_2Et$/benzene, 80 °C, 16 h; i. $H_2/Pd(OH)_2$-C, EtOAc/MeOH (1:1); j. 14/BOP/NMM/DMF, rt, 19 h; k. 50% aq. $NH_2OH$/KCN/MeOH/THF, 65 °C, 48 h.

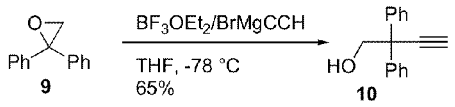

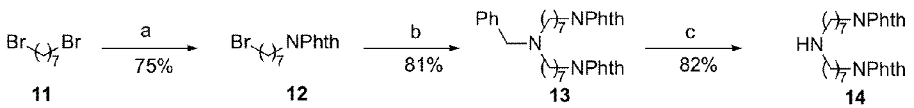

a. KNPhth/acetone, reflux, 16 h; b. $K_2CO_3/BnNH_2$/acetone, reflux, 48 h; c. $H_2$/Pd-C/MeOH, EtOAc, rt, 16 h;

FIG. 17

SMALL-MOLECULE BOTULINUM TOXIN INHIBITORS

CROSS-REFERENCE TO RELATED APPLICATIONS

This application claims priority under 35 U.S.C. §119(e) to U.S. Application Ser. No. 61/229,827, filed on Jul. 30, 2009.

STATEMENT AS TO FEDERALLY FUNDED RESEARCH

Studies described herein were supported by the U.S. Army Medical Research Acquisition Activity (W81XWH-04-2-0001) and (W81XWH-08-1-0154), the U.S. Army Research Office (W911NF-09-1-0095), and the U.S. Defense Threat Reduction Agency (3.10023_07_RD_B and 3.10014_08_WR_B). The Government has certain rights in this invention.

TECHNICAL FIELD

This disclosure relates to materials and methods for inhibiting Botulinum neurotoxin, and more particularly to materials and methods for inhibiting the zinc endopeptidase of Botulinum neurotoxin serotypes A, D and/or E (BoNTA, BoNTD and/or BoNTE).

BACKGROUND

Botulinum neurotoxin serotype A (BoNTA) is a highly toxic by-product of a naturally occurring, spore-forming anaerobic bacterium (*Clostridium botulinum*). BoNTA inhibits the release of acetylcholine from presynaptic nerve terminals at neuromuscular junctions, causing flaccid paralysis and leading to death by respiratory arrest. BoNTA also can be used in the treatment of various muscular dysfunctions and has been widely used as a cosmetic known as BOTOX® to diminish facial lines. BoNTA, however, is fatal when misused, and there are currently no chemical antidotes to BoNTA.

The crystal structure of holo BoNTA includes two polypeptide chains that are linked by a disulfide bond. The light chain (50 KDa) is a zinc endopeptidase that specifically cleaves neuronal proteins responsible for acetylcholine release. The heavy chain (100 KDa) mediates selective binding to neuronal cells via specific gangliosides and translocates the light chain into the cytosol after receptor-mediated endocytosis of the entire molecule. Of eight serotypes of BoNT, serotypes A, D and E are closely related, according to sequence analysis using ClustalW.

SUMMARY

This disclosure provides materials and methods for inhibiting Botulinum neurotoxin, including BoNTA, BoNTD, and/or BoNTE. For example, small-molecule inhibitors of BoNTA are provided. A small-molecule inhibitor can inhibit the zinc protease, an endopeptidase, of BoNTA, BoNTD, and/or BoNTE. In some cases, a small-molecule inhibitor can inhibit the zinc protease of BoNTA. Methods for using such small-molecule inhibitors to treat, prevent, or ameliorate one or more symptoms of Botulinum poisoning or disorders associated with Botulinum poisoning, including food-borne botulism, infant botulism, wound botulism, adult enteric infectious botulism, and inhalation botulism, and BoNTA, BoNTD, and/or BoNTE poisoning, are also provided. Kits and articles of manufacture containing one or more small-molecule inhibitors and accessory items are also provided.

Provided herein is a composition having a compound of Formula (I-A):

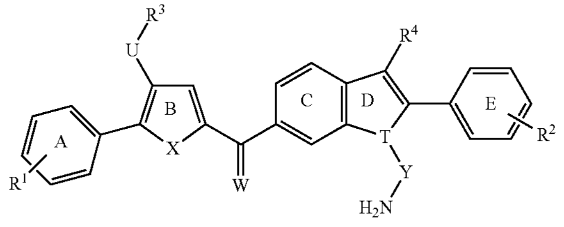

or a pharmaceutically acceptable salt or derivative thereof, wherein:

$R^1$ is chosen from OH and $NH_2$;

$R^2$ is chosen from H, OH, halo, $C_{1-10}$ alkyl, $C_{2-10}$ alkenyl, $C_{2-10}$ alkynyl, $C_{1-10}$ alkoxy, cycloalkyl, aryl, heteroaryl, $CONH_2$, and $CONR^{2a}R^{2b}$;

$R^{2a}$ and $R^{2b}$ are independently chosen from $(CH_2)_{m3}NH_2$;

m3 is an integer from 4 to 12;

$R^3$ is chosen from thiol, imidazole, sulfonamide, COOH, and CONHOH;

$R^4$ is chosen from H, F, Cl, and Br;

X is chosen from S, NH, and O;

T is chosen from C and N;

U is chosen from $(CH_2)_{m1}V(CH_2)_{m2}$;

V is chosen from C, C(OH), O, S, and NH, or is absent;

m1 is an integer from 0 to 3;

m2 is an integer from 0 to 3;

W is chosen from O and S;

Y is chosen from $CO(CH_2)_{m4}$, $(CH_2)_{m4}$, and $CONH(CH_2)_{m4}$;

m4 is an integer from 2 to 8;

all non-hydrogen atoms in rings A-E can be substituted by N, S, or O provided the substitution maintains aromaticity; and wherein if $R^4$ is H then $R^2$ is not H.

In some embodiments, a compound of Formula (I-A) is chosen from:

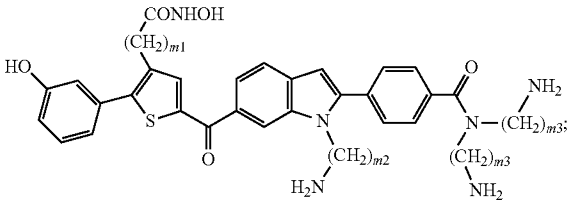

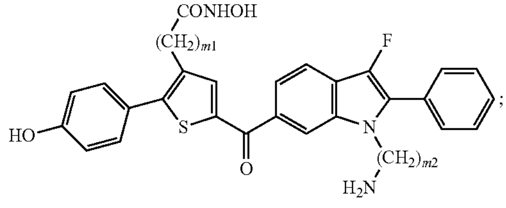

; and

-continued

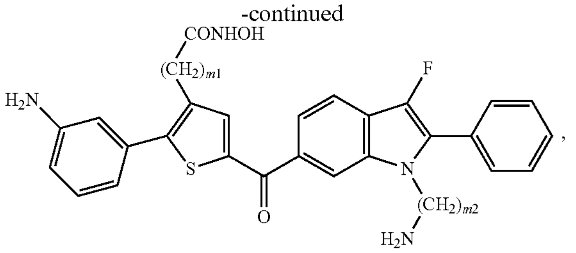

or a pharmaceutically acceptable salt or derivative thereof, wherein:

m1 is an integer from 1 to 2;

m2 is an integer from 3 to 8; and m3 is an integer from 6 to 12.

Exemplary compounds according to Formula (I-A) include:

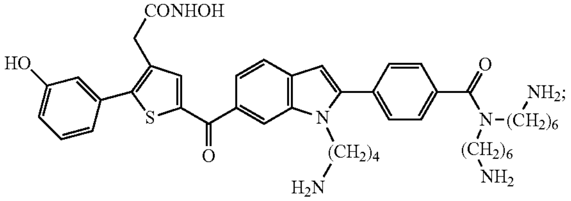

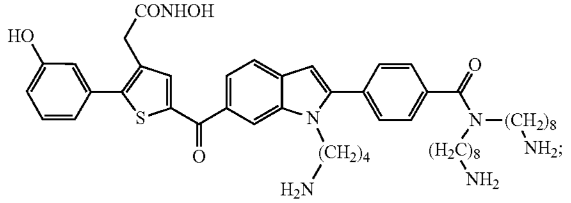

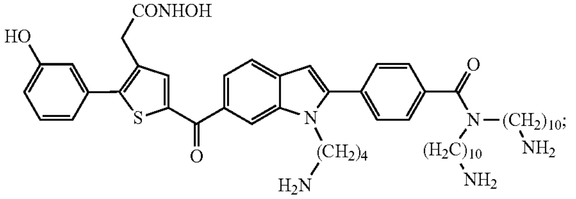

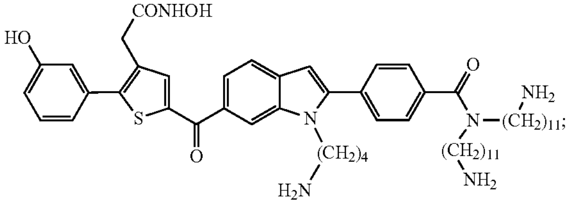

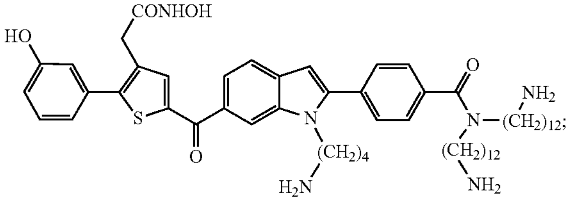

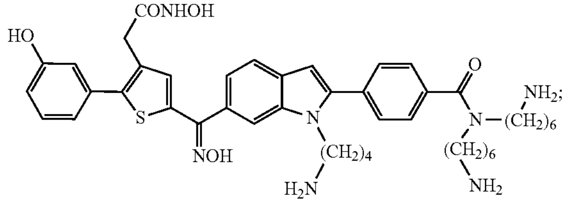

-continued

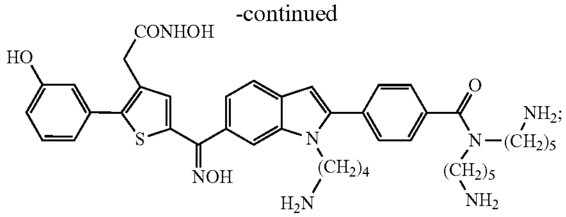

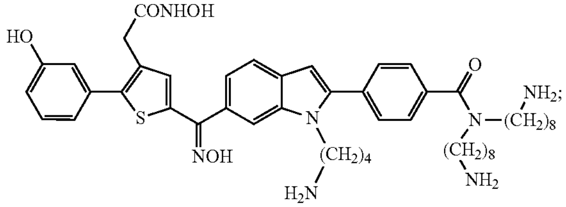

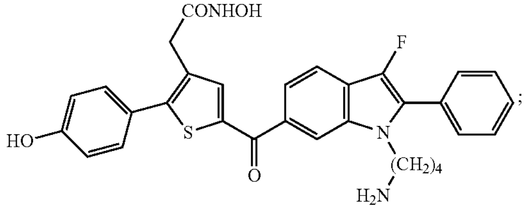

and

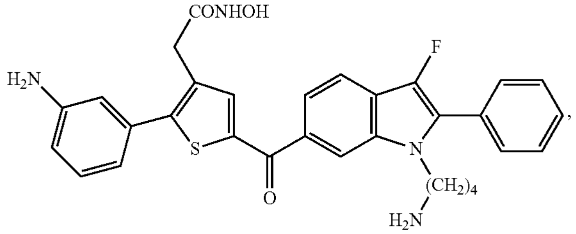

or a pharmaceutically acceptable salt or derivative thereof.

Further provided herein is a composition having a compound of Formula (II-A):

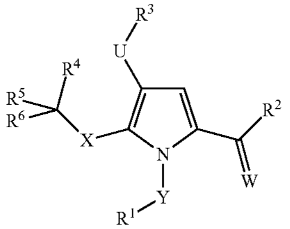

or a pharmaceutically acceptable salt or derivative thereof, wherein:

$R^1$ is chosen from $NH_2$, aryl, and heteroaryl;

$R^2$ is chosen from $NR^{2a}R^{2b}$;

$R^{2a}$ and $R^{2b}$ are chosen from $(CH_2)_mNH_2$;

m is an integer from 4 to 12;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $NH_2$, aryl and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

W is chosen from O and S, or is absent;

Y is chosen from $CO(CH_2)_{m3}$, $(CH_2)_{m3}$, and $CONH(CH_2)_{m3}$;

m3 is an integer from 1 to 10; and all non-hydrogen atoms in the pyrrole ring can be substituted by N, S, or O provided the substitution maintain aromaticity.

In some embodiments, a compound of Formula (II-A) is chosen from:
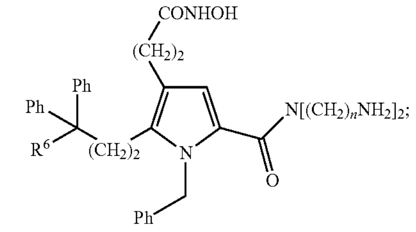
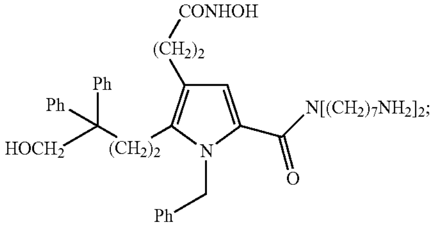
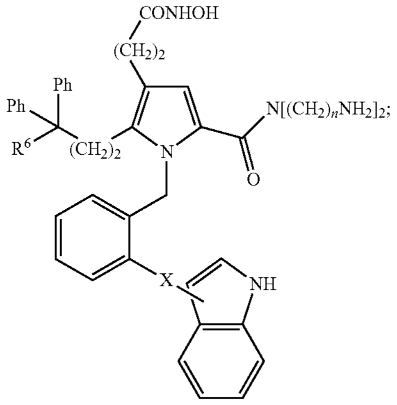
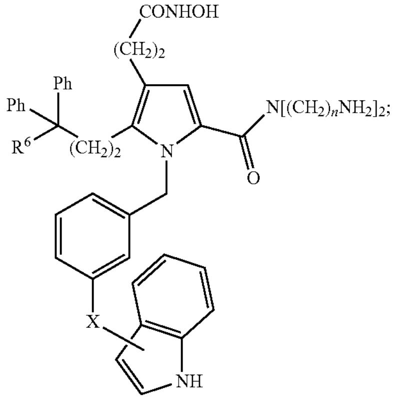
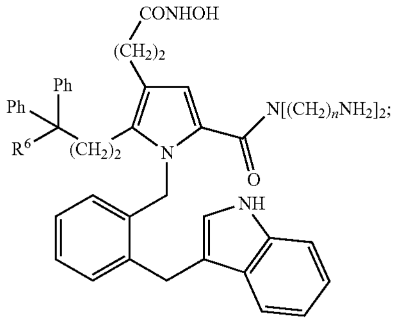
-continued
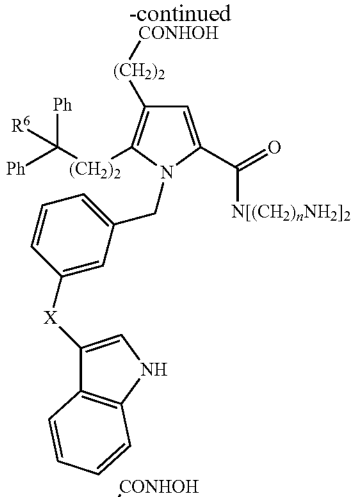
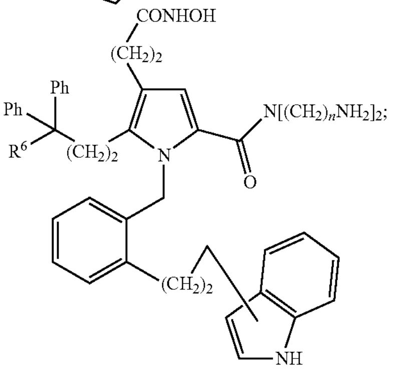
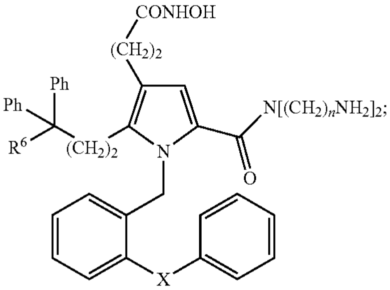
and
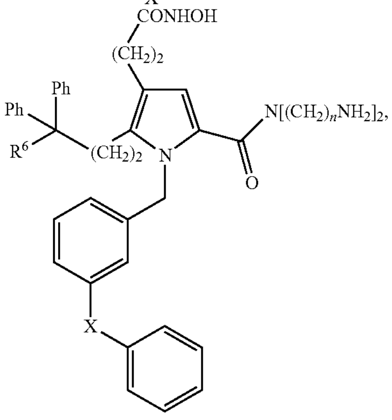
or a pharmaceutically acceptable salt or derivative thereof, wherein:
$R^6$ is chosen from H, OH, and $NH_2$;
m is an integer from 3 to 10;
n is an integer from 5 to 10;
X is chosen from $(CH_2)_{m1}V^1(CH_2)_{m2}V^2(CH_2)_{m3}$;

$V^1$ and $V^2$ are independently chosen from C, C(OH), O, S, and NH, or are absent;
m1 is an integer from 0 to 4;
m2 is an integer from 0 to 4; and
m3 is an integer from 0 to 4.
Exemplary compounds according to Formula (II-A) include:
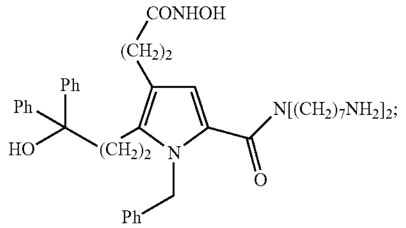
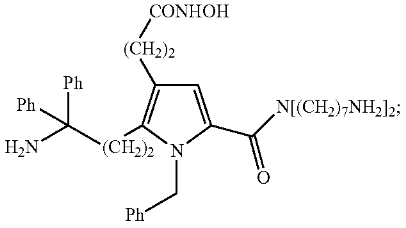
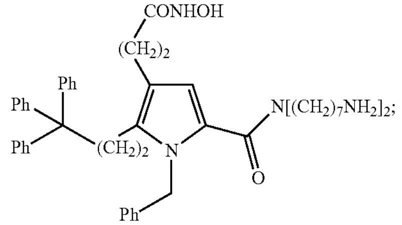
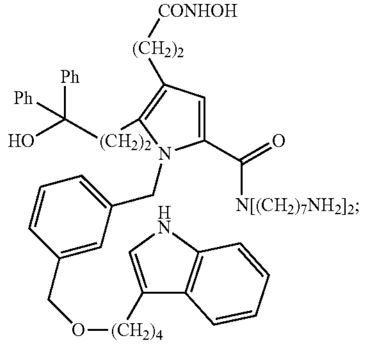
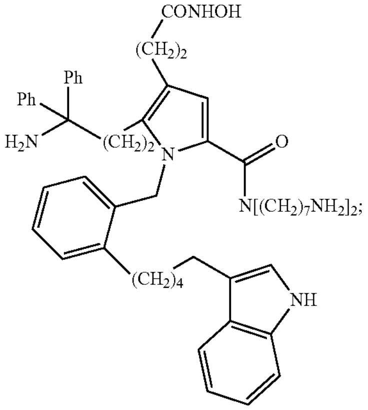
-continued
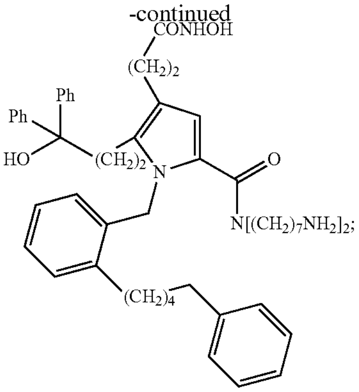
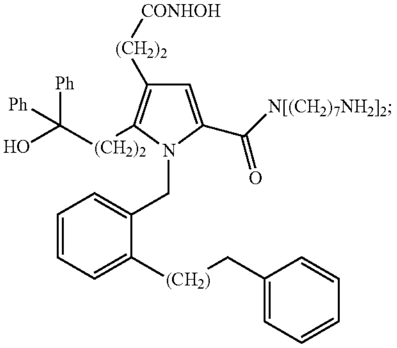
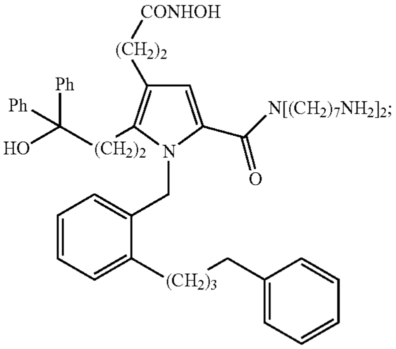
and
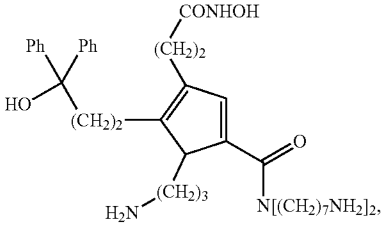
or a pharmaceutically acceptable salt or derivative thereof.
Also provided herein is a composition comprising a compound of Formula (III-A):
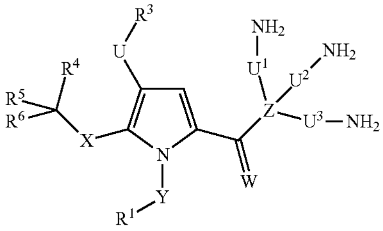

or a pharmaceutically acceptable salt or derivative thereof, wherein:

$R^1$ is chosen from $NH_2$, aryl, and heteroaryl;

Z is chosen from C, $(CH_2)_mC$, aryl, and heteroaryl;

m is an integer from 1 to 5;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $NH_2$, aryl, and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

$U^1$, $U^2$, and $U^3$ are independently $(CH_2)_{m1}V^1(CH_2)_{m2}V^2(CH_2)_{m3}$;

$V^1$ and $V^2$ are independently chosen from C, C(OH), O, S, and NH, or are absent;

m1 is an integer from 0 to 4;

m2 is an integer from 0 to 4;

m3 is an integer from 0 to 4;

W is O, S, or absent;

Y is chosen from $CO(CH_2)_{m4}$, $(CH_2)_{m4}$, and $CONH(CH_2)_{m4}$;

m4 is an integer from 1 to 8; and all non-hydrogen atoms in the pyrrole ring can be substituted by N, S, or O provided the substitution maintains aromaticity.

This disclosure further provides a composition comprising a compound of Formula (IV-A):

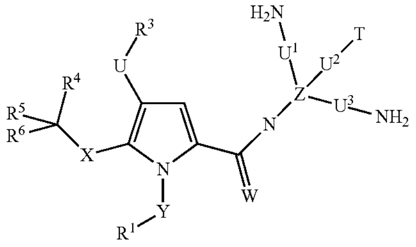

or a pharmaceutically acceptable salt or derivative thereof, wherein:

$R^1$ is chosen from $NH_2$, aryl, and heteroaryl;

Z is chosen from C, $(CH_2)_mC$, aryl, and heteroaryl;

m is an integer from 1 to 5;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $NH_2$, aryl, and heteroaryl;

T is chosen from $NH_2$, indole, aryl, and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

$U^1$, $U^2$, and $U^3$ are independently $(CH_2)_{m1}V^1(CH_2)_{m2}V^2(CH_2)_{m3}$;

$V^1$ and $V^2$ are independently chosen from C, C(OH), O, S, and NH, or are absent;

m1 is an integer from 0 to 4;

m2 is an integer from 0 to 4;

m3 is an integer from 0 to 4;

W is chosen from O and S, or is absent;

Y is chosen from $CO(CH_2)_{m4}$, $(CH_2)_{m4}$, and $CONH(CH_2)_{m4}$;

m4 is an integer from 1 to 8; and all non-hydrogen atoms in the pyrrole ring can be substituted by N, S, or O provided the substitution maintains aromaticity.

In some embodiments, the compound of Formula (IV-A) is chosen from:

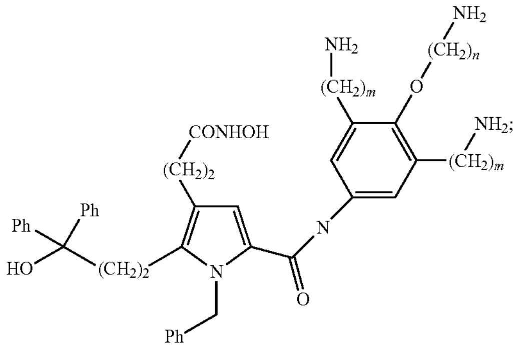

and

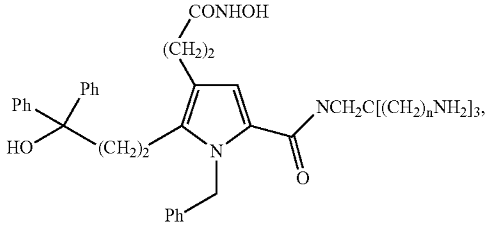

or a pharmaceutically acceptable salt or derivative thereof, wherein:

m is an integer from 3 to 10; and n is an integer from 3 to 10.

Exemplary compounds according to Formula (IV-A) include:

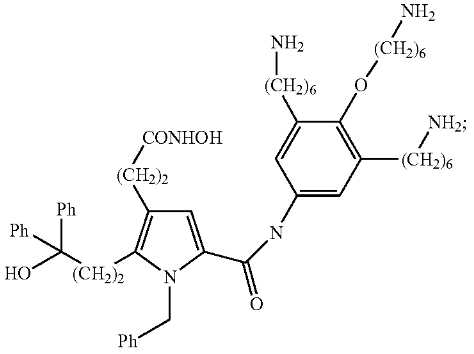

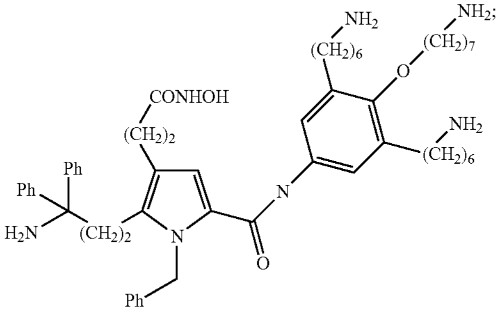

-continued

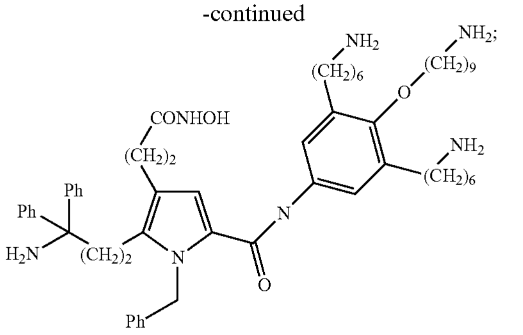

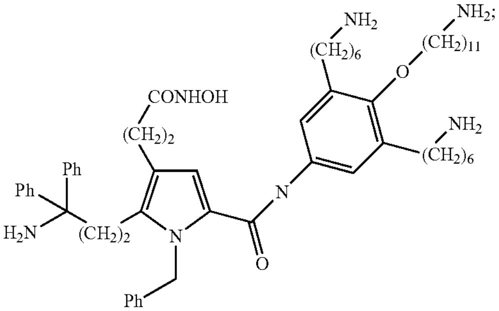

and

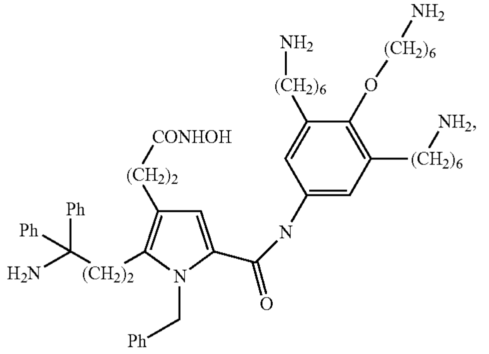

or a pharmaceutically acceptable salt or derivative thereof.

This disclosure also provides a method of treating or ameliorating one or more symptoms associated with Botulinum toxin poisoning comprising administering to a mammal a composition having one or more of the compounds disclosed herein. In some embodiments, the Botulinum toxin is BoNTA, BoNTD, BoNTE, or a mixture thereof. In some embodiments, the mammal is a human. The method can also include administering a trivalent equine antitoxin, penicillin G, or a mixture thereof to the mammal.

A method of inhibiting a zinc protease activity is provided, the method including contacting a zinc protease with a compound as described herein. In some embodiments, the zinc protease can be from BoNTA, BoNTD, or BoNTE.

Further provided herein is a method of treating a mammal that includes administering to the mammal a composition comprising a medical toxin based upon BoNT/LC-chimeras and a composition as described above. In some embodiments, the latter composition is administered to the mammal prior to the medical toxin. In some embodiments, the toxicity of the circulating BoNT or BoNT/LC chimera is reduced.

Also provided herein is a kit having a composition as described herein. In some embodiments, the kit includes a composition in the form of an injectable composition.

Pharmaceutical compositions are also described, wherein the pharmaceutical composition includes a compound as described herein and a pharmaceutically acceptable carrier, excipient, or adjuvant.

Further provided herein is a computer-assisted method of generating a test inhibitor of the active site of a Botulinum. The method can include using a programmed computer comprising a processor and an input device, and:

(a) inputting on the input device data comprising a docking box surrounded by one or more amino acid residues of the active site of a Botulinum, the residues having a confirmation as set forth in crystal structure PDB code 3BOO;

(b) docking into the docking box a test inhibitor molecule using the processor; and (c) determining, based on the docking, whether the test inhibitor molecule would be capable of interacting with one or more residues of the Botulinum active site. In some embodiments, docking can also include replacing the zinc ion in the active side of the Botulinum with a tetrahedral zinc ion. In some embodiments, docking can include inserting $Pro^{62}Pro^{63}Glu^{64}Ala^{65}Lys^{66}Gln^{67}$ into the gap between $Pro^{61}$ and $Val^{68}$ of the active site of the Botulinum. In some embodiments, inputing further comprises adding crystallographically determined water molecules to the active site of the Botulinum. In some embodiments, the test inhibitor molecule is capable of interacting with one or more of residues Glu224, Arg363, Tyr366, Phe194, Phe419, Asp370, Glu164, Glu56, Asp58, Glu251, Tyr245, Phe417, Asp153, Phe157, and Zn(II) of the Botulinum active site. In some embodiments, the method can also include evaluating the inhibitory activity of the test inhibitor in an HPLC assay.

A computer-assisted method of generating a test inhibitor of the active site of Botulinum, can include using a computing device and:

(a) receiving on a computing device data having a docking box surrounded by one or more amino acid residues of the active site of Botulinum, the residues having a confirmation as set forth in crystal structure PDB code 3BOO;

(b) docking into the docking box a test inhibitor molecule using the computing device; and (c) determining, using the computing device, based on the docking, whether the test inhibitor molecule would be capable of interacting with one or more residues of the Botulinum active site.

This disclosure also provides a composition, as described herein, for use in the treatment or amelioration of Botulinum toxin poisoning. In some embodiments, the Botulinum toxin is BoNTA, BoNTD, BoNTE, or mixtures thereof.

The compositions as described herein can also be used in the preparation of a medicament for the prevention, treatment or amelioration of Botulinum toxin poisoning. In some embodiments, the composition can be administered in a single dose or multiple doses of 2.0 mg/kg to protect mammals against the Botulinum toxin.

Also provided is an article of manufacture comprising a composition as described herein disposed within a pill, a table, a capsule, or a syringe.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a scheme illustrating a synthesis of E4.
FIG. 6 is a scheme illustrating a synthesis of E6.

FIG. 15 is a scheme illustrating a synthesis of E7.

FIG. 17 is a scheme illustrating a synthesis of E4b.

DETAILED DESCRIPTION

Figure 1:
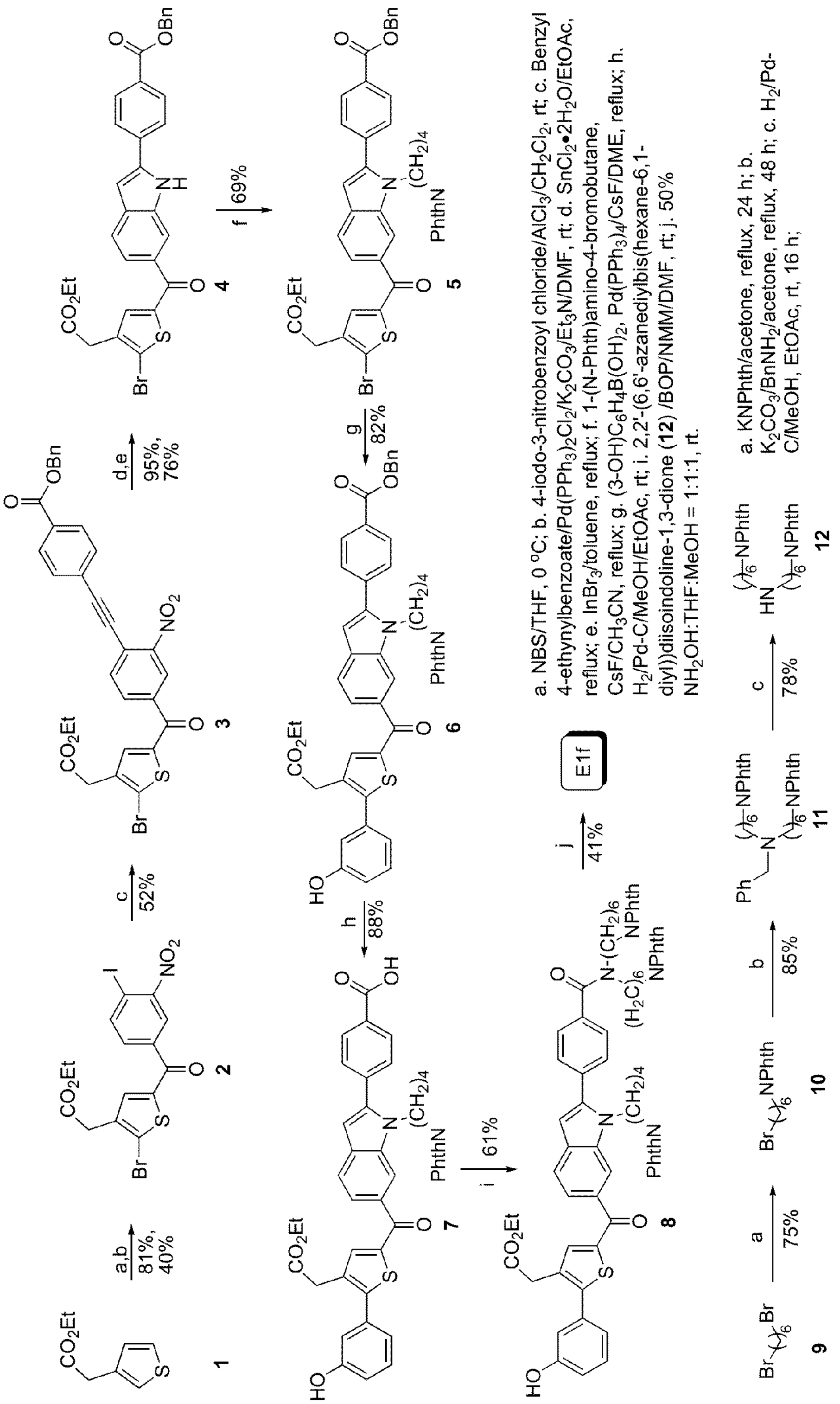
FIG. 1 is a scheme illustrating a synthesis of E1f.

Provided herein are small-molecule inhibitors of Botulinum neurotoxin, including BoNTA, BoNTD and BoNTE. The small-molecule inhibitors were designed to inhibit the zinc protease (a zinc endopeptidase) of BoNTA, hereafter abbreviated as BoNTAe, using, in part, information obtained from molecular modeling studies of BoNTAe and its active site. For example, the four-ligand coordination of the zinc ion embedded in the active site of the zinc endopeptidase was computationally simulated with the cationic dummy atom (CaDA) approach. (See Pang, Y.-P. J. Mol. Model. (1999) δ: 196; Pang, Y.-P.; Xu, K.; El Yazal, J.; Prendergast, F. G. Protein Sci. (2000) 9: 1857; Pang, Y.-P. Proteins. 2001, 45, 183; Oelschlaeger, P.; Schmid, R. D.; Pleiss, J. Protein Eng. (2003) 16: 341; Oelschlaeger, P.; Schmid, R. D.; Pleiss, J. Biochemistry (2003) 42: 8945; Park, J. G.; Sill, P. C.; Makiyi, E. F., Garcia-Sosa, A. T., Millard, C. B., Schmidt, J. J.; Pang, Y.-P. Bioorg. Med. Chem., (2006) 16: 395.) The CaDA approach enabled (i) refinement of the endopeptidase, (ii) identification of small molecules that were able to coordinate the zinc ion upon binding to the active site via docking and multiple molecular dynamics simulations (Pang, Y.-P. Proteins 2004:57:747), and (iii) optimization of the zinc-coordinating molecules via free energy perturbation study (Pang, Y. P.; Miller, J. L.; Kollman, P. A. J. Am. Chem. Soc. (1999) 121: 1717; Tang, J., Park, J. G., Millard, C. B., Schmidt, J. J., Pang, Y.-P. PLoS ONE (2007) 2: e761).

A. Definitions

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of Botulinum neurotoxin poisoning, e.g., BoNTA poisoning, are ameliorated or otherwise beneficially altered. Treatment also encompasses any pharmaceutical use of the compositions herein, such as uses for treating diseases, disorders, or ailments in which Botulinum neurotoxin is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response in an assay that measures such response.

As used herein, the term $K_i$ represents the dissociation constant of an enzyme/inhibitor complex. It is theoretically independent of the substrate against which the inhibitor is tested. $K_i$ can be calculated from an $IC_{50}$ using the equation: $K_i = IC_{50} * K_m/(S+K_m)$, where S is the concentration of substrate, and $K_m$ is the substrate concentration (in the absence of inhibitor) at which the velocity of the reaction is half-maximal. The $K_i$ of an inhibitor for inhibition of a particular substrate (fixed $K_m$) is constant.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" refer to carbon chains that may be straight or branched. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propenyl).

As used herein, "cycloalkyl" refers to a saturated mono- or multi-cyclic ring system, in certain embodiments of 3 to 10 carbon atoms, in other embodiments of 3 to 6 carbon atoms. The ring systems of the cycloalkyl groups may be composed of one ring or two or more rings which may be joined together in a fused, bridged or spiro-connected fashion. Examples include, but are not limited to, cyclopropyl, cyclobutyl, cyclopentyl, and cyclohexyl.

As used herein, "aryl" refers to aromatic monocyclic or multicyclic groups containing from 5 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members, where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "halo", "halogen" or "halide" refers to F, Cl, Br or I.

As used herein, "alkoxy" refers to RO—, in which R is alkyl.

Where the number of any given substituent is not specified (e.g., substituted phenyl), there may be one or more substituents present.

The definition of each expression, e.g., alkyl, m, n, and the like, when it occurs more than once in any structure, is intended to be independent of its definition elsewhere in the same structure.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

The compounds provided herein exhibit in vitro and in vivo activity against Botulinum neurotoxin poisoning (i.e., BoNTA, BoNTD, and/or BoNTE poisoning) and associated disorders. For example, the compounds provided herein can inhibit the zinc endopeptidase of BoNTA, which is thought to specifically cleave neuronal proteins that are responsible for acetylcholine release. In some embodiments, the inhibition of BoNTA is specific as compared to Botulinum neurotoxin serotype B (BoNTB). In one embodiment, the compounds treat, prevent, or ameliorate one or more symptoms associated with Botulinum neurotoxin poisoning, including BoNTA poisoning. In certain embodiments, the compounds inhibit the endopeptidase activity of BoNTA. In some embodiments, the compounds inhibit the endopeptidase activity of BoNTA, or BoNTE, or BoNTD.

Use of any of the compounds provided herein, or their pharmaceutically acceptable salts or derivatives, in the treatment or amelioration of Botulinum neurotoxin poisoning (e.g., BoNTA poisoning), or associated disorders is also provided, as well as use of any of the compounds, or pharmaceutically acceptable salts or derivatives, in the preparation of a medicament for the treatment or amelioration of Botulinum neurotoxin poisoning (e.g., BoNTA poisoning).

Compounds for use in the compositions and methods provided herein, or pharmaceutically acceptable salts or derivatives thereof, can have Formula (I-A):

I-A

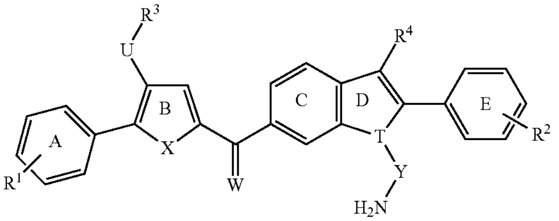

wherein:

$R^1$ is chosen from OH and $NH_2$;

$R^2$ is chosen from H, OH, halo, $C_{1-10}$ alkyl, $C_{2-10}$ alkenyl, $C_{2-10}$ alkynyl, $C_{1-10}$ alkoxy, cycloalkyl, aryl, heteroaryl, $CONH_2$, and $CONR^{2a}R^{2b}$;

$R^{2a}$ and $R^{2b}$ are independently chosen from $(CH_2)_{m3}NH_2$;

m3 is an integer from 4 to 12;

$R^3$ is chosen from thiol, imidazole, sulfonamide, COOH, and CONHOH;

$R^4$ is chosen from H, F, Cl, and Br;

X is chosen from S, NH, and O;

T is chosen from C and N;

U is $(CH_2)_{m1}V(CH_2)_{m2}$;

V is chosen from C, C(OH), O, S, and NH, or is absent;

m1 is an integer from 0 to 3;

m2 is an integer from 0 to 3;

W is chosen from O and S;

Y is chosen from $CO(CH_2)_{m4}$, $(CH_2)_{m4}$, and $CONH(CH_2)_{m4}$;

m4 is an integer from 2 to 8;

all non-hydrogen atoms in rings A-E can be substituted by N, S, or O provided the substitution maintains aromaticity; and wherein if $R^4$ is H then $R^2$ is not H.

In some embodiments, $R^2$ is chosen from H, OH, $CONH_2$, and $CONR^{2a}R^{2b}$. In some embodiments, $R^2$ is H or $CONR^{2a}R^{2b}$. In some embodiments, $R^2$ is $CON((CH_2)_{10}NH_2)_2$. In some embodiments, m3 is 5, 6, 8, or 10. In some embodiments, $R^3$ is CONHOH. In some embodiments, $R^4$ is H or F. In some embodiments, $R^4$ is F. In some embodiments, X is S. In some embodiments, T is N. In some embodiments, U is $(CH_2)_{m1}$. In some embodiments, U is $CH_2$. In some embodiments, Y is $(CH_2)_{m4}$. In some embodiments, Y is $(CH_2)_4$.

In some embodiments, the compound of Formula (I-A) can have Formula (I-B), (I-C), or (I-D):

I-B

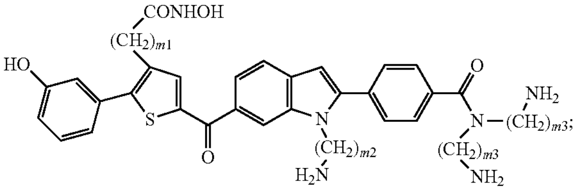

I-C

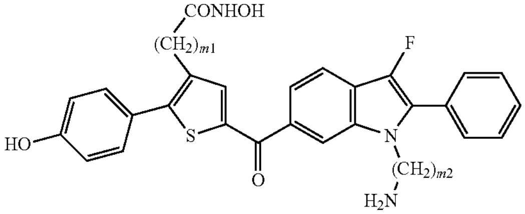

; and

I-D

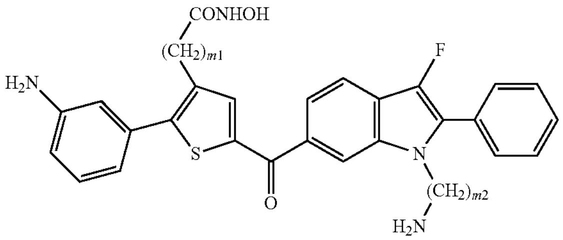

, or a pharmaceutically acceptable salt or derivative thereof, wherein:

m1 is an integer from 1 to 2;

m2 is an integer from 3 to 8; and m3 is an integer from 6 to 12.

Exemplary compounds according to one or more of Formulas (I-A), (I-B), (I-C) and (I-D) include:

E1

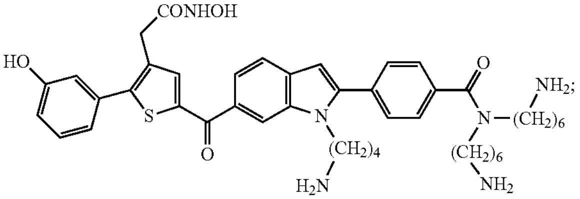

E1b

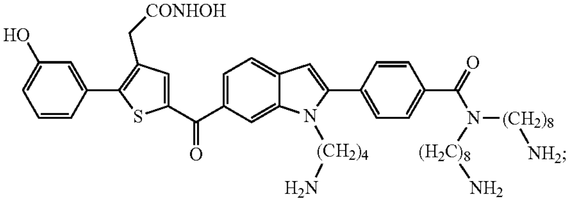

E1c

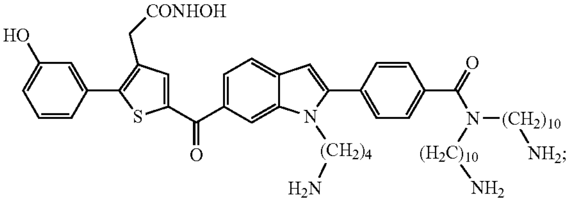

E1d

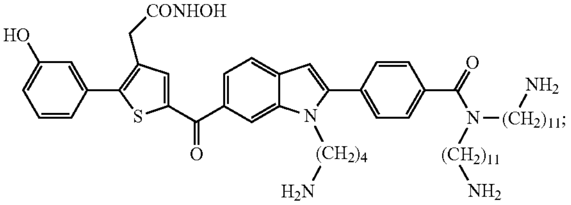

E1e

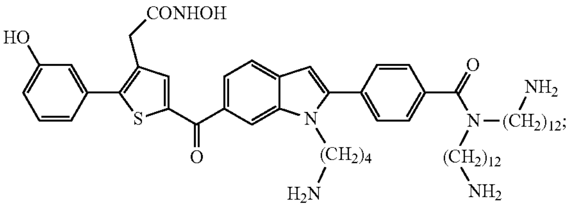

E1f

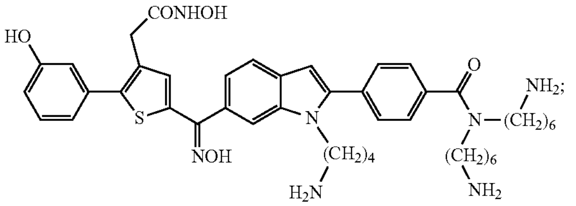

-continued

E1g

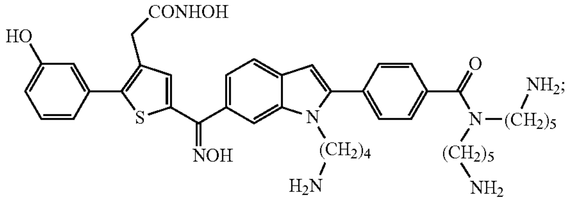

E1h

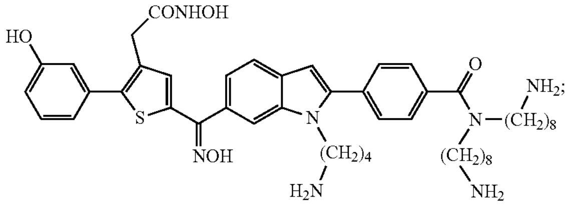

E2

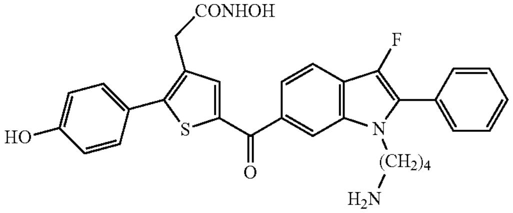

; and

E3

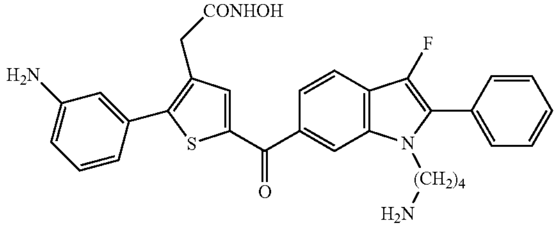

, or a pharmaceutically acceptable salt or derivative thereof.

Another compound for use in the compositions and methods provided herein, or pharmaceutically acceptable salts or derivatives thereof, can have Formula (II-A):

II-A

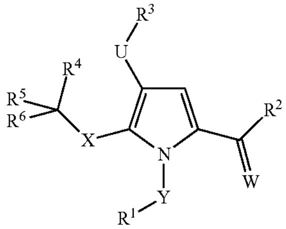

wherein:

$R^1$ is chosen from $NH_2$, aryl and heteroaryl;

$R^2$ is $NR^{2a}R^{2b}$;

$R^{2a}$ and $R^{2b}$ are independently $(CH_2)_nNH_2$;

n is an integer from 4 to 12;

$R^3$ is chosen from thiol, imidazole, sulfonamide, COOH, and CONHOH;

$R^4$ and $R^5$ are independently chosen from aryl or heteroaryl;

$R^6$ is chosen from H, OH, $NH_2$, aryl and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

W is chosen from O and S, or is absent;

Y is chosen from $CO(CH_2)_{m3}$, $(CH_2)_{m3}$, and $CONH(CH_2)_{m3}$;

m3 is an integer from 1 to 10; and all non-hydrogen atoms in the pyrrole ring can be substituted by N, S, or O provided the substitution maintain aromaticity.

In some embodiments, $R^1$ is chosen from $NH_2$, or a substituted or unsubstituted five- or six-membered aryl ring. In some embodiments, $R^1$ is phenyl. In some embodiments, $R^1$ is a substituted phenyl. In some embodiments, $R^2$ is $N[(CH_2)_7NH_2]_2$. In some embodiments, $R^3$ is CONHOH. In some embodiments, $R^4$ and $R^5$ are independently a substituted or unsubstituted five- or six-membered aryl. In some embodiments, $R^4$ and $R^5$ are phenyl or substituted phenyl. In some embodiments, $R^6$ is chosen from H, OH, $NH_2$, or a substituted or unsubstituted five- or six-membered aryl. In some embodiments, $R^6$ is chosen from H, OH, and $NH_2$. In some embodiments, U is $(CH_2)_{m1}$. In some embodiments, U is $(CH_2)_2$. In some embodiments, X is $(CH_2)_{m1}$. In some embodiments, X is $(CH_2)_2$. In some embodiments, W is O. In some embodiments, Y is $(CH_2)_{m3}$. In some embodiments, Y is $CH_2$.

In some embodiments, the compound of Formula (II-A) can have Formula (II-B), (II-C), (II-D), (II-E), (II-F), (II-G), (II-H), or (II-J):

II-B

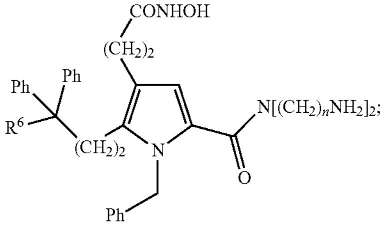

II-C

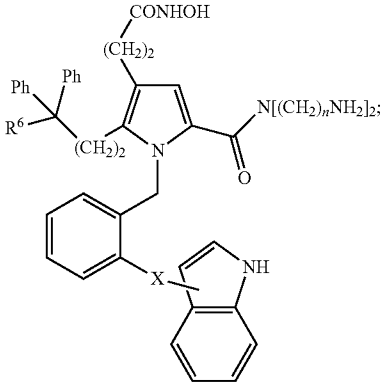

II-D

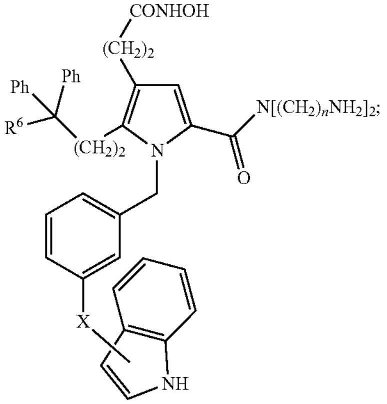

-continued

II-E

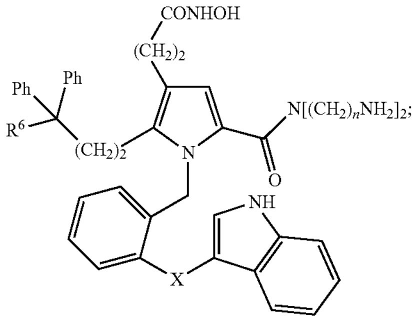

II-F

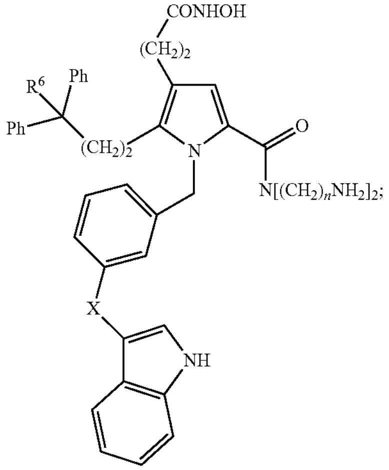

II-G

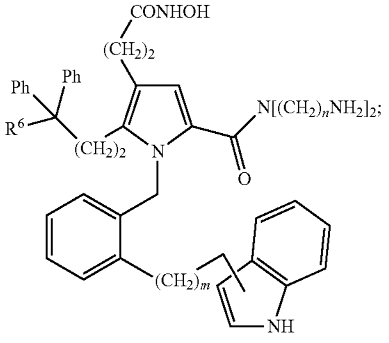

II-H

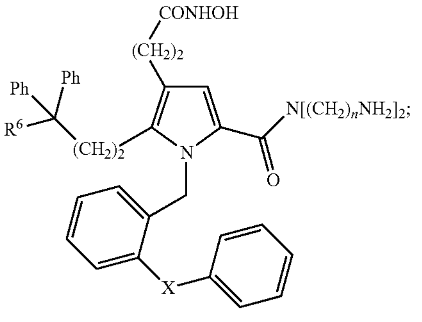

and

-continued

II-J

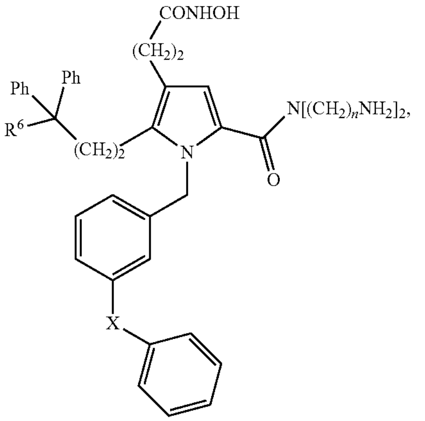

or a pharmaceutically acceptable salt or derivative thereof, wherein:

$R^6$ is chosen from H, OH, and $NH_2$;

m is an integer from 3 to 10;

n is an integer from 5 to 10;

X is $(CH_2)_{m1}V^1(CH_2)_{m2}V^2(CH_2)_{m3}$;

$V^1$ and $V^2$ are independently chosen from C, C(OH), O, S, and NH, or are absent;

m1 is an integer from 0 to 4;

m2 is an integer from 0 to 4; and m3 is an integer from 0 to 4.

Exemplary compounds according to one or more of Formulas (II-A), (II-B), (II-C), (II-D), (II-E), (II-F), (II-G), (II-H), or (II-J) include:

E4

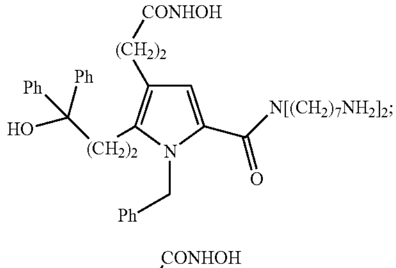

E4b

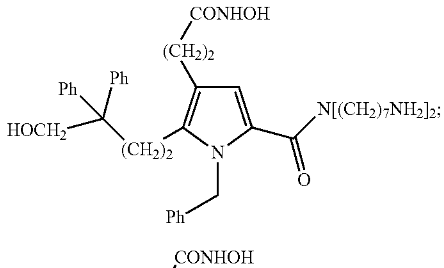

E7

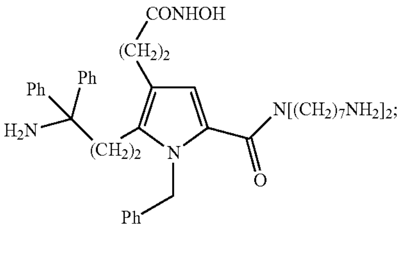

-continued

E12

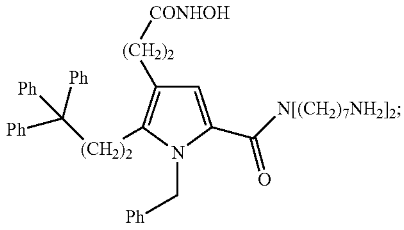

E5

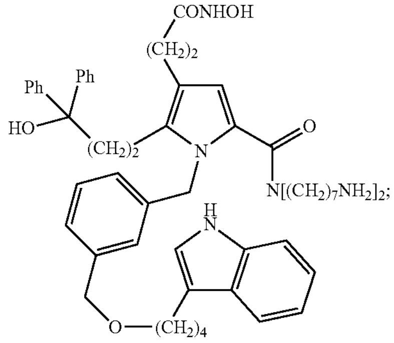

E8

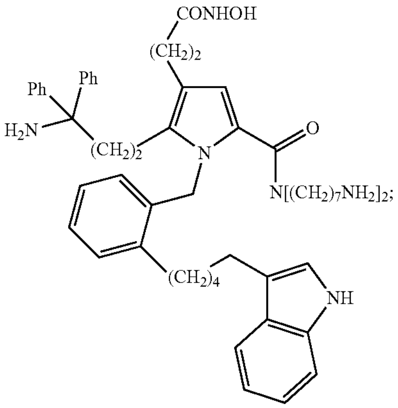

E11

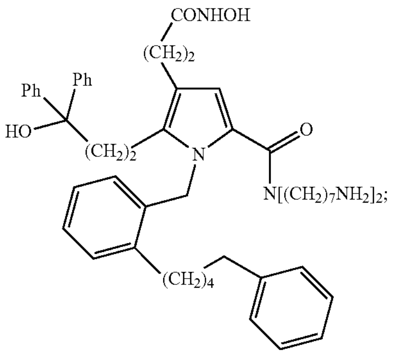

-continued

E11b

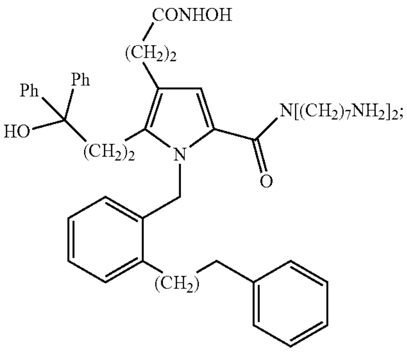

E11c

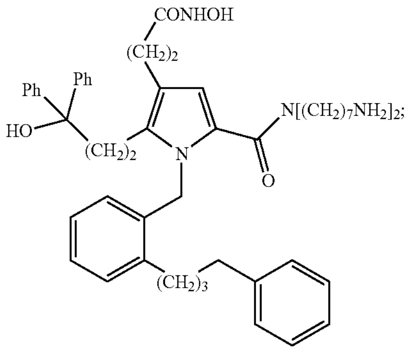

and

E10

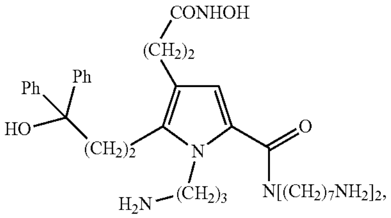

or a pharmaceutically acceptable salt or derivative thereof.

This disclosure also provides a compound of Formula (III-A) for use in the compositions and methods provided herein, or pharmaceutically acceptable salts or derivatives thereof:

III-A

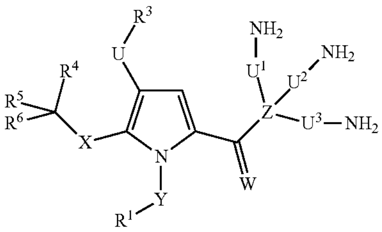

wherein:

$R^1$ is chosen from $NH_2$, aryl, or heteroaryl;

Z is chosen from C, $(CH_2)_mC$, aryl, and heteroaryl;

m is an integer from 1 to 5;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $NH_2$, aryl, and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

$U^1$, $U^2$, and $U^3$ are independently $(CH_2)_{m1}V^1(CH_2)_{m2}V^2(CH_2)_{m3}$;

$V^1$ and $V^2$ are independently chosen from C, C(OH), O, S, and NH or are absent;

m1 is an integer from 0 to 4;

m2 is an integer from 0 to 4;

m3 is an integer from 0 to 4;

W is O, S, or absent;

Y is chosen from $CO(CH_2)_{m4}$, $(CH_2)_{m4}$, and $CONH(CH_2)_{m4}$; and m4 is an integer from 1 to 8;

all non-hydrogen atoms in the pyrrole ring can be substituted by N, S, or O provided the substitution maintains aromaticity.

In some embodiments, $R^1$ is chosen from $NH_2$, or a substituted or unsubstituted five- or six-membered aryl ring. In some embodiments, $R^1$ is phenyl. In some embodiments, $R^1$ is a substituted phenyl.

Further provided herein for use in the compositions and methods described, or pharmaceutically acceptable salts or derivatives thereof, is a compound of Formula (IV-A):

IV-A

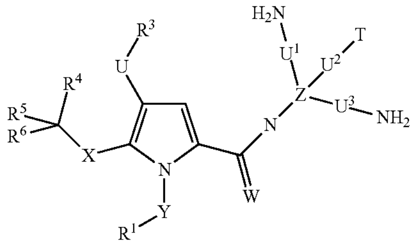

wherein:

$R^1$ is chosen from $NH_2$, aryl, and heteroaryl;

Z is chosen from C, $(CH_2)_mC$, aryl, and heteroaryl;

m is an integer from 1 to 5;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $NH_2$, aryl, and heteroaryl;

T is chosen from $NH_2$, indole, aryl, and heteroaryl;

U and X are independently $(CH_2)_{m1}V(CH_2)_{m2}$;

V is chosen from C, C(OH), O, S, and NH, or is absent;

m1 is an integer from 0 to 2;

m2 is an integer from 0 to 2;

$U^1$, $U^2$, and $U^3$ are independently $(CH_2)_{m1}V^1(CH_2)_{m2}V^2(CH_2)_{m3}$;

$V^1$ and $V^2$ are independently chosen from C, C(OH), O, S, and NH, or are absent;

m1 is an integer from 0 to 4;

m2 is an integer from 0 to 4;

m3 is an integer from 0 to 4;

W is O, S, or absent;

Y is chosen from $CO(CH_2)_{m4}$, $(CH_2)_{m4}$, and $CONH(CH_2)_{m4}$; and m4 is an integer from 1 to 8;

All non-hydrogen atoms in the pyrrole ring can be substituted by N, S, or O provided the substitution maintains aromaticity.

In some embodiments, $R^1$ is chosen from $NH_2$, or a substituted or unsubstituted five- or six-membered aryl ring. In some embodiments, $R^1$ is phenyl. In some embodiments, Z is chosen from C, $CH_2C$, or phenyl. In some embodiments, Z is $CH_2C$. In some embodiments, Z is phenyl. In some embodiments, $R^3$ is CONHOH. In some embodiments, $R^4$ and $R^5$ are independently a substituted or unsubstituted five- or six-membered aryl ring. In some embodiments, $R^4$ and $R^5$ are phenyl. In some embodiments, $R^6$ is chosen from H, OH, $NH_2$, or a substituted or unsubstituted five- or six-membered membered aryl ring. In some embodiments, $R^6$ is chosen from H, OH, and $NH_2$. In some embodiments, U is $(CH_2)_{m1}$. In some embodiments, U is $(CH_2)_2$. In some embodiments, X is $(CH_2)_{m1}$. In some embodiments, X is $(CH_2)_2$. In some embodiments, W is O. In some embodiments, Y is $(CH_2)_{m3}$. In some embodiments, Y is $CH_2$. In some embodiments, $V^1$ and $V^2$ are absent.

In some embodiments, a compound of Formula (IV-A) can have Formula (IV-B) or (IV-C):

IV-B

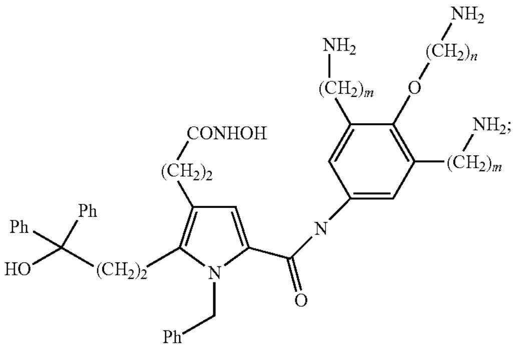

and

IV-C

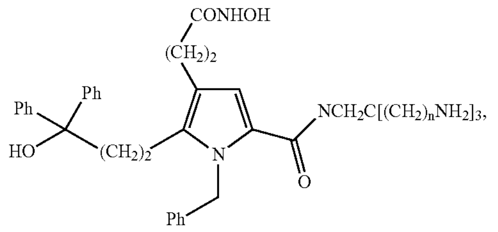

or a pharmaceutically acceptable salt or derivative thereof, wherein:

m is an integer from 3 to 10; and n is an integer from 3 to 10.

Exemplary compounds according to one or more of Formula (IV-A), (IV-B), or (IV-C) include:

E6

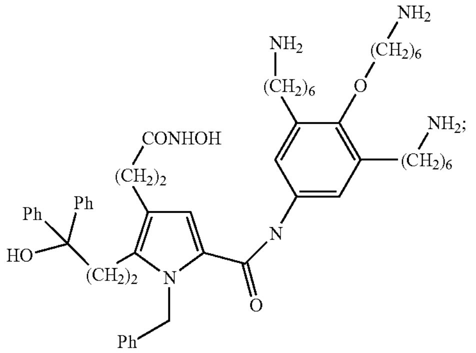

-continued

E6b

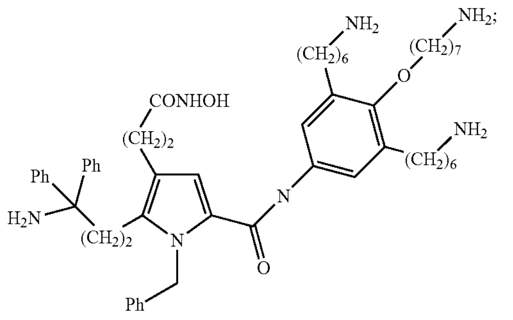

E6c

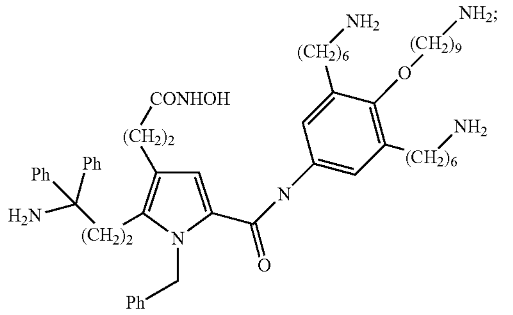

E6d

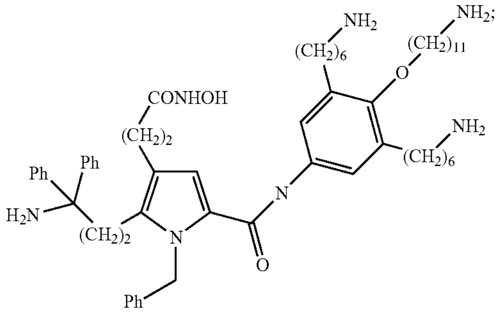

and

E9

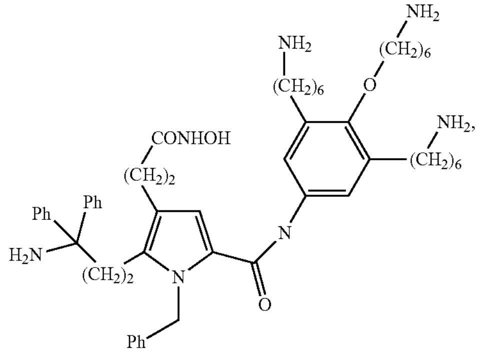

or a pharmaceutically acceptable salt or derivative thereof.

C. Preparation of the Compounds

The compounds for use in the compositions and methods provided herein may be prepared by methods known to those of skill in the art or by the methods shown herein (e.g., see FIGS. 1-6 and the Examples, below). One of skill in the art would be able to prepare all of the compounds for use herein by routine modification of these methods using the appropriate starting materials.

D. Formulation of Pharmaceutical Compositions

The pharmaceutical compositions provided herein contain therapeutically effective amounts of one or more of the compounds provided herein that are useful in the treatment, prevention, or amelioration of one or more of the symptoms associated with Botulinum toxin poisoning (e.g., BoNTA poisoning), or a disorder or ailment in which Botulinum toxin poisoning (e.g., BoNTA poisoning) is implicated, and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats or ameliorates one or more of the symptoms of Botulinum toxin poisoning, e.g., BoNTA poisoning.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disorder being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, or in one embodiment 0.1-95%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyvinylpyrrolidone, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents.

The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action. The active ingredient is a compound or pharmaceutically acceptable derivative thereof as described herein. Higher concentrations, up to about 98% by weight of the active ingredient, may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

2. Injectables, Solutions, and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration should be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to target a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture (e.g., kits) containing packaging material, one or more compounds or pharmaceutically acceptable derivatives thereof provided herein within the packaging material, and a label that indicates that the compound or composition, or pharmaceutically acceptable derivative thereof, is useful for treatment, prevention, or amelioration of one or more symptoms or disorders in which Botulinum neurotoxin poisoning, including BoNTA poisoning, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

8. Sustained Release Formulations

Also provided are sustained release formulations to deliver the compounds to the desired target at high circulating levels (between $10^{-9}$ and $10^{-4}$ M). The levels are either circulating in the patient systemically, or in one embodiment, localized to a site of, e.g., paralysis.

It is understood that the compound levels are maintained over a certain period of time as is desired and can be easily determined by one skilled in the art. Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

E. Evaluation of the Activity of the Compounds

The activity of the compounds provided herein as inhibitors of Botulinum toxin poisoning (e.g., BoNTA poisoning), or BoNTA zinc endopeptidase activity, may be measured in standard assays, e.g., HPLC assays, such as those described in Schmidt, J. J., Bostian, K. A., *J. Protein Chem.* (1997), 16, 19, in which a test compound was added to an assay mixture containing a substrate of Botulinum toxin, followed by addition of the toxin. The assay time and toxin concentration were adjusted so that less than 10% of the substrate was hydrolyzed. The assay was stopped by acidification with trifluoroacetic acid and analyzed by reverse-phase HPLC. The percent proteolysis of the substrate was calculated by dividing the combined areas of the peaks representing the cleavage products by the sum of the areas of the cleavage products plus uncleaved parent substrate. Other methods of evaluating the activity of the compounds described herein are shown in Examples 8 and 9.

F. Methods of Use of the Compounds and Compositions

Provided herein are methods to treat, prevent, or ameliorate symptoms or disorders associated with Botulinum toxin poisoning, including food-borne botulism, infant botulism, wound botulism, adult enteric infectious botulism, and inhalation botulism, and BoNTA, BoNTD or BoNTE poisoning; and methods to inhibit zinc protease activity, including BoNTA, BoNTD or BoNTE zinc protease activity. The methods include administering one or more of the compounds described herein, or a pharmaceutically acceptable salt or derivative thereof, to a mammal, e.g., a human, cat, dog, horse, pig, cow, sheep, mouse, rat, or monkey. In certain cases, the methods can be used to counter-effect Botulinum toxin poisoning from cosmetic BOTOX® injections. In certain cases, the methods can be used to counter-effect Botulinum toxin poisoning from biological-based weapons.

In certain embodiments, the symptoms or disorders associated with Botulinum toxin poisoning include one or more of the following: muscular paralysis, difficulty breathing, asphyxiation, suffocation, fatigue, dizziness, double vision, blurred vision, dysphagia, dry mouth, dysarthria, sore throat, dyspnea, constipation, nausea, vomiting, abdominal pain, diarrhea, arm weakness, leg weakness, paresthesia, alert mental status, ptosis, gaze paralysis, fixation or dilation of the pupils, nystagmus, facial palsy, diminished gag reflex, and tongue weakness.

Further provided herein is a method of treating a mammal undergoing treatment with a medical toxin based upon BoNT/LC-chimeras. Such medical toxins can include, for example, a MAb-based immunotoxin or a pain-receptor-binding protein coupled to BoNTA/LC. In some embodiments, the mammal can be administered a composition comprising the medical toxin and a composition having one or more of the compounds described herein, or a pharmaceutically acceptable salt or derivative thereof. The latter composition can be administered before, after, or concurrently with the medical toxin. In some embodiments the medical toxin and the composition having one or more of the compounds described herein are combined prior to administration. Without being bound by theory, the administration of one or more of the botulinum inhibitory compounds, as described herein, can function to reduce the toxicity of the circulating BoNT or BoNT/LC chimeras present in the mammal following administration of the medical toxin.

In practicing the methods, effective amounts of the compounds or composition provided herein are administered. Such amounts are sufficient to achieve a therapeutically effective concentration of the compound or active component of the composition in vivo.

G. Methods of Designing Inhibitors Targeting the Botulinum Active Site

Provided herein are methods, including computer-based methods using the cationic dummy atom (CaDA) approach (See Pang, Y.-P. *J. Mol. Model.* (1999) δ: 196; Pang, Y.-P.; Xu, K.; El Yazal, J.; Prendergast, F. G. *Protein Sci.* (2000) 9: 1857; Pang, Y.-P. Proteins. 2001, 45, 183; Oelschlaeger, P.; Schmid, R. D.; Pleiss, J. *Protein Eng.* (2003) 16: 341; Oelschlaeger, P.; Schmid, R. D.; Pleiss, J. *Biochemistry* (2003) 42: 8945; Park, J. G.; Sill, P. C.; Makiyi, E. F., Garcia-Sosa, A. T., Millard, C. B., Schmidt, J. J., Pang, Y.-P. *Bioorg. Med. Chem.*, (2006) 16: 395), for designing compounds that bind to and/or inhibit an active site of botulinum as set forth in the crystal structure having PDB code 3BOO. The active site of botulinum includes, but is not limited to, the residues in the active site of the crystal structure 3BOO. For example, the active site includes residues Glu224, Arg363, Tyr366, Phe194, Phe419, Asp370, Glu164, Glu56, Asp58, Glu251, Tyr245, Phe417, Asp153, Phe157, and Zn(II).

The inventors have determined that the conformations of residues in the active site, as found in crystal structure 3BOO, are useful for determining inhibitors with high affinity for the active site. Thus, given the three-dimensional model described herein as well as the identification of the proper configuration of the active site as useful residues to target, one having ordinary skill in the art would know how to use standard molecular modeling or other techniques to identify peptides, peptidomimetics, and small-molecules that would bind to or interact with one or more of the residues in the active site. In addition, one having ordinary skill in the art would be able to combine targeting such residues with the targeting of other amino acids that are located at the rim of the active site.

By "molecular modeling" is meant quantitative and/or qualitative analysis of the structure and function of physical interactions based on three-dimensional structural information and interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. See Example 9 below.

Methods of designing compounds that bind specifically (e.g., with high affinity) to one or more of the residues described previously typically are also computer-based, and involve the use of a computer having a program capable of generating an atomic model. Computer programs that use X-ray crystallography data or molecular model coordinate data, such as the data that are available from the PDB, are particularly useful for designing such compounds. Programs such as RasMol, for example, can be used to generate a three dimensional model. Computer programs such as INSIGHT (Accelrys, Burlington, Mass.), Auto-Dock (Accelrys), and Discovery Studio 1.5 (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, a computer-assisted method of generating a test inhibitor of the active site of Botulinum as set forth by the crystal structure 3BOO is provided. The method uses a programmed computer comprising a processor and an input device, and can include:

(a) inputting on the input device, e.g., through a keyboard, a diskette, or a tape, data (e.g. atomic coordinates) comprising a docking box surrounded by one or more one residues of the active site of Botulinum as defined by the 3BOO crystal structure;

(b) docking into the docking box a test inhibitor molecule using the processor; and (c) determining, based on the docking, whether the test inhibitor molecule would be capable of interacting with the one or more residues of the active site.

In some embodiments, the method uses a programmed computer comprising a processor, and can include:

(a) receiving data (e.g. atomic coordinates) comprising a docking box surrounded by one or more one residues of the active site of Botulinum as defined by the 3BOO crystal structure at a computing device;

(b) docking into the docking box a test inhibitor molecule using the processor; and (c) determining in the computing device, based on the docking, whether the test inhibitor molecule would be capable of interacting with the one or more residues of the active site.

In some embodiments, the method can further include storing in a computer memory storage location the results of docking a test inhibitor molecule into the docking box (e.g., interaction energy values and binding strengths).

In some embodiments, the docking can include replacing the zinc ion in the active side of the Botulinum with a tetrahedral zinc ion (See Pang, Y.-P. J. Mol. Model. (1999) 5: 196; Pang, Y.-P.; Xu, K.; El Yazal, J.; Prendergast, F. G. *Protein Sci*. (2000) 9: 1857; Pang, Y.-P. Proteins. 2001, 45, 183; Oelschlaeger, P.; Schmid, R. D.; Pleiss, J. *Protein Eng*. (2003) 16: 341; Oelschlaeger, P.; Schmid, R. D.; Pleiss, J. *Biochemistry* (2003) 42: 8945; Park, J. G.; Sill, P. C.; Makiyi, E. F., Garcia-Sosa, A. T., Millard, C. B., Schmidt, J. J., Pang, Y.-P. Bioorg. Med. Chem., (2006) 16: 395). In some embodiments, the docking can also include inserting $Pro^{62}Pro^{63}Glu^{64}Ala^{65}Lys^{66}Gln^{67}$ into the gap between $Pro^{61}$ and $Val^{68}$ of the active site of the Botulinum. In some embodiments, the inputing can also include adding crystallographically determined water molecules to the active site of the Botulinum.

In some embodiments, the docking box is surrounded by one or more of the residues Glu224, Arg363, Tyr366, Phe194, Phe419, Asp370, Glu164, Glu56, Asp58, Glu251, Tyr245, Phe417, Asp153, and Phe157 having conformations as set forth in the 3BOO crystal structure. In some embodiments, the test inhibitor molecule is capable of interacting with one or more of residues Glu224, Arg363, Tyr366, Phe194, Phe419, Asp370, Glu164, Glu56, Asp58, Glu251, Tyr245, Phe417, Asp153, Phe157, and Zn(II) having conformations as set forth in the 3BOO crystal structure. For example, the test inhibitor compound could form one or more of the following interactions: cation-pi interactions with one or more of residues R363, F157, and F194; pi-pi interactions with one or more of residues Y366, F419, Y245, F363, F417, and F194; hydrogen bonds to one or more of residues D370 and E224; ionic interactions with one or more of residues D370, E164, E56, E251, D153 and D58.

By "capable of interacting" it is meant capable of forming a one or more hydrogen bonds, ionic bonds, covalent bonds, pi-pi interactions, cation-pi interactions, sulfur-aromatic interactions, or VdW interactions. In some embodiments, the test inhibitor molecule can interact with one or more residues of the active site of Botulinum with a minimum interaction energy of −5 to about −50 kcal/mol, e.g., −20 to −40 kcal/mol. In some embodiments, the test inhibitor would be capable of forming a hydrogen bond with one or more residues of the active site of Botulinum.

The inhibitory activity of the test inhibitor on Botulinum can be evaluated. In some embodiments, the inhibitory activity is evaluated using an in vitro HPLC assay as described herein or another in vitro or in vivo activity assay that can evaluate activity of the compound on the Botulinum, for example, see Examples 8 and 9.

From the information obtained using these methods, one skilled in the art will be able to design and make inhibitory compounds (e.g., peptides, non-peptide small molecules, peptidomimetics, and aptamers (e.g., nucleic acid aptamers)) with the appropriate 3-D structure, e.g., at certain residues and that interact in certain manners (e.g., hydrogen-bonding, ion bonding, covalent bonding, pi-pi interactions, sulfur-aromatic interactions, steric interactions, and/or van der Waals interactions). For example, one of skill in the art could design inhibitory compounds that could interact with one or more of the residues corresponding to Glu224, Arg363, Tyr366, Phe194, Phe419, Asp370, Glu164, Glu56, Asp58, Glu251, Tyr245, Phe417, Asp153, Phe157, Zn(II) whose confirmations are as defined in the 3BOO crystal structure.

Moreover, if computer-usable 3-D data (e.g., x-ray crystallographic data) for a candidate compound are available, one or more of the following computer-based steps can be performed in conjunction with computer-based steps described above:

(d) inputting into an input device, e.g., through a keyboard, a diskette, or a tape, data (e.g. atomic coordinates) that define the three-dimensional (3-D) structure of a candidate compound;

(e) determining, using a processor, the 3-D structure (e.g., an atomic model) of the candidate compound;

(f) determining, using the processor, whether the candidate compound binds to or interacts with one or more of the residues of interest in the ricin active site;

(g) determining the interaction energy of the candidate compound;

(h) identifying the candidate compound as a compound that inhibits the site;

(j) receiving, through an input device, e.g., through a keyboard, a diskette, or a tape, data (e.g. atomic coordinates) that define the three-dimensional (3-D) structure of a candidate compound at a computing device;

(k) determining, using the computing device, the 3-D structure (e.g., an atomic model) of the candidate compound;

(l) determining, using the computing device, whether the candidate compound binds to or interacts with one or more of the residues of interest in the ricin active site;

(m) determining, using the computing device, the interaction energy of the candidate compound; and (n) identifying, using the computing device, the candidate compound as a compound that inhibits the site.

The method can involve an additional step of outputting to an output device a model of the 3-D structure of the compound. The method can also involve an additional step of storing in a computer memory storage location the results of any step of the method. In addition, the 3-D data of candidate compounds can be compared to a computer database of, for example, 3-D structures stored in a data storage system. In some embodiments, the interaction energy of the candidate compound is less than −54 kcal/mol.

Candidate compounds identified as described above can then be tested in standard cellular inhibition assays familiar to those skilled in the art.

The 3-D structure of molecules can be determined from data obtained by a variety of methodologies. These methodologies include: (a) x-ray crystallography; (b) nuclear magnetic resonance (NMR) spectroscopy; (c) molecular modeling methods, e.g., homology modeling techniques, threading algorithms, and in particular the refined homology modeling methods described below in Example 9.

Any available method can be used to construct a 3-D model of the Botulinum active site from the x-ray crystallographic, molecular modeling, and/or NMR data using a computer as described above. Such a model can be constructed from analytical data points inputted into the computer by an input device and by means of a processor using known software packages, e.g., CATALYST (Accelrys), INSIGHT (Accelrys) and CeriusII, HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

Figure 16:
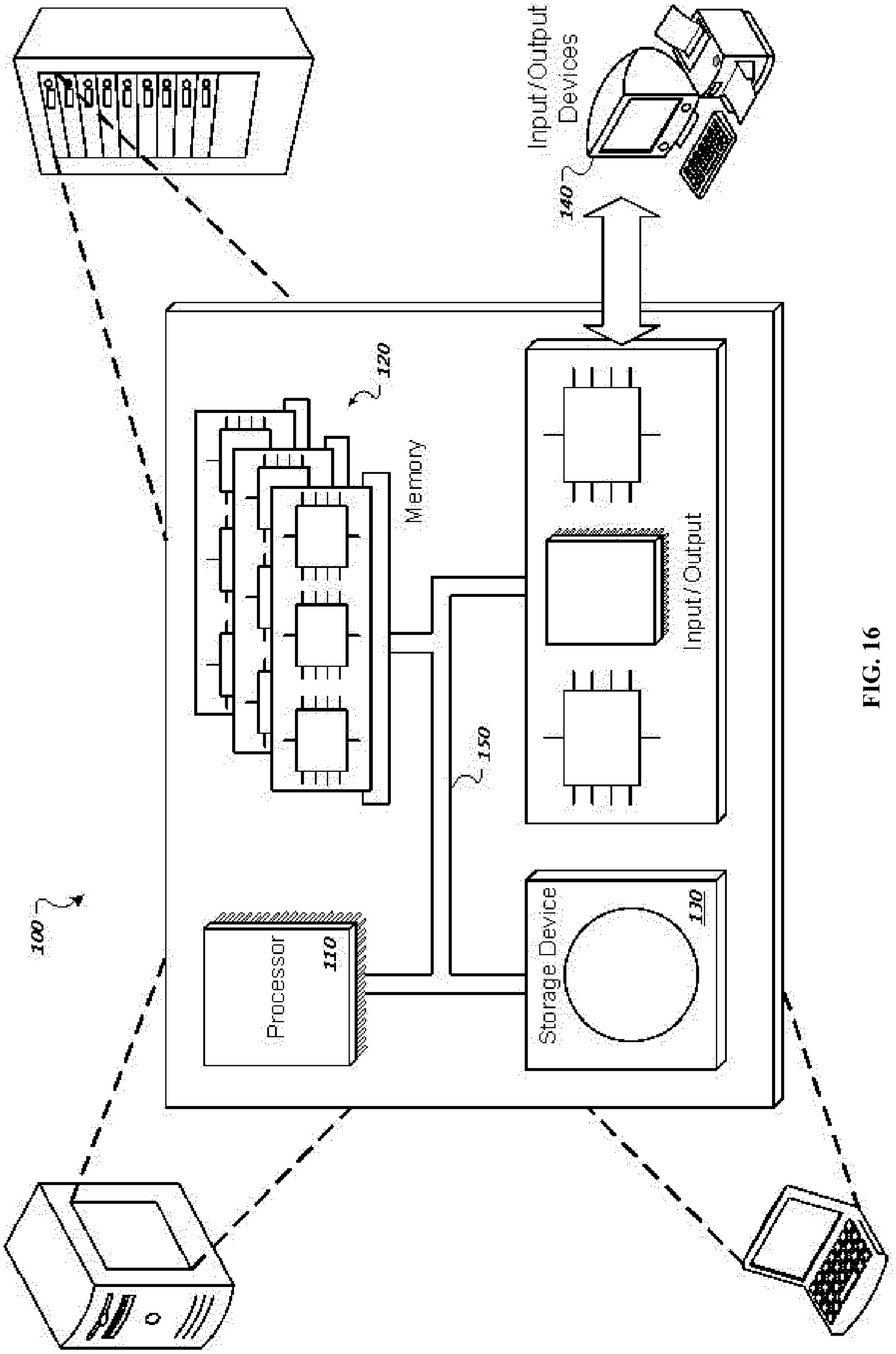
FIG. 16 is a block diagram of a computing system that can be used in connection with the data models and computer-implemented methods described in this document.

FIG. 16 is a schematic diagram of a computer system 100. The system 100 can be used for the operations described in association with any of the computer-implement methods described previously, according to one embodiment. The system 100 is intended to include various forms of digital computers, such as laptops, desktops, workstations, personal digital assistants, servers, blade servers, mainframes, and other appropriate computers. The system 100 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 100 includes a processor 110, a memory 120, a storage device 130, and an input/output device 140. Each of the components 110, 120, 130, and 140 are interconnected using a system bus 150. The processor 110 is capable of processing instructions for execution within the system 100. The processor may be designed using any of a number of architectures. For example, the processor 110 may be a CISC (Complex Instruction Set Computers) processor, a RISC (Reduced Instruction Set Computer) processor, or a MISC (Minimal Instruction Set Computer) processor.

In one embodiment, the processor 110 is a single-threaded processor. In another embodiment, the processor 110 is a multi-threaded processor. The processor 110 is capable of processing instructions stored in the memory 120 or on the storage device 130 to display graphical information for a user interface on the input/output device 140. The memory 120 stores information within the system 100. In one embodiment, the memory 120 is a computer-readable medium. In one embodiment, the memory 120 is a volatile memory unit. In another embodiment, the memory 120 is a non-volatile memory unit.

The storage device 130 is capable of providing mass storage for the system 100. In one embodiment, the storage device 130 is a computer-readable medium. In various different embodiments, the storage device 130 may be a floppy disk device, a hard disk device, an optical disk device, or a tape device.

The input/output device 140 provides input/output operations for the system 100. In one embodiment, the input/output device 140 includes a keyboard and/or pointing device. In another embodiment, the input/output device 140 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Once the 3-D structure of a compound that binds to or interacts with one or more residues of the active site of the 3BOO structure has been established using any of the above methods, a compound that has substantially the same 3-D structure (or contains a domain that has substantially the same structure) as the identified compound can be made. In this context, "has substantially the same 3-D structure" means that the compound possesses a hydrogen bonding and hydrophobic character that is similar to the identified compound. In some cases, a compound having substantially the same 3-D structure as the identified compound can include a hydroxyl or alkyl moiety.

With the above described 3-D structural data in hand and knowing the chemical structure (e.g., amino acid sequence in the case of a protein) of the region of interest, those of skill in the art would know how to make compounds with the above-described properties. Moreover, one having ordinary skill in the art would know how to derivatize such compounds. Such methods include chemical synthetic methods and, in the case of proteins, recombinant methods.

While not essential, computer-based methods can be used to design the compounds of the invention. Appropriate computer programs include: InsightII (Accelrys), CATALYST (Accelrys), LUDI (Accelrys, San Diego, Calif.), Aladdin (Daylight Chemical Information Systems, Irvine, Calif.); and LEGEND [Nishibata et al. (1985) J. Med. Chem. 36(20): 2921-2928], as well as the methods described in the Examples below and the references cited therein.

The above methods can be used to identify small-molecule inhibitors of other Botulinum serotypes or zinc endopeptidases. In such embodiments, equivalent residues of the active site as described above could be utilized.

EXAMPLES

Example 1

Synthesis of E1f

E1f was synthesized according to the scheme shown in FIG. 1.

Ethyl 2-(2-bromo-5-(4-iodo-3-nitrobenzoyl)thiophen-3-yl)acetate (2)

To a solution of ethyl 2-(thiophen-3-yl)acetate (1, 20.30 g, 119.25 mmol) in THF (150 mL) was added NBS (21.23 g, 119.25 mmol) over a period of 5 hours at 0° C., and then the mixture was warmed up to room temperature, stirring continuously for 24 hours. The solvent was removed in vacuo, and the residue was dissolved in EtOAc (150 mL) and washed with brine (4×30 mL). The organic layer was dried over $MgSO_4$, filtered, and then concentrated in vacuo. MPLC purification (Hex/EtOAc 5:1) of the residue gave ethyl 2-(2-bromothiophen-3-yl)acetate as a colorless oil (24.00 g, 81%). $^1H$ NMR (400 MHz, $CDCl_3$) δ 7.23 (d, J=5.4 Hz, 1H), 6.93 (d, J=5.4 Hz, 1H), 4.17 (q, J=7.2 Hz, 2H), 3.61 (s, 2H), and 1.27 (t, J=7.2 Hz, 3H); $^{13}C$ NMR (100 MHz, $CDCl_3$) δ 170.37, 133.84, 128.90, 125.93, 111.78, 61.32, 35.30, and 14.43.

To a solution of ethyl 2-(2-bromothiophen-3-yl)acetate (24.00 g, 96.32 mmol) and 4-iodo-3-nitrobenzoyl chloride (30.00 g, 96.32 mmol) in anhydrous $CH_2Cl_2$ (100 mL) was added $AlCl_3$ (38.53 g, 288.96 mmol) over a period of 4 hours at room temperature. The resulting mixture was stirred for 2 days. The reaction mixture was slowly poured onto 200 g of ice and allowed to warm to room temperature. The aqueous phase was extracted with $Et_2O$ (4×30 mL), and the combined organic layer was dried over $MgSO_4$, filtered, and then concentrated in vacuo. MPLC purification (Hex:EtOAc/4:1) of the residue gave 2 as a light yellow solid (20.00 g, 40%). $^1H$ NMR (400 MHz, $CDCl_3$) δ 8.26 (d, J=2.0 Hz, 1H), 8.21 (d, J=8.2 Hz, 1H), 7.69 (dd, J=2.0, 8.2 Hz, 1H), 7.48 (s, 1H), 4.19 (q, J=7.2 Hz, 2H), 3.66 (s, 2H), and 1.28 (t, J=7.2 Hz, 3H); $^{13}C$ NMR (100 MHz, $CDCl_3$) δ 183.84, 169.61, 153.25, 142.83, 141.87, 138.32, 136.49, 135.94, 133.07, 125.69, 124.50, 91.79, 61.76, 35.20, and 14.42.

Benzyl 4-((4-(5-bromo-4-(2-ethoxy-2-oxoethyl)thiophene-2-carbonyl)-2-nitrophenyl)ethynyl)benzoate (3)

A solution of 2 (952 mg, 1.82 mmol), benzyl 4-ethynylbenzoate (472 mg, 2.00 mmol), $Pd(PPh_3)_2Cl_2$ (128 mg, 0.18 mmol), $K_2CO_3$ (250 mg, 1.81 mmol), and $Et_3N$ (238 mg, 2.36 mmol) in DMF (4 mL) was stirred for 24 hours at room temperature. Water (5 mL) was added to the mixture and then extracted with EtOAc (3×30 mL). The combined organic layer was washed with brine, dried over $MgSO_4$, and concentrated in vacuo. MPLC purification (Hex:EtOAc/5:1) of the residue gave 3 as a solid foam (600 mg, 52%). $^1H$ NMR (400 MHz, $CDCl_3$) δ 8.55 (s, 1H), 8.11-8.06 (m, 3H), 7.87 (d, J=8.0 Hz, 1H), 7.68 (d, J=8.0 Hz, 2H), 7.52 (s, 1H), 7.47-7.34 (m, 5H), 5.38 (s, 3H), 4.19 (q, J=7.2 Hz, 2H), 3.67 (s, 2H), and 1.28 (t, J=7.2 Hz, 3H); $^{13}C$ NMR (100 MHz, $CDCl_3$) δ 183.86, 169.64, 165.88, 149.62, 142.04, 137.57, 136.41, 135.95, 135.92, 135.39, 133.02, 132.40, 131.08, 130.02, 129.93, 128.91, 128.66, 128.55, 126.69, 125.60, 124.44, 122.06, 99.57, 84.06, 67.32, 61.77, 35.25, and 14.42.

Benzyl 4-(6-(5-bromo-4-(2-ethoxy-2-oxoethyl)thiophene-2-carbonyl)-1H-indol-2-yl)benzoate (4)

To a solution of 3 (450 mg, 0.71 mmol) in EtOAc (10 mL) was added stannous chloride dihydrate (642 mg, 2.84 mmol). The resulting mixture was refluxed for one hour under $N_2$. The reaction mixture was then poured onto ice (5 g), and basified with a saturated $NaHCO_3$ solution to pH 8. The white milky mixture was filtered through a Celite pad to remove tin oxides. The organic layer from the filtrate was dried over $MgSO_4$, filtered, and then concentrated in vacuo. MPLC purification (Hex:EtOAc/4:1) of the crude product gave the desired intermediate benzyl 4-((2-amino-4-(5-bromo-4-(2-ethoxy-2-oxoethyl)thiophene-2-carbonyl)phenyl)ethynyl)benzoate as a yellow foam (450 mg, 95%). $^1H$ NMR (400 MHz, $CDCl_3$) δ 8.07 (d, J=8.0 Hz, 2H), 7.60 (d, J=8.0 Hz, 2H), 7.51-7.36 (m, 7H), 7.22-7.18 (m, 2H), 5.38 (s, 2H), 4.18 (q, J=7.2 Hz, 2H), 3.64 (s, 2H), and 1.27 (t, J=7.2 Hz, 3H); $^{13}C$ NMR (100 MHz, $CDCl_3$) δ 186.72, 169.84, 166.01, 148.31, 143.21, 138.58, 136.12, 136.05, 135.39, 132.55, 131.71, 130.02, 129.98, 128.90, 128.62, 128.51, 127.71, 122.93, 118.70, 114.66, 111.47, 96.66, 88.41, 67.21, 61.63, 53.75, 35.32, and 14.44.

To a 25 mL flask containing freshly distilled toluene (10 mL) was added benzyl 4-((2-amino-4-(5-bromo-4-(2- ethoxy-2-oxoethyl)thiophene-2-carbonyl)phenyl)ethynyl) benzoate (100 mg, 0.17 mmol) and indium tribromide (24 mg, 0.06 mmol) under $N_2$. The resulting mixture was refluxed for one hour. The solvent was removed in vacuo. MPLC purification (Hex:EtOAc/4:1) of the crude product gave 4 as a yellow solid (76 mg, 76%). $^1$H NMR (400 MHz, $CDCl_3$) δ 9.50 (brs, 1H), 8.16 (d, J=8.0 Hz, 2H), 8.02 (s, 1H), 7.82 (d, J=8.4 Hz, 2H), 7.65 (q, J=8.4 Hz, 2H), 7.55 (s, 1H), 7.48-7.34 (m, 5H), 6.98 (s, 1H), 5.39 (s, 2H), 4.19 (q, J=7.2 Hz, 2H), 3.64 (s, 2H), and 1.28 (t, J=7.2 Hz, 3H); $^{13}$C NMR (100 MHz, $CDCl_3$) δ 187.53, 170.09, 166.24, 143.98, 140.75, 136.91, 136.16, 136.07, 135.92, 135.09, 132.96, 131.53, 130.74, 129.74, 128.90, 128.59, 128.53, 125.56, 122.10, 121.94, 120.81, 113.74, 101.86, 67.14, 61.66, 35.37, and 14.43.

Benzyl 4-(6-(5-bromo-4-(2-ethoxy-2-oxoethyl) thiophene-2-carbonyl)-1-(4-(1,3-dioxoisoindolin-2-yl)butyl)-1H-indol-2-yl)benzoate (5)

To a stirred solution of 4 (76 mg, 0.13 mmol), N-(4-bromobutyl)-phthalimide (71 mg, 0.25 mmol) in 10 mL $CH_3CN$, CsF (96 mg, 0.63 mmol) was added. The resulting mixture was refluxed for 5 hours and then concentrated in vacuo. MPLC purification (Hex:EtOAc/4:1) of the residue gave 5 as a yellow amorphous solid (60 mg, 69%). $^1$H NMR (400 MHZ, $CDCl_3$) δ 8.13 (d, J=8.4 Hz, 2H), 7.96 (s, 1H), 7.74-7.35 (m, 14H), 6.62 (s, 1H), 5.39 (s, 2H), 4.30 (t, J=7.2 Hz, 2H), 4.16 (q, J=7.2 Hz, 2H), 3.66 (s, 2H), 3.49 (t, J=6.8 Hz, 2H), 1.70-1.66 (m, 2H), 1.48-1.45 (m, 2H), and 1.26 (t, J=7.2 Hz, 3H); $^{13}$C NMR (100 MHz, $CDCl_3$) δ 187.27, 169.94, 168.47, 166.11, 144.12, 143.76, 137.30, 137.13, 136.11, 135.81, 135.11, 134.22, 132.06, 131.88, 131.24, 130.37, 130.20, 129.31, 128.90, 128.61, 128.53, 123.43, 121.63, 120.86, 112.60, 104.17, 67.17, 61.49, 43.90, 37.22, 35.32, 27.38, 25.80, and 14.43.

Benzyl 4-(1-(4-(1,3-dioxoisoindolin-2-yl)butyl)-6-(4-(2-ethoxy-2-oxoethyl)-5-(3-hydroxy phenyl) thiophene-2-carbonyl)-1H-indol-2-yl)benzoate (6)

A mixture of 5 (60 mg, 0.075 mmol), $Pd(PPh_3)_4$ (17 mg, 0.015 mmol), CsF (34 mg, 0.22 mmol), 3-hydroxyphenylboronic acid (16 mg, 0.12 mmol), and $H_2O$ (80 μL) in DME (8 mL) was degassed with $N_2$ for 10 min and then refluxed. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex:EtOAc/5:1) of the residue gave 6 as a yellow amorphous solid (50 mg, 82%). $^1$H NMR (400 MHz, $CDCl_3$) δ 8.13 (d, J=8.0 Hz, 2H), 8.04 (s, 1H), 7.74-7.61 (m, 7H), 7.56 (d, J=8.0 Hz, 2H), 7.49-7.26 (m, 6H), 7.13 (s, 1H), 7.03 (d, J=7.6 Hz, 1H), 6.92 (d, J=8.4 Hz, 1H), 6.63 (s, 1H), 5.40 (s, 2H), 4.32 (t, J=7.2 Hz, 2H), 4.16-4.06 (m, 2H), 3.72 (s, 2H), 3.51 (t, J=6.8 Hz, 2H), 1.72-1.69 (m, 2H), 1.49-1.46 (m, 2H), and 1.26 (t, J=7.2 Hz, 3H); $^{13}$C NMR (100 MHz, $CDCl_3$) δ 188.62, 171.45, 168.65, 166.21, 157.16, 149.47, 143.69, 141.59, 138.00, 137.26, 137.23, 136.09, 134.28, 131.99, 131.82, 130.66, 130.37, 130.33, 130.12, 129.33, 128.90, 128.62, 128.53, 123.49, 121.88, 121.13, 120.87, 116.54, 116.46, 112.82, 104.20, 67.20, 61.46, 43.92, 37.36, 34.81, 27.45, 25.84, and 14.42.

4-(1-(4-(1,3-Dioxoisoindolin-2-yl)butyl)-6-(4-(2-ethoxy-2-oxoethyl)-5-(3-hydroxyphenyl)thiophene-2-carbonyl)-1H-indol-2-yl)benzoic acid (7)

A mixture of 6 (50 mg, 0.061 mmol) and 10% Pd—C (20 mg) in MeOH (8 mL) and EtOAc (3 mL) was stirred under 1 atm $H_2$ atmosphere until no 6 was detected by TLC. The resulting solution was filtered and concentrated in vacuo to give 7 as a yellow amorphous solid (39 mg, 88%). $^1$H NMR (400 MHz, $CDCl_3$) δ 8.16 (d, J=8.4 Hz, 2H), 8.06 (s, 1H), 7.77-7.65 (m, 7H), 7.59 (d, J=8.0 Hz, 2H), 7.29 (t, J=8.0 Hz, 2H), 7.11 (s, 1H), 7.03 (d, J=7.6 Hz, 1H), 6.93 (d, J=8.0 Hz, 1H), 6.66 (s, 1H), 4.34 (brt, 2H), 4.15 (q, J=7.2 Hz, 2H), 3.72 (s, 2H), 3.52 (brt, 2H), 1.72-1.65 (m, 2H), 1.51-1.47 (m, 2H), and 1.24 (t, J=7.2 Hz, 3H); $^{13}$C NMR (100 MHz, $CDCl_3$) δ 188.63, 171.67, 170.53, 168.73, 157.13, 149.52, 143.65, 141.52, 137.98, 137.73, 137.34, 134.34, 134.25, 131.97, 131.89, 131.84, 130.82, 130.56, 130.40, 129.55, 129.37, 123.54, 121.93, 121.17, 120.89, 116.52, 116.44, 112.83, 104.34, 61.59, 43.97, 37.38, 34.90, 27.46, 25.84, and 14.40.

Ethyl 2-(5-(2-(4-(bis(6-(1,3-dioxoisoindolin-2-yl) hexyl)carbamoyl)phenyl)-1-(4-(1,3-dioxoisoindolin-2-yl)butyl)-1H-indole-6-carbonyl)-2-(3-hydroxyphenyl)thiophen-3-yl)acetate (8)

A mixture of 7 (39 mg, 0.054 mmol), BOP (31 mg, 0.070 mmol), NMM (7 mg, 0.070 mmol), and 2,2'-(6,6'-azanediyl-bis(hexane-6,1-diyl))diisoindoline-1,3-dione (12) (38 mg, 0.080 mmol) in DMF (4 mL) was stirred at room temperature under $N_2$. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex/EtOAc 5:1) of the residue gave 8 as a yellow amorphous solid (39 mg, 61%). $^1$H NMR (400 MHz, $CDCl_3$) δ 8.00 (s, 1H), 7.80-7.61 (m, 15H), 7.52 (d, J=8.0 Hz, 2H), 7.45 (d, J=8.0 Hz, 2H), 7.28-7.24 (m, 1H), 7.06 (s, 1H), 6.99 (d, J=7.2 Hz, 1H), 6.91 (d, J=8.0 Hz, 1H), 6.58 (s, 1H), 4.29 (brt, 2H), 4.11 (q, J=7.2 Hz, 2H), 3.69-3.45 (m, 10H), 3.24 (brt, 2H), and 1.80-1.20 (m, 23H); $^{13}$C NMR (100 MHz, $CDCl_3$) δ 188.32, 171.38, 171.29, 168.70, 168.63, 168.57, 157.40, 149.20, 144.08, 141.64, 137.68, 137.24, 136.98, 134.31, 134.20, 134.14, 133.51, 132.32, 132.23, 132.04, 131.81, 131.64, 130.60, 130.21, 129.55, 127.24, 123.46, 123.39, 121.74, 120.94, 120.62, 116.55, 116.41, 112.69, 103.65, 61.35, 49.31, 45.04, 43.81, 38.11, 37.89, 37.36, 34.77, 30.84, 29.92, 28.74, 28.56, 27.60, 27.50, 26.86, 26.54, 26.28, 25.86, 19.34, and 14.40.

4-(1-(4-aminobutyl)-6-((4-(2-(hydroxyamino)-2-oxoethyl)-5-(3-hydroxyphenyl)thiophen-2-yl)(hydroxyimino)methyl)-1H-indol-2-yl)-N,N-bis(6-aminohexyl)benzamide (E1f)

To a stirred solution of 8 (39 mg, 0.033 mmol) in THF/MeOH (3 mL/3 mL), 3 mL of 50% aqueous $NH_2OH$ was added, followed by catalytic amount of KCN. The resulting mixture was stirred for 48 hours at room temperature, and then filtered through a short Celite column. HPLC purification of the filtrate gave E1f•$(TFA)_3$ as a yellow amorphous solid (15 mg, 41%). HPLC purification conditions: Agilent ZORBAX RX-C18 5 mm, 4.6×250 mm, eluting with linear gradient of 80% of solution A (1000 mL of $H_2O$ and 1 mL of TFA) to 100% of solution B (100 mL of $H_2O$, 900 mL of $CH_3CN$, and 1 mL of TFA) over 120 minutes, and flow rate of 1.0 mL/min with a retention time of 21.93 minutes for E1f•$(TFA)_3$. $^1$H NMR (400 MHz, $CD_3OD$) δ 7.69-7.63 (m, 4H), 7.52 (d, J=8.0 Hz, 2H), 7.30-7.26 (m, 2H), 7.19 (s, 1H), 6.97 (d, J=7.6 Hz, 1H), 6.94 (s, 1H), 6.84 (d, J=7.2 Hz, 1H), 6.66 (s, 1H), 4.35 (brt, 2H), 3.55 (brt, 2H), 3.43 (s, 2H), 3.40 (brt, 2H), 2.95 (t, J=7.2 Hz, 2H), 2.85 (t, J=7.2 Hz, 2H), 2.75 (t, J=7.2 Hz, 2H), and 1.74-1.20 (m, 20H); $^{13}$C NMR (100 MHz, $CD_3OD$) δ 172.34, 169.47, 157.78, 152.25, 145.46, 141.54, 137.79, 136.56, 134.82, 134.56, 134.41, 131.25, 130.12, 129.81, 129.38, 129.06, 128.47, 126.90, 121.42, 120.39, 120.35, 115.95, 115.87, 115.14, 111.64, 103.16, 49.25, 48.66, 44.91, 43.22, 39.45, 39.34, 39.14, 32.02, 28.37, 27.35, 27.27, 27.10, 26.33, 25.98, 25.82, and 24.63.

2-(6-bromohexyl)isoindoline-1,3-dione (10)

To a stirred solution of 1,6-dibromohexane (9) (16.5 g, 67.5 mmol) in acetone (100 mL) was added potassium phthalimide (5.00 g, 27.0 mmol). The resulting mixture was refluxed for 24 hours. The reaction mixture was cooled to room temperature and the solvent was removed in vacuo. MPLC purification of the residue (Hexanes:EtOAc/70:30) gave 10 as a colorless oily liquid (6.3 g, 75%). $^1$H NMR (400 MHz, $CDCl_3$) δ 7.85-7.83 (m, 2H), 7.72-7.70 (m, 2H), 3.68 (t, J=7.2 Hz, 2H), 3.39 (t, J=6.8 Hz, 2H), 1.89-1.82 (m, 2H), 1.73-1.66 (m, 2H), 1.52-1.45 (m, 2H), and 1.41-1.33 (m, 2H).

2,2'-(6,6'-(benzylazanediyl)bis(hexane-1,6-diyl)) didioindoline-1,3-dione (11)

To a stirred solution of 10 (6.5 g, 21.0 mmol) in acetonitrile (200 mL) was added $K_2CO_3$ (5.5 g, 39.9 mmol) and benzyl amine (1.07 g, 10.0 mmol). The resulting solution was refluxed for 48 hours. The reaction mixture was cooled to room temperature, filtered and the filtrate was concentrated in vacuo. MPLC purification (Hexanes:EtOAc/70:30) of the residue gave 11 as a yellow viscous oil (4.8 g, 85%). $^1$H NMR (400 MHz, $CDCl_3$) δ 7.76-7.74 (m, 4H), 7.65-7.62 (m, 4H), 7.24-7.11 (m, 5H), 3.58 (t, J=7.2 Hz, 4H), 3.44 (s, 2H), 2.30 (t, J=7.2 Hz, 4H), 1.64-1.54 (m, 4H), 1.44-1.34 (m, 4H), and 1.22-1.30 (m, 8H).

2,2'-(6,6'-azanediylbis(hexane-1,6-diyl))didioindoline-1,3-dione (12)

To a stirred solution of 11 (1.5 g, 2.6 mmol) in MeOH: EtOAc (1:1, 40 mL) was added 10% Pd—C (0.15 g). The resulting mixture was stirred at room temperature for 16 hours under a hydrogen balloon. The reaction mixture was filtered off and the filtrate was concentrated in vacuo. MPLC purification of the residue gave 12 as an amorphous white solid (0.98 g, 78%). $^1$H NMR (400 MHz, $CD_3OD$) δ 7.85-7.78 (m, 8H), 3.68 (t, J=7.2 Hz, 4H), 2.89 (t, J=7.8 Hz, 4H), 1.80-1.60 (m, 8H), and 1.50-1.30 (m, 8H).

Example 2

Synthesis of E2

Figure 2:
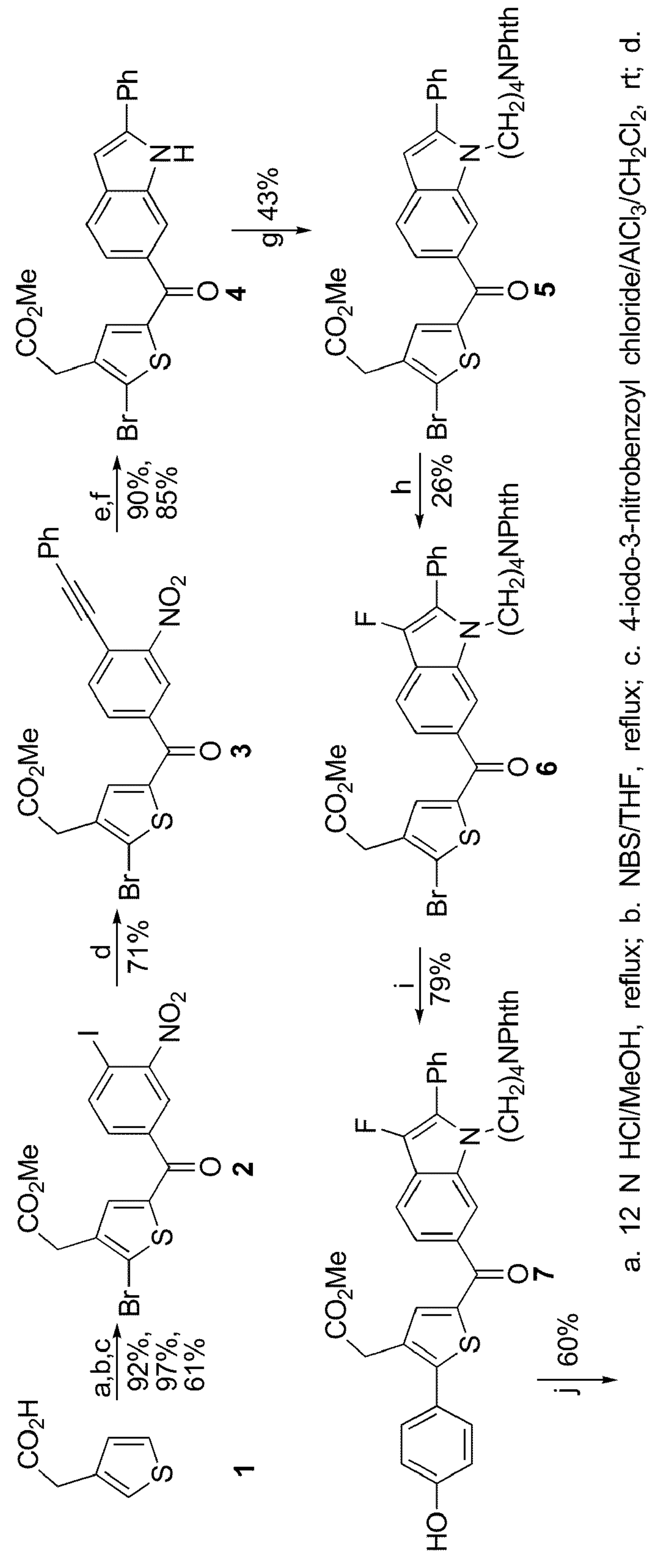
FIG. 2 is a scheme illustrating a synthesis of E2.

E2 was synthesized according to the scheme in FIG. 2.

Methyl 2-(2-bromo-5-(4-iodo-3-nitrobenzoyl) thiophen-3-yl)acetate (2)

To a stirred solution of 2-(thiophen-3-yl)acetic acid (9, 28.00 g, 196.94 mmol) in methanol (300 mL) was added 12 N HCl (15 mL) and the mixture refluxed for two hours. Methanol was removed by evaporation in vacuo, the residue was dissolved in dichloromethane, washed with saturated $NaHCO_3$ solution, dried over $MgSO_4$, filtered, and concentrated. Kugelrohr distillation of the crude product at 90° C. per 0.1 mmHg gave the desired ester as a colorless oil (28.43 g, 92%). $^1$H NMR (400 MHz, $CDCl_3$) δ 7.29 (dd, J=2.0, 4.9 Hz, 1H), 7.20 (m, 1H), 7.04 (dd, J=1.2, 4.9 Hz, 1H), 3.71 (s, 3H), and 3.67 (s, 2H).

To a solution of the above ester (10.00 g, 64.02 mmol) in THF (100 mL) was added NBS (11.40 g, 64.02 mmol). The resulting mixture was refluxed for two and a half hours. The solvent was removed in vacuo. MPLC purification (Hex: EtOAc/9:1) of the residue gave methyl 2-(2-bromothiophen-3-yl)acetate as a colorless oil (14.55 g, 97%). $^1$H NMR (400 MHz, $CDCl_3$) δ 7.25 (d, J=5.6 Hz, 1H). 6.93 (d, J=5.6 Hz, 1H), 3.72 (s, 3H), and 3.64 (s, 2H).

To a stirred solution of methyl (2-bromothiophen-3-yl) acetate (120 mg, 0.51 mmol) and 4-iodo-3-nitrobenzoyl chloride (150 mg, 0.48 mmol) in anhydrous $CH_2Cl_2$ (10 mL) was added $AlCl_3$ (260 mg, 1.95 mmol) in four portions in 10-minute intervals at room temperature. The resulting mixture was stirred overnight. The reaction mixture was slowly poured onto 5 g of ice and allowed to warm to room temperature. The aqueous phase was extracted with $CH_2Cl_2$ (3×15 mL). The combined organic layer was dried over $MgSO_4$, filtered, and then concentrated in vacuo. MPLC purification (Hex:EtOAc/5:1) of the residue gave 2 as a light yellow solid (158 mg, 61%). $^1$H NMR (400 MHz, $CDCl_3$) δ 8.27 (d, J=2.0 Hz, 1H), 8.22 (d, J=8.0 Hz, 1H), 7.70 (dd, J=2.0, 8.2 Hz, 1H), 7.48 (s, 1H), 3.74 (s, 3H), and 3.68 (s, 2H); $^{13}$C NMR (100 MHz, $CDCl_3$) δ 183.8, 170.0, 153.2, 142.9, 141.9, 138.3, 136.5, 135.8, 133.1, 125.7, 124.5, 91.8, 52.6, and 35.0.

Methyl 2-(2-bromo-5-(3-nitro-4-(phenylethynyl) benzoyl)thiophen-3-yl)acetate (3)

A solution of 2 (150 mg, 0.29 mmol), phenylacetylene (32 μL, 0.29 mmol), $Pd(PPh_3)_2Cl_2$ (21 mg, 0.03 mmol), $K_2CO_3$ (42 mg, 0.29 mmol), and $Et_3N$ (40 μL, 0.29 mmol) in DMF (3 mL) was stirred for 24 hours at room temperature. Water (5 mL) was added to the mixture and then extracted with EtOAc (3×10 mL). The combined organic layer was washed with brine, dried over $MgSO_4$, and concentrated in vacuo. MPLC purification (Hex:EtOAc/5:1) of the residue gave 3 as a solid foam (101 mg, 71%). $^1$H NMR (400 MHz, $CDCl_3$) δ 8.54 (d, J=1.6 Hz, 1H), 8.06 (dd, J=1.6, 8.0 Hz, 1H), 7.86 (d, J=8.4 Hz, 1H), 7.64 (m, 2H), 7.52 (s, 1H), 7.42 (m, 3H), 3.75 (s, 3H), and 3.70 (s, 2H); $^{13}$C NMR (100 MHz, $CDCl_3$) δ 183.9, 170.1, 149.5, 142.2, 137.0, 136.3, 135.7, 135.3, 132.9, 132.5, 130.1, 128.8, 125.6, 124.3, 122.8, 122.1, 101.1, 84.7, 52.7, and 35.0.

Methyl (2-bromo-5-(2-phenyl-1H-indole-6-carbonyl) thiophen-3-yl)acetate (4)

To a solution of 3 (25 mg, 0.05 mmol) in EtOAc (5 mL) was added stannous chloride dihydrate (58 mg, 0.26 mmol). The resulting mixture was refluxed for one hour under $N_2$. The reaction mixture was poured onto ice (5 g), and basified with a saturated $NaHCO_3$ solution to pH 8. The white milky mixture was filtered through a Celite pad to remove tin oxides. The organic layer from the filtrate was dried over $MgSO_4$, filtered, and then concentrated in vacuo. MPLC purification (Hex:EtOAc/4:1) of the crude product gave the desired intermediate methyl (2-bromo-5-(3-amino-4-(phenylethynyl) benzoyl)thiophen-3-yl)acetate as a yellow foam (21 mg, 90%). $^1$H NMR (400 MHz, $CDCl_3$) δ 7.55 (m, 2H), 7.50 (s, 1H), 7.48 (d, J=1.6 Hz, 1H), 7.38 (m, 3H), 7.17 (m, 2H), 4.40 (brs, 2H), 3.73 (s, 3H), and 3.66 (s, 2H); $^{13}$C NMR (100 MHz, $CDCl_3$) δ 186.7, 170.3, 148.1, 143.4, 138.1, 135.9, 135.1, 132.4, 131.8, 129.0, 128.7, 122.9, 122.8, 118.8, 114.5, 112.3, 97.6, 85.3, 52.6, and 35.0; HRMS-ESI calcd $C_{22}H_{16}BrNO_3S$

[M+Na] 475.9926. found 475.9923. To a 250 mL flask containing freshly distilled toluene (50 mL) was added methyl (2-bromo-5-(3-amino-4-(phenylethynyl)benzoyl)thiophen-3-yl)acetate (2.93 g, 6.45 mmol) and indium tribromide (1.14 g, 3.22 mmol) under $N_2$. The resulting mixture was refluxed for one hour. The solvent was removed in vacuo. MPLC purification (Hex:EtOAc/4:1) of the crude product gave 4 as a yellow solid (2.50 g, 85%). $^1$H NMR (400 MHz, $CDCl_3$) δ 9.38 (brs, 1H), 7.98 (s, 1H), 7.69 (d, J=7.8 Hz, 2H), 7.58 (m, 2H), 7.47 (s, 1H), 7.40 (t, J=7.5 Hz, 2H), 7.30 (m, 1H), 6.80 (s, 1H), 3.65 (s, 3H), and 3.59 (s, 2H); $^{13}$C NMR (100 MHz, $CDCl_3$) δ 187.4, 170.5, 144.2, 142.3, 136.5, 135.7, 134.9, 133.3, 131.8, 130.9, 129.4, 128.8, 125.9, 121.9, 120.4, 113.5, 100.3, 52.6, and 35.2.

Methyl 2-(2-bromo-5-(1-(4-(1,3-dioxoisoindolin-2-yl)butyl)-2-phenyl-1H-indole-6-carbonyl)-thiophene-3-yl)acetate (5)

To a stirred solution of 4 (45 mg, 0.10 mmol) in anhydrous $CH_3CN$ (5 mL) was added CsF-Celite (125 mg) under $N_2$, followed by addition of N-(4-bromobutyl)-phthalimide (28 mg, 0.10 mmol). The resulting mixture was refluxed for five hours, cooled to room temperature, and filtered. The filtrate was evaporated in vacuo. MPLC purification (Hex:EtOAc/4:1) of the residue gave 5 as a yellow solid (28 mg, 43%). $^1$H NMR (400 MHz, $CDCl_3$) δ 7.98 (s, 1H), 7.74 (m, 6H), 7.59 (s, 1H), 7.47 (m, 5H), 6.60 (s, 1H), 4.32 (t, J=7.2 Hz, 2H), 3.73 (s, 3H), 3.71 (s, 2H), 3.52 (t, J=6.8 Hz, 2H), 1.72 (m, 2H), and 1.51 (m, 2H); $^{13}$C NMR (100 MHz, $CDCl_3$) δ 187.3, 170.4, 168.5, 145.2, 144.3, 136.8, 135.6, 134.9, 134.2, 134.1, 132.5, 132.1, 130.7, 129.5, 129.0, 128.8, 123.5, 123.4, 121.5, 120.6, 112.5, 103.1, 52.5, 43.7, 37.3, 35.1, 27.4, and 25.8.

Methyl 2-(2-bromo-5-(1-(4-(1,3-dioxoisoindolin-2-yl)butyl)-3-fluoro-2-phenyl-1H-indole-6-carbonyl) thiophen-3-yl)acetate (6)

To a solution of 5 (170 mg, 0.25 mmol) in 3 mL $CH_2Cl_2$ was added 1-fluoropyridinium triflate (75 mg, 0.30 mmol), and then the mixture was stirred at room temperature until no 5 was detected by NMR. The resulting mixture was diluted with 40 mL $Et_2O$, washed with brine (2×10 mL), dried over $MgSO_4$, filtered, and then concentrated in vacuo. MPLC purification (Hex:EtOAc/9:1) gave 6 (45 mg, 26%) as a yellow amorphous solid. $^1$H NMR (400 MHz, $CDCl_3$) δ 7.94 (s, 1H), 7.78-7.63 (m, 6H), 7.56 (s, 1H), 7.50-7.41 (m, 5H), 4.25 (t, J=7.2 Hz, 2H), 3.71 (s, 3H), 3.69 (s, 2H), 3.49 (t, J=6.8 Hz, 2H), 1.66-1.60 (m, 2H), and 1.50-1.45 (m, 2H); $^{13}$C NMR (100 MHz, $CDCl_3$) δ 186.88, 170.13, 168.24, 143.76, 142.84, 140.39, 135.53, 134.70, 133.95, 133.90, 132.08, 132.02, 131.85, 131.39, 129.70, 128.91, 128.87, 128.72, 128.21, 128.18, 127.32, 127.12, 123.20, 121.58, 120.91, 119.94, 119.78, 116.78, 116.76, 112.32, 52.30, 43.37, 36.95, 34.81, 27.06, and 25.51.

Methyl 2-(5-(1-(4-(1,3-dioxoisoindolin-2-yl)butyl)-3-fluoro-2-phenyl-1H-indole-6-carbonyl)-2-(4-hydroxyphenyl)thiophen-3-yl) (7)

A mixture of 6 (42 mg, 0.062 mmol), $Pd(PPh_3)_4$ (8 mg, 0.007 mmol), CsF (28 mg, 0.18 mmol), 4-hydroxyphenylboronic acid (13 mg, 0.094 mmol), and $H_2O$ (80 μL) in DME (8 mL) was degassed with $N_2$ for 10 minutes and then refluxed. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex:EtOAc/5:1) of the residue gave 7 as a yellow amorphous solid (34 mg, 79%). $^1$H NMR (400 MHz, $CDCl_3$) δ 8.00 (s, 1H), 7.78-7.66 (m, 7H), 7.50-7.34 (m, 7H), 6.95 (d, J=8.4 Hz, 2H), 6.88 (s, 1H), 4.25 (t, J=7.2 Hz, 2H), 3.69 (brs, 5H), 3.48 (t, J=6.8 Hz, 2H), 1.66-1.59 (m, 2H), and 1.50-1.44 (m, 2H); $^{13}$C NMR (100 MHz, $CDCl_3$) δ 188.44, 171.91, 168.60, 157.32, 150.06, 143.16, 141.19, 140.71, 137.93, 134.25, 132.39, 132.37, 132.08, 130.96, 129.97, 129.17, 129.09, 128.58, 128.54, 127.40, 127.20, 125.03, 123.50, 121.42, 120.07, 119.92, 116.93, 116.21, 112.67, 52.54, 43.61, 37.28, 34.49, 27.35, and 25.77.

2-(5-(1-(4-Aminobutyl)-3-fluoro-2-phenyl-1H-indole-6-carbonyl)-2-(4-hydroxyphenyl)thiophen-3-yl)-N-hydroxyacetamide (E2)

To a stirred solution of 7 (34 mg, 0.049 mmol) in THF/MeOH (1 mL/3 mL), 1 mL of 50% aqueous $NH_2OH$ was added, followed by a catalytic amount of KCN. The resulting mixture was stirred overnight at room temperature, and then filtered through a short Celite column. HPLC purification of the filtrate gave E2•TFA as a yellow amorphous solid (19 mg, 54%). HPLC purification conditions: Agilent ZORBAX RX-C18 5 mm, 4.6×250 mm, eluting with linear gradient of 80% of solution A (1000 mL of $H_2O$ and 1 mL of TFA) to 100% of solution B (100 mL of $H_2O$, 900 mL of $CH_3CN$, and 1 mL of TFA) over 20 minutes, and flow rate of 1.0 mL/min with a retention time of 14.36 minutes for E2•TFA. $^1$H NMR (400 MHz, $CD_3OD$) δ 8.11 (s, 1H), 7.78 (s, 1H), 7.73 (d, J=8.4 Hz, 1H), 7.66 (d, J=8.4 Hz, 1H), 7.59-7.51 (m, 5H), 7.39 (d, J=8.4 Hz, 2H), 6.92 (d, J=8.8 Hz, 2H), 4.36 (t, J=7.2 Hz, 2H), 3.51 (s, 2H), 2.79 (t, J=7.2 Hz, 2H), 1.76-1.69 (m, 2H), and 1.50-1.43 (m, 2H); $^{13}$C NMR (100 MHz, $CD_3OD$) δ 188.80, 169.26, 158.74, 150.11, 142.96, 140.72, 140.53, 137.85, 132.22, 132.17, 132.12, 130.73, 130.53, 129.85, 129.02, 128.96, 128.47, 128.43, 127.40, 127.20, 123.86, 120.58, 119.72, 119.56, 116.65, 115.71, 113.10, 43.29, 39.18, 32.29, 27.11, and 24.70.

Example 3

Synthesis of E3

Figure 3:
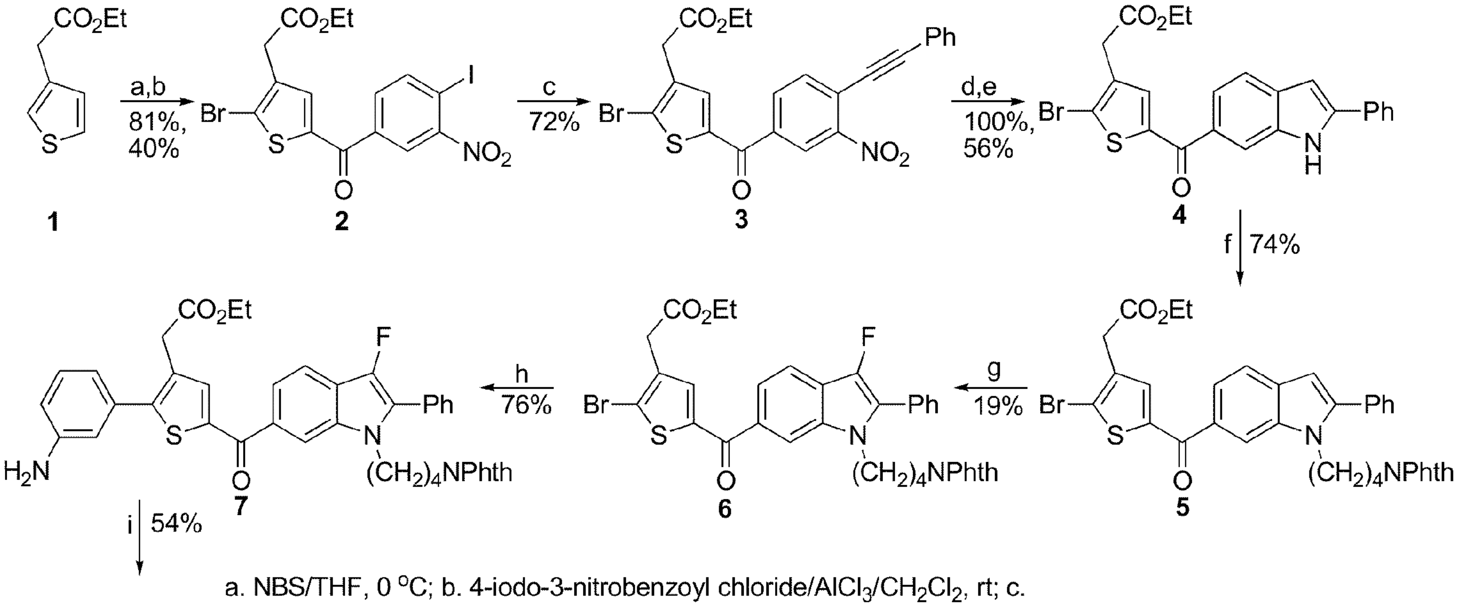
FIG. 3 is a scheme illustrating a synthesis of E3.

E3 was synthesized according to the scheme in FIG. 3.

Ethyl 2-(2-bromo-5-(4-iodo-3-nitrobenzoyl) thiophen-3-yl)acetate (2)

To a solution of ethyl 2-(thiophen-3-yl)acetate (20.30 g, 119.25 mmol) in THF (150 mL) was added NBS (21.23 g, 119.25 mmol) during a period of 5 hours at 0° C., and then the mixture was warmed up to room temperature, stirring continuously for 24 hours. The solvent was removed in vacuo, and then the residue as dissolved in EtOAc (150 mL) and washed with brine (4×30 mL). The organic layer was dried over $MgSO_4$, filtered, and then concentrated in vacuo. MPLC purification (Hex:EtOAc/5:1) of the residue gave ethyl 2-(2-bromothiophen-3-yl)acetate as a colorless oil (24.00 g, 81%). $^1$H NMR (400 MHz, $CDCl_3$) δ 7.23 (d, J=5.4 Hz, 1H), 6.93 (d, J=5.4 Hz, 1H), 4.17 (q, J=7.2 Hz, 2H), 3.61 (s, 2H), and 1.27 (t, J=7.2 Hz, 3H); $^{13}$C NMR (100 MHz, $CDCl_3$) δ 170.37, 133.84, 128.90, 125.93, 111.78, 61.32, 35.30, and 14.43. To a solution of ethyl 2-(2-bromothiophen-3-yl)acetate (24.00 g, 96.32 mmol) and 4-iodo-3-nitrobenzoyl chloride (30.00 g, 96.32 mmol) in anhydrous $CH_2Cl_2$ (100 mL) was added $AlCl_3$ (38.53 g, 288.96 mmol) over a period of 4 hours at room temperature. The resulting mixture was stirred for 2 days. The reaction mixture was slowly poured onto 200 g of ice and allowed to warm to room temperature. The aqueous phase was extracted with $Et_2O$ (4×30 mL), and the combined organic layer was dried over $MgSO_4$, filtered, and then concentrated in vacuo. MPLC purification of (Hex:EtOAc/4:1) of the residue gave 2 as a light yellow solid (20.00 g, 40%). $^1$H NMR (400 MHz, $CDCl_3$) δ 8.26 (d, J=2.0 Hz, 1H), 8.21 (d, J=8.2 Hz, 1H), 7.69 (dd, J=2.0, 8.2 Hz, 1H), 7.48 (s, 1H), 4.19 (q, J=7.2 Hz, 2H), 3.66 (s, 2H), and 1.28 (t, J=7.2 Hz, 3H); $^{13}$C NMR (100 MHz, $CDCl_3$) δ 183.84, 169.61, 153.25, 142.83, 141.87, 138.32, 136.49, 135.94, 133.07, 125.69, 124.50, 91.79, 61.76, 35.20, and 14.42.

Ethyl 2-(2-bromo-5-(3-nitro-4-(phenylethynyl)benzoyl)thiophen-3-yl)acetate (3)

A solution of 2 (2.00 g, 3.82 mmol), phenylacetylene (0.47 mL, 4.28 mmol), $Pd(PPh_3)_2Cl_2$ (137 mg, 0.19 mmol), $K_2CO_3$ (542 mg, 3.92 mmol), and $Et_3N$ (0.55 mL, 3.95 mmol) in DMF (5 mL) was stirred for 24 h at room temperature. Water (10 mL) was added to the mixture and then extracted with $Et_2O$ (3×30 mL). The combined organic layer was washed with brine (3×15 mL), dried over $MgSO_4$, and then concentrated in vacuo. MPLC purification (Hex:EtOAc/5:1) of the residue gave 3 as a yellow amorphous solid (1.37 g, 72%). $^1$H NMR (400 MHz, $CDCl_3$) δ 8.52 (s, 1H), 8.04 (d, J=8.0 Hz, 1H), 7.84 (d, J=8.0 Hz, 1H), 7.63-7.61 (m, 2H), 7.52 (s, 1H), 7.43-7.37 (m, 3H), 4.19 (q, J=7.2 Hz, 2H), 3.67 (s, 2H), and 1.28 (t, J=7.2 Hz, 3H); $^{13}$C NMR (100 MHz, $CDCl_3$) δ 183.93, 169.64, 149.51, 142.13, 136.97, 136.36, 135.90, 135.24, 132.92, 132.52, 130.11, 128.82, 125.57, 124.25, 122.73, 122.06, 101.10, 84.72, 61.75, 35.26, and 14.42.

Ethyl 2-(2-bromo-5-(2-phenyl-1H-indole-6-carbonyl)thiophen-3-yl)acetate (4)

To a solution of 3 (1.37 g, 2.75 mmol) in EtOAc (50 mL) was added stannous chloride dihydrate (2.5 g, 11.08 mmol). The resulting mixture was refluxed for 1 hour under $N_2$. The reaction mixture was poured into a saturated $NaHCO_3$ solution (50 mL) and extracted with EtOAc (150 mL). The organic layer was washed with aqueous $NaHCO_3$ solution (3×30 mL), dried over $MgSO_4$, filtered, and then concentrated in vacuo. MPLC purification (Hex/EtOAc 4:1) of the residue gave the desired intermediate ethyl (2-bromo-5-(3-amino-4-(phenylethynyl)benzoyl)-thiophen-3-yl)acetate as a yellow foam (1.28 g, 100%). To a 100 mL flask containing freshly distilled toluene (20 mL) were added ethyl (2-bromo-5-(3-amino-4-(phenylethynyl)benzoyl)thiophen-3-yl)acetate (1.28 g, 2.70 mmol) and indium tribromide (500 mg, 1.41 mmol) under $N_2$. The resulting mixture was refluxed for 12 hours. The solvent was removed in vacuo. MPLC purification (Hex:EtOAc/4:1) of the residue gave 4 as a yellow amorphous solid (454 mg, 56%). $^1$H NMR (400 MHz, $CDCl_3$) δ 8.88 (s, 1H), 8.02 (s, 1H), 7.74 (d, J=7.6 Hz, 2H), 7.70-7.64 (m, 2H), 7.56 (s, 1H), 7.49 (t, J=7.6 Hz, 2H), 7.40 (t, J=7.6 Hz, 1H), 6.90 (s, 1H), 4.19 (q, J=7.2 Hz, 2H), 3.66 (s, 2H), and 1.27 (t, J=7.2 Hz, 3H); $^{13}$C NMR (100 MHz, $CDCl_3$) δ 187.62, 170.13, 144.16, 142.47, 136.69, 135.86, 135.05, 133.38, 131.84, 130.69, 129.31, 128.77, 128.70, 125.92, 121.81, 120.27, 113.73, 100.08, 61.67, 35.43, and 14.44.

Ethyl 2-(2-bromo-5-(1-(4-(1,3-dioxoisoindolin-2-yl)butyl)-2-phenyl-1H-indole-6-car-bonyl)thiophen-3-yl)acetate (5)

To a stirred solution of 4 (715 mg, 1.53 mmol), N-(4-bromobutyl)-phthalimide (888 mg, 3.15 mmol) in 20 mL $CH_3CN$, CsF (1.24 g, 8.21 mmol) was added. The resulting mixture was refluxed for 5 hours and then concentrated in vacuo. MPLC purification (Hex:EtOAc/4:1) of the residue gave 5 as a yellow amorphous solid (666 mg, 74%). $^1$H NMR (400 MHz, $CDCl_3$) δ 7.96 (s, 1H), 7.78-7.65 (m, 6H), 7.58 (s, 1H), 7.48-7.39 (m, 5H), 6.57 (s, 1H), 4.30 (t, J=7.2 Hz, 2H), 4.16 (q, J=7.2 Hz, 2H), 3.67 (s, 2H), 3.49 (t, J=6.8 Hz, 2H), 1.74-1.68 (m, 2H), 1.50-1.46 (m, 2H), and 1.26 (t, J=7.2 Hz, 3H); $^{13}$C NMR (100 MHz, $CDCl_3$) δ 187.33, 169.95, 168.50, 145.22, 144.25, 136.85, 135.71, 135.07, 134.18, 132.55, 132.15, 132.09, 130.69, 129.52, 128.96, 128.84, 128.74, 123.44, 121.48, 121.42, 120.53, 112.50, 103.12, 61.49, 43.67, 37.26, 35.37, 27.38, 25.81, and 14.44.

Ethyl 2-(2-bromo-5-(1-(4-(1,3-dioxoisoindolin-2-yl)butyl)-3-fluoro-2-phenyl-1H-indole-6-carbonyl)thiophen-3-yl)acetate (6)

To a solution of 5 (209 mg, 0.31 mmol) in 3 mL $CH_2Cl_2$ was added 1-fluoropyridinium triflate (81 mg, 0.33 mmol), and then the mixture stirred at room temperature until no 5 was detected by NMR. The resulting mixture was diluted with 40 mL $Et_2O$, washed with brine (2×10 mL), dried over $MgSO_4$, filtered, and then concentrated in vacuo. MPLC purification (Hex/EtOAc 9:1) gave 6 (40 mg, 19%) as a yellow amorphous solid. $^1$H NMR (400 MHz, $CDCl_3$) δ 7.94 (s, 1H), 7.77-7.63 (m, 6H), 7.57 (s, 1H), 7.48-7.40 (m, 5H), 4.25 (t, J=7.2 Hz, 2H), 4.16 (q, J=7.2 Hz, 2H), 3.72 (s, 2H), 3.48 (t, J=6.8 Hz, 2H), 1.65-1.61 (m, 2H), 1.50-1.44 (m, 2H), and 1.26 (t, J=7.2 Hz, 3H); $^{13}$C NMR (100 MHz, $CDCl_3$) δ 187.16, 169.94, 168.50, 143.96, 143.10, 140.65, 135.88, 135.17, 134.22, 134.17, 132.37, 132.31, 132.11, 131.68, 129.96, 129.51, 129.17, 129.13, 128.96, 128.45, 127.58, 127.38, 123.46, 121.80, 121.19, 120.18, 120.03, 116.97, 112.58, 61.52, 43.64, 37.21, 35.33, 27.32, 25.76, and 14.44; 19F NMR (376 MHZ, $CDCl_3$) δ −174.33.

Ethyl 2-(2-(3-aminophenyl)-5-(1-(4-(1,3-dioxoisoindolin-2-yl)butyl)-3-fluoro-2-phenyl-1H-indole-6-carbonyl)thiophen-3-yl)acetate (7)

A mixture of 6 (40 mg, 0.058 mmol), $Pd(PPh_3)_4$ (13 mg, 0.011 mmol), CsF (27 mg, 0.18 mmol), 3-aminophenylboronic acid (12 mg, 0.088 mmol), and $H_2O$ (80 μL) in DME (8 mL) was degassed with $N_2$ for 10 minutes and then refluxed. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex:EtOAc/5:1) of the residue gave 7 as a yellow amorphous solid (31 mg, 76%). $^1$H NMR (400 MHz, $CDCl_3$) δ 8.00 (s, 1H), 7.78-7.67 (m, 7H), 7.51-7.41 (m, 5H), 7.23 (t, J=8.0 Hz, 1H), 6.90 (d, J=7.6 Hz, 1H), 6.85 (s, 1H), 6.73 (d, J=8.0 Hz, 1H), 4.26 (t, J=7.0 Hz, 2H), 4.15 (q, J=7.2 Hz, 2H), 3.82 (brs, 2H), 3.70 (s, 2H), 3.48 (t, J=6.8 Hz, 2H), 1.66-1.60 (m, 2H), 1.48-1.45 (m, 2H), and 1.25 (t, J=7.2 Hz, 3H); $^{13}$C NMR (100 MHz, $CDCl_3$) δ 188.13, 171.26, 168.49, 149.66, 147.09, 143.16, 141.68, 140.71, 137.58, 134.19, 132.51, 132.44, 132.38, 132.14, 130.54, 130.05, 129.97, 129.54, 129.15, 129.06, 128.94, 128.58, 127.31, 127.10, 123.47, 121.43, 120.02, 119.86, 119.71, 116.81, 115.88, 115.69, 112.56, 61.31, 43.61, 37.25, 34.77, 27.36, 25.77, and 14.45; 19F NMR (376 MHZ, $CDCl_3$) δ −174.49.

2-(5-(1-(4-aminobutyl)-3-fluoro-2-phenyl-1H-indole-6-carbonyl)-2-(3-aminophenyl)thiophen-3-yl)-N-hydroxyacetamide (E3)

To a stirred solution of 7 (31 mg, 0.044 mmol) in THF/MeOH (1 mL/3 mL), 1 mL of 50% aqueous $NH_2OH$ was added, followed by a catalytic amount of KCN. The resulting mixture was stirred overnight at room temperature, and then filtered through a short Celite column. HPLC purification of the filtrate gave E3•$(TFA)_2$ as a yellow amorphous solid (19 mg, 54%). HPLC purification conditions: Agilent ZORBAX RX-C18 5 mm, 4.6×250 mm, eluting with linear gradient of 80% of solution A (1000 mL of $H_2O$ and 1 mL of TFA) to 100% of solution B (100 mL of $H_2O$, 900 mL of $CH_3CN$, and 1 mL of TFA) over 20 minutes, and flow rate of 1.0 mL/min with a retention time of 12.07 minutes for E3•$(TFA)_2$. $^1H$ NMR (400 MHz, $CD_3OD$) δ 8.12 (s, 1H), 7.82 (s, 1H), 7.74 (d, J=8.4 Hz, 1H), 7.69 (d, J=8.4 Hz, 1H), 7.66-7.51 (m, 8H), 7.44-7.42 (m, 1H), 4.37 (t, J=6.8 Hz, 2H), 3.54 (s, 2H), 2.78 (t, J=7.2 Hz, 2H), 1.76-1.68 (m, 2H), and 1.49-1.41 (m, 2H); $^{13}C$ NMR (100 MHz, $CD_3OD$) δ 188.54, 168.75, 146.93, 142.94, 142.57, 140.51, 137.34, 134.87, 134.07, 132.54, 132.23, 132.17, 131.88, 130.72, 129.86, 129.08, 128.99, 128.39, 128.36, 128.29, 127.68, 127.47, 122.78, 122.46, 120.69, 119.91, 119.76, 117.67, 116.65, 114.79, 113.08, 43.28, 39.15, 32.28, 27.06, and 24.67.

Example 4

Synthesis of E4

E4 was synthesized according to the scheme in FIG. 4.

Methyl 1H-pyrrole-2-carboxylate (2)

To a stirred solution of 2-(trichloroacetyl)pyrrole (1) (10.00 g, 47.1 mmol) in MeOH (20 mL) was added $K_2CO_3$ (8.44 g, 61.2 mmol). The resulting mixture was stirred under reflux for 3 hours, cooled to room temperature and filtered. The filtrate was concentrated in vacuo to give 2 as a dark brown solid (5.50 g, 93%). $^1H$ NMR (400 MHz, $CDCl_3$) δ 9.49 (brs, 1H), 6.92-6.96 (m, 2H), 6.26 (m, 1H), and 3.86 (s, 3H); $^{13}C$ NMR (100 MHz, $CDCl_3$) δ 162.05, 123.33, 122.79, 115.56, 110.66, and 51.72.

Methyl 4-formyl-1H-pyrrole-2-carboxylate (3)

To a solution of 2 (4.50 g, 36.0 mmol) in $CH_2Cl_2$:$CH_3NO_2$ (1:1, 40 mL) at −40° C., was added $AlCl_3$ (12.48 g, 93.6 mmol) followed by α,α'-dichloromethyl methyl ether (4.15 mL, 46.8 mmol). The resulting mixture was allowed to warm to room temperature and stirred for 16 hours. The reaction mixture was slowly poured onto ice (10.00 g) and allowed to warm to room temperature. The aqueous phase was extracted with $CH_2Cl_2$ (3×50 mL). The combined organic layer was dried over anhydrous $MgSO_4$, filtered and concentrated to give 3 as a dark brown solid (3.40 g, 62%). $^1H$ NMR (400 MHz, $CDCl_3$) δ 10.32 (brs, 1H), 9.83 (s, 1H), 7.59 (m, 1H), 7.30 (s, 1H), and 3.88 (s, 3H); $^{13}C$ NMR (100 MHz, $CDCl_3$) δ 186.07, 161.71, 129.15, 127.71, 124.99, 114.56, and 52.34.

Methyl 4-formyl-5-iodo-1H-pyrrole-2-carboxylate (4)

To a stirred solution of 3 (3.40 g, 22.2 mmol) in $CHCl_3$ (20 mL) at 0° C. was added $CF_3CO_2Ag$ (5.40 g, 24.4 mmol) followed by $I_2$ (3.10 g, 24.4 mmol). The resulting mixture was stirred for 16 hours in the dark at room temperature. The reaction mixture was filtered through Celite and the filtrate was washed with saturated aqueous solution of $Na_2S_2O_3$ (2×20 mL). The organic layer was dried over anhydrous $MgSO_4$, filtered and concentrated in vacuo. MPLC purification ($CH_2Cl_2$:$Et_2O$/95:5) of the residue gave 4 as a white solid (0.72 g, 32% based on the recovered starting material). Along with 4, two minor compounds methyl 4-formyl-5-iodo-1H-pyrrole-2-carboxylate, methyl 4-formyl-3,5-diiodo-1H-pyrrole-2-carboxylate and the starting material 3 were also isolated. $^1H$ NMR (400 MHz, DMSO-$d_6$) δ 13.30 (brs, 1H), 9.52 (s, 1H), 7.04 (s, 1H), and 3.77 (s, 3H); $^{13}C$ NMR (100 MHz, DMSO-$d_6$) δ 187.13, 160.36, 128.78, 127.79, 115.58, 87.40, and 52.42.

Methyl 1-benzyl-4-formyl-5-iodo-1H-pyrrole-2-carboxylate (5)

To a stirred solution of 4 (0.72 g, 2.6 mmol) in acetone (20 mL) was added $K_2CO_3$ (0.71 g, 5.1 mmol). The resulting mixture was stirred for 30 minutes at room temperature. Benzyl bromide (0.46 mL, 3.8 mmol) was added dropwise to the reaction mixture and the mixture was then refluxed for 16 hours. The reaction mixture was cooled to room temperature, concentrated and partitioned between ethyl acetate and water. The combined organic layer was dried over anhydrous $MgSO_4$, filtered and then concentrated in vacuo. MPLC purification (Hexanes:EtOAc/80:20) of the residue gave 5 as a white solid (0.85 g, 90%). $^1H$ NMR (400 MHz, $CDCl_3$) δ 9.66 (s, 1H), 7.50 (s, 1H), 7.24-7.25 (m, 3H), 6.98 (d, J=7.6 Hz, 2H), 5.75 (s, 2H), and 3.72 (s, 3H); $^{13}C$ NMR (100 MHz, $CDCl_3$) δ 186.98, 160.33, 136.43, 128.97, 128.22, 127.84, 127.10, 126.59, 119.32, 92.81, 52.81, and 52.11.

Methyl 1-benzyl-4-formyl-5-(3-hydroxy-3,3-diphenylprop-1-ynyl)-1H-pyrrole-2-carboxylate (6)

A solution of 5 (0.47 g, 1.3 mmol), 1,1-diphenylprop-2-yn-1-ol (0.66 g, 3.2 mmol), CuI (0.05 g, 0.3 mmol), $Pd(PPh_3)_2Cl_2$ (0.18 g, 0.3 mmol), $PPh_3$ (0.07 g, 0.3 mmol), and $Et_3N$ (4 mL) in anhydrous DMF (4 mL) was stirred for 16 hours at 70° C. under $N_2$ atmosphere. The reaction mixture was partitioned between water and EtOAc. The combined organic layer was dried over $MgSO_4$, filtered and concentrated in vacuo. MPLC purification (Hexanes:EtOAc/80:20) of the residue gave 6 as a pale yellow solid (0.49 g, 87%). $^1H$ NMR (400 MHz, $CDCl_3$) δ 9.88 (s, 1H), 7.50-7.52 (m, 4H), 7.36 (s, 1H), 7.24-7.30 (m, 8H), 7.04 (m, 2H), 5.69 (s, 2H), 3.80 (s, 3H), and 3.65 (s, 1H); $^{13}C$ NMR (100 MHz, $CDCl_3$) δ 185.16, 160.72, 144.07, 136.84, 128.91, 128.72, 128.33, 127.91, 127.79, 127.05, 126.23, 124.96, 116.97, 103.35, 75.37, 75.27, 52.15, and 50.38.

1-Benzyl-4-formyl-5-(3-hydroxy-3,3-diphenylprop-1-ynyl)-1H-pyrrole-2-carboxylic acid (7)

To a solution of 6 (0.49 g, 1.1 mmol) in MeOH (20 mL) and water (6 mL) was added KOH (0.18 g, 3.3 mmol) and stirred at 60° C. for 2 hours. The solvent was removed in vacuo. The residue obtained was acidified with 2N HCl to pH 2-3 and extracted with EtOAc (3×15 mL). The combined organic layer was dried over $MgSO_4$, filtered and then concentrated in vacuo to give 7 as a light brown solid. The crude product was subjected to the next reaction without further purification. $^1H$ NMR (400 MHz, $CDCl_3$) δ 9.82 (s, 1H), 7.50-7.52 (m, 4H), 7.45 (s, 1H), 7.21-7.26 (m, 7H), 7.02-7.03 (m, 2H), and 5.64 (s, 2H).

1-Benzyl-7-bis(7-(1,3-dioxoisoindolin-2-yl)heptyl)-4-formyl-5-(3-hydroxy-3,3-diphenylprop-1-ynyl))-1H-pyrrole-2-carboxamide (8)

A solution of 7 (0.49 g, 1.1 mmol), 14 (0.68 g, 1.4 mmol), BOP (benzotriazol-1-yloxytris(dimethylamino)-phosphonium hexafluorophosphate) (0.99 g, 2.3 mmol), HOBt (1-hydroxybenzotriazole) (0.30 g, 2.3 mmol) in anhydrous DMF (3 mL) and NMM (N-methylmorpholine) (2 mL) was stirred at room temperature for 16 hours. The reaction mixture was partitioned between water and EtOAc. The organic layer was dried over $MgSO_4$, filtered and then concentrated in vacuo. MPLC purification (Hexanes:EtOAc/50:50) of the residue gave 8 as a pale yellow oil. (0.72 g, 69%). $^1$H NMR (400 MHz, $CDCl_3$) δ 9.90 (s, 1H), 7.78 (m, 4H), 7.66-7.68 (m, 4H), 7.54-7.56 (m, 4H), 7.17-7.28 (m, 9H), 7.02-7.03 (m, 2H), 6.59 (s, 1H), 5.36 (s, 2H), 4.37 (brs, 1H), 3.59-3.61 (m, 4H), 3.23 (m, 2H), 3.00 (m, 2H), 1.23-1.63 (m, 12H), and 0.91-1.12 (m, 8H); $^{13}$C NMR (100 MHz, $CDCl_3$) δ 185.26, 168.69, 162.59, 144.52, 136.86, 134.11, 132.30, 129.55, 128.88, 128.61, 128.13, 127.84, 127.40, 126.19, 125.04, 123.39, 109.02, 102.66, 75.40, 75.13, 49.62, 38.11, 29.13, 28.69, 26.93, and 26.54.

Ethyl 3-(1-benzyl-7-bis(7-(1,3-dioxoisoindolin-2-yl) heptyl)carbamoyl)-2-(3-hydroxy-3,3-diphenylprop-1-ynyl))-1H-pyrrol-3-yl)acrylate (9)

To a stirred solution of 8 (0.65 g, 0.7 mmol) in benzene (20 mL) was added (ethoxycarbonylmethylene)triphenylphosphorane (0.61 g, 1.8 mmol). The resulting mixture was stirred under reflux for 16 hours. The reaction mixture was cooled to room temperature and the solvent was removed in vacuo. MPLC purification (Hexanes:EtOAc/50:50) of the residue gave 9 as a pale yellow oily liquid (0.54 g, 77%). $^1$H NMR (400 MHz, $CDCl_3$) δ 7.80 (m, 4H), 7.67-7.71 (m, 5H), 7.55-7.57 (m, 4H), 7.18-7.30 (m, 9H), 7.02-7.03 (m, 2H), 6.39 (s, 1H), 6.24 (d, J=16.0 Hz, 1H), 5.32 (s, 2H), 4.17 (q, J=7.2 Hz, 2H), 3.61-3.63 (m, 5H), 3.26 (m, 2H), 3.06 (m, 2H), 1.60-1.62 (m, 4H), and 1.00-1.42 (m, 19H); $^{13}$C NMR (100 MHz, $CDCl_3$) δ 168.64, 167.62, 163.06, 145.11, 137.56, 136.88, 134.09, 132.21, 129.06, 128.70, 128.46, 127.79, 127.74, 126.28, 123.66, 123.32, 119.95, 115.76, 108.67, 102.81, 76.66, 75.02, 60.31, 49.38, 45.40, 38.06, 29.11, 28.64, 26.82, and 14.60.

Ethyl 3-(1-benzyl-5-(bis(7-(1,3-dioxoisoindolin-2-yl)heptyl)carbamoyl)-2-(3-hydroxy-3,3-diphenylpropyl)-1H-pyrrol-3-yl)propanoate (10)

To a stirred solution of 9 (0.12 g, 0.12 mmol) in EtOAc (20 mL) was added 10% dry Pd—C (0.012 g). The resulting mixture was stirred at room temperature for 48 hours under a balloon of hydrogen. Pd—C was filtered off and the filtrate was concentrated to give 10 as a colorless oil. The crude product was subjected to the next reaction without further purification. $^1$H NMR of the crude product is as follows. $^1$H NMR (400 MHz, $CDCl_3$) δ 7.81-7.83 (m, 4H), 7.69-7.71 (m, 4H), 7.31-7.33 (m, 4H), 7.22-7.28 (m, 4H), 7.13-7.20 (m, 5H), 6.78 (d, J=7.2 Hz, 2H), 6.10 (s, 1H), 5.14 (s, 2H), 4.05 (q, J=6.8 Hz, 2H), 3.63-3.66 (t, J=7.2 Hz, 4H), 3.25 (t, J=7.2 Hz, 4H), 2.63 (t, J=7.6 Hz, 2H), 2.43-2.47 (m, 4H), 2.32 (m, 2H), 1.62-1.63 (m, 4H), and 1.14-1.38 (m, 19H).

N,N-Bis(7-aminoheptyl)-1-benzyl-5-(3-(hydroxy-3,3-diphenylpropyl)-4-(3-hydroxyamino)-3-oxopropyl))-1H-pyrrole-2-carboxamide (E4)

To a stirred solution of 10 (0.14 g, 0.14 mmol) in MeOH:THF (1:1, 4 mL) was added 50% aqueous hydroxylamine (4 mL) followed by catalytic amount of KCN. The resulting mixture was stirred at 35° C. for 24 hours. After the solvent was removed in vacuo, the residue was subjected to HPLC purification which gave E4•$(TFA)_2$ as colorless oil (0.034 g, 25%). HPLC purification condition: Phenomenex hyperclone 5μ, C18, 4.60×250 mm, eluting with linear gradient of 20% of solution B to 100% of solution B (Solution A is 1000 mL of $H_2O$ and 1 mL of TFA and solution B is 100 mL of $H_2O$, 900 mL of $CH_3CN$ and 1 mL of TFA) over 20 minutes, and a flow rate of 1.0 mL/min with a retention time of 12.93 min for E4•$(TFA)_2$. $^1$H NMR (400 MHz, DMSO-$d_6$) δ 10.41 (brs, 1H), 7.71 (m, 6H), 7.40-7.42 (m, 4H), 7.14-7.26 (m, 9H), 6.67 (d, J=7.2 Hz, 2H), 6.09 (s, 1H), 5.14 (s, 2H), 3.21 (m, 4H), 2.72-2.73 (m, 4H), 2.48 (overlapped with DMSO-$d_6$, 2H), 2.32 (m, 4H), 2.11 (t, J=7.2 Hz, 2H), 1.44-1.46 (m, 4H), 1.31 (m, 4H), 1.18 (m, 8H), and 1.06 (m, 4H); $^{13}$C NMR (100 MHz, DMSO-$d_6$) δ 169.46, 164.21, 158.68 (q), 148.59, 140.08, 133.69, 128.91, 128.54, 127.39, 126.86, 126.44, 126.28, 124.93, 118.32, 117.57 (q), 111.44, 76.72, 55.61, 47.22, 42.32, 39.40, 34.57, 28.92, 27.58, 26.67, 26.34, 21.78, and 19.05.

2-(7-bromoheptyl)isoindoline-1,3-dione (12)

To a stirred solution of 1,7-dibromoheptane (11) (13.90 g, 53.9 mmol) in acetone (100 mL) was added potassium phthalimide (5.00 g, 27.0 mmol). The resulting mixture was refluxed for 16 hours. The reaction mixture was cooled to room temperature and the solvent was removed in vacuo. MPLC purification of the residue (Hexanes:EtOAc/70:30) gave 12 as a colorless oil (6.62 g, 75%). $^1$H NMR (400 MHz, $CDCl_3$) δ 7.83-7.84 (m, 2H), 7.69-7.72 (m, 2H), 3.67 (t, J=7.6 Hz, 2H), 3.39 (t, J=7.2 Hz, 2H), 1.82-1.84 (m, 2H), 1.67 (m, 2H), and 1.35 (m, 6H); $^{13}$C NMR (100 MHz, $CDCl_3$) δ 168.55, 134.06, 132.30, 123.32, 38.06, 34.12, 32.85, 28.67, 28.48, 28.19, and 26.83.

2,2'-(7,7'-(benzylazanediyl)bis(heptane-1,7-diyl)) didioindoline-1,3-dione (13)

To a stirred solution of 12 (9.40 g, 29.0 mmol) in acetonitrile (200 mL) was added $K_2CO_3$ (7.60 g, 55.0 mmol) and benzyl amine (1.48 g, 13.8 mmol). The resulting solution was refluxed for 48 hours. The reaction mixture was cooled to room temperature, filtered and the filtrate was concentrated in vacuo. MPLC purification (Hexanes:EtOAc/70:30) of the residue gave 13 as a yellow viscous oil (6.29 g, 81%). $^1$H NMR (400 MHz, $CDCl_3$) δ 7.82-7.84 (m, 4H), 7.70-7.71 (m, 4H), 7.27-7.28 (m, 4H), 7.20 (m, 1H), 3.65 (t, J=7.2 Hz, 4H), 3.50 (s, 2H), 2.35 (t, J=7.2 Hz, 4H), 1.64 (m, 4H), 1.42 (m, 4H), and 1.25-1.28 (m, 12H); $^{13}$C NMR (100 MHz, $CDCl_3$) δ 168.61, 140.42, 134.04, 132.37, 129.03, 128.24, 126.79, 123.33, 58.80, 53.91, 38.24, 29.33, 28.80, 27.48, 27.13, and 27.07.

2,2'-(7,7'-azanediylbis(heptane-1,7-diyl))didioindoline-1,3-dione (14)

To a stirred solution of 13 (1.50 g, 2.5 mmol) in MeOH:EtOAc (1:1, 40 mL) was added 10% Pd—C (0.15 g). The resulting mixture was stirred at room temperature for 16 hours under a balloon of hydrogen. The reaction mixture was filtered off and the filtrate was concentrated in vacuo. MPLC purification of the residue gave 14 as an amorphous white solid (1.05 g, 82%). $^1$H NMR (400 MHz, MeOH-$d_4$) δ 7.79-7.85 (m, 8H), 3.67 (t, J=7.2 Hz), 2.94 (t, J=8.0 Hz), 1.63-1.70 (m, 8H), and 1.35-1.41 (m, 12H); $^{13}$C NMR (100 MHz, MeOH-$d_4$) δ 168.72, 134.19, 132.15, 122.99, 49.40, 37.67, 29.02, 28.89, 28.33, 27.08, and 26.25.

Example 5

Synthesis of E5

Figure 5:
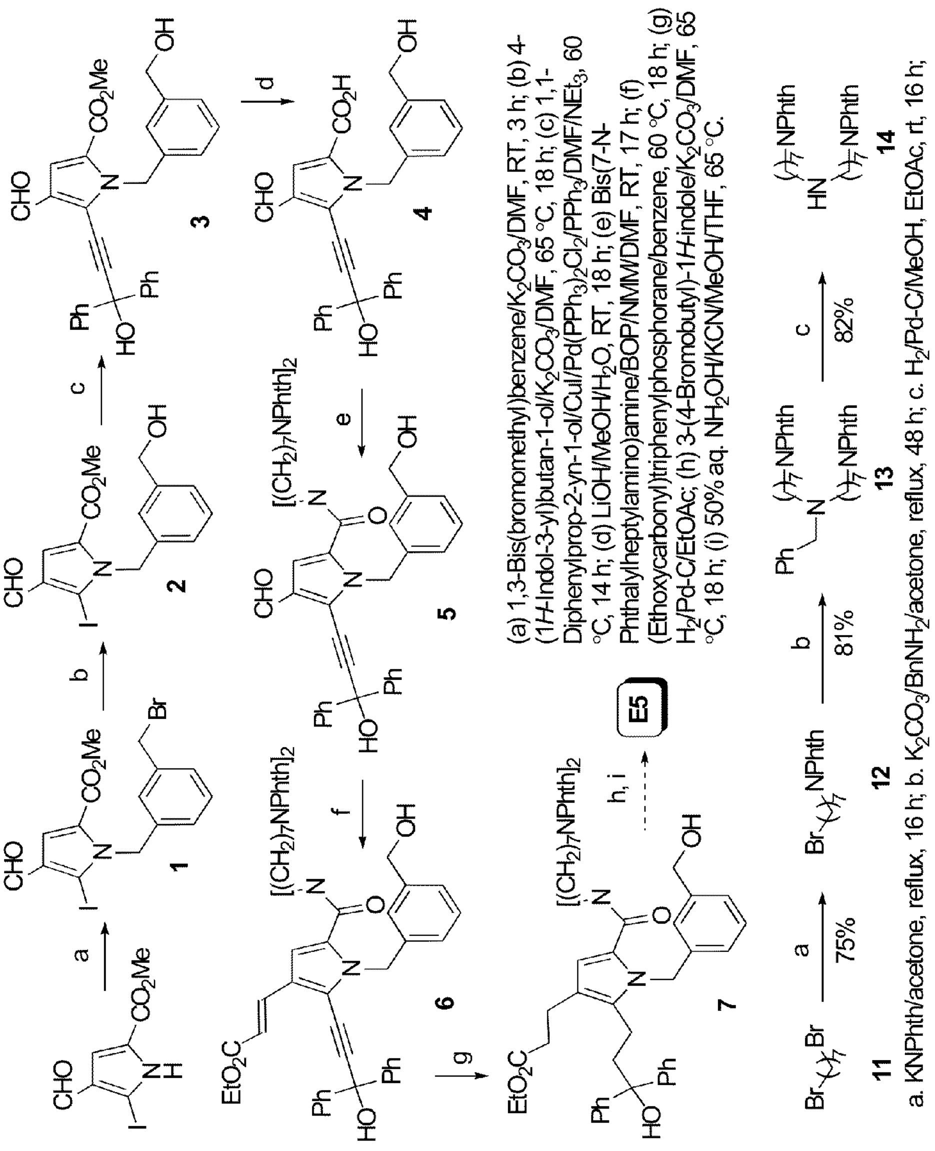
FIG. 5 is a scheme illustrating a synthesis of E5.

E5 was synthesized according to the scheme in FIG. 5.

Methyl 1-(3-(bromomethyl)benzyl)-4-formyl-5-iodo-1H-pyrrole-2-carboxylate (1)

To a stirred solution of the starting pyrrole (0.15 g, 0.54 mmol) in DMF (3 mL) was added 1,3-Bis(bromomethyl) benzene (0.43 g, 1.61 mmol) and $K_2CO_3$ (74 mg, 0.54 mmol) at room temperature. After 3 hours og stirring, 3 mL of water was added, extracted with EtOAc, washed with brine, dried over $MgSO_4$, and then purified by MPLC (gradient: Hex to EtOAc) to afford 0.20 g (80%) of the titled compound; $^1H$ NMR (400 MHz, $CDCl_3$) δ 9.71 (s, 1H), 7.54 (s, 1H), 7.25-7.30 (m, 2H), 7.08 (s, 1H), 6.89 (d, J=6.4 Hz, 1H), 5.78 (s, 2H), 4.44 (s, 2H), and 3.78 (s, 2H): $^{13}C$ NMR (100 MHz, $CDCl_3$) δ 187.04, 160.40, 138.56, 137.06, 129.53, 128.62, 128.24, 127.31, 127.19, 126.53, 119.49, 92.41, 52.58, 52.17, and 33.39.

Methyl 4-formyl-1-(3-(hydroxymethyl)benzyl)-5-iodo-1H-pyrrole-2-carboxylate (2)

To a stirred solution of 1 (0.20 g, 0.43 mmol) in DMF (2.5 mL) was added 4-(1H-Indol-3-yl)butan-1-ol (82 mg, 0.43 mmol) and $K_2CO_3$ (60 mg, 0.43 mmol) at room temperature. The resulting mixture was heated at 65° C. for 18 hours. After cooling to room temperature water (3 mL) was added, extracted with EtOAc, washed with brine, dried over $MgSO_4$, and then purified by MPLC (gradient: Hex to EtOAc) to give 0.16 g of the titled compound as an inseparable mixture with 4-(1H-Indol-3-yl)butan-1-ol. It was intended to obtain an ether, but the reaction converted the Br to OH; $^1H$ NMR (400 MHz, $CDCl_3$) δ 9.70 (s, 1H), 7.54 (s, 1H), 7.27-7.2 (m, 2H), 7.04 (s, 1H), 6.87 (d, J=7.0 Hz, 1H), 5.79 (s, 2H), 4.65 (s, 2H), and 3.77 (s, 2H).

Methyl 4-formyl-5-(3-hydroxy-3,3-diphenylprop-1-ynyl)-1-(3-(hydroxymethyl)-benzyl)-1H-pyrrole-2-carboxylate (3)

The mixture obtained above (162 mg) was dissolved in 4 mL 1:1 mixture of DMF/$Et_3N$, to this was added 1,1-diphenylprop-2-yn-1-ol (147 mg), CuI (11 mg), $Pd(PPh_3)_2Cl_2$ (40 mg, and $PPh_3$ (15 mg) at room temperature. The resulting mixture was heated at 60° C. for 14 hours. After cooling to room temperature, water (4 mL) was added, extracted with EtOAc, washed with brine, dried over $MgSO_4$, and then purified by MPLC (gradient: Hex to EtOAc) to afford 62 mg of the titled compound as an inseparable mixture with 4-(1H-indol-3-yl)butan-1-ol; $^1H$ NMR (400 MHz, $CDCl_3$) δ 9.89 (s, 1H), 7.60 (d, J=8.0 Hz, 1H), 7.55 (d, J=7.2 Hz, 4H), 7.07-7.36 (m, 19H), 6.95 (s, 1H), 5.71 (s, 2H), 4.60 (brs, 1H), 4.51 (s, 2H), 3.84 (s, 3H), 3.64 (t, J=6.6 Hz, 2H), 2.78 (t, J=7.2 Hz, 2H), 1.73-1.79 (m 2H), and 1.61-1.68 (m, 2H): $^{13}C$ NMR (100 MHz, $CDCl_3$) δ 185.08, 160.95, 144.28, 141.14, 137.14, 136.56, 129.13, 128.72, 128.29, 127.90, 127.72, 126.99, 126.85, 126.61, 126.12, 124.71, 122.08, 121.42, 119.29, 119.13, 116.96, 116.73, 111.31, 103.80, 75.44, 75.20, 65.08, 63.14, 52.20, 50.34, 32.82, 26.45, and 25.11.

4-Formyl-5-(3-hydroxy-3,3-diphenylprop-1-ynyl)-1-(3-(hydroxymethyl)benzyl)-1H-pyrrole-2-carboxylic acid (4)

Lithium hydroxide (10 mg) was added into a stirred solution of the material obtained above (94 mg) in a mixture of MeOH (1 mL) and water (0.3 mL) at room temperature. After 18 hours of stirring, MeOH was evaporated in vacuo. The residue was dissolved in 3 mL water, washed with EtOAc, the aqueous layer was acidified with 1 N HCl, extracted with EtOAc, washed with brine, dried over $MgSO_4$, and then concentrated. To the residue a small amount of $CHCl_3$ was added to induce crystallization of the product, which was sparingly soluble in $CHCl_3$. The product was collected by filtration to give 50 mg of the brown powder; $^1H$ NMR (400 MHz, DMSO-$d_6$) δ 13.0 (brs, 1H), 9.90 (s, 1H), 7.49 (d, J=7.4 Hz, 4H), 7.22-7.28 (m, 9H), 7.08, (s, 1H), 6.90 (s, 1H), 5.76 (s, 2H), 5.21 (brs, 1H), 4.41 (s, 2H), and 3.40 (brs, 1H): $^{13}C$ NMR (100 MHz, DMSO-$d_6$) δ 185.37, 161.59, 145.94, 143.62, 137.72, 129.03, 128.87, 128.11, 127.57, 126.74, 126.23, 125.48, 124.92, 116.46, 104.29, 74.48, 74.26, 63.34, 60.47, and 50.26.

N,N-Bis(7-(1,3-dioxoisoindolin-2-yl)heptyl)-4-formyl-5-(3-hydroxy-3,3-diphenylprop-1-ynyl)-1-(3-(hydroxymethyl)benzyl)-1H-pyrrole-2-carboxamide (5)

The compound 4 (50 mg) in anhydrous DMF (2 mL) was treated with 2,2'-(7,7'-azanediylbis(heptane-7,1-diyl))diisoindoline-1,3-dione (56 mg) in the presence of BOP (49 mg) and NMM (15 μL) at room temperature for 20 hours. The reaction mixture was diluted with water (3 mL), extracted with EtOAc, washed with brine, dried over $MgSO_4$, and then purified by MPLC (gradient: Hex to EtOAc) to give 38 mg of the title compound (36%) as a pale yellow solid foam; $^1H$ NMR (400 MHz, $CDCl_3$) δ 9.93 (s, 1H), 7.81 (m, 4H), 7.79 (m, 4H), 7.56 (d, J=6.8 Hz, 4H), 7.20-7.34 (m, 9H), 7.07 (d, J=6.4H), 6.65 (s, 1H), 5.39 (s, 2H), 4.56 (s, 2H), 3.96 (s, 1H), 3.65 (m 4H), 3.33 (m, 2H), 3.16 (m, 2H), and 1.17-1.60 (m, 20H).

(E)-Ethyl 3-(5-(bis(7-(1,3-dioxoisoindolin-2-yl)heptyl)carbamoyl)-2-(3-hydroxy-3,3-diphenylprop-1-ynyl)-1-(3-(hydroxymethyl)benzyl)-1H-pyrrol-3-yl) acrylate (6)

The compound 6 (7 mg) was treated with (Ethoxycarbonyl) triphenylphosphorane (4 mg) in benzene (0.5 mL) at 65° C. for 15 hours. The solvent was evaporated, the residue purified by MPLC (gradient: Hex to EtOAc) to give 4 mg of the title compound as brown oily residue; $^1H$ NMR (400 MHz, $CDCl_3$) δ 7.82 (m, 4H), 7.65-7.79 (m, 5H), 7.57 (d, J=7.4 Hz, 4H), 7.18-7.31 (m, 9H), 7.03 (d, J=6.4H), 6.41 (s, 1H), 6.24 (d, J=15.8 Hz, 1H), 5.32 (s, 2H), 4.55 (s, 2H), 4.17 (q, J=7.0 Hz, 2H), 3.65 (m 4H), 3.16-3.33 (m, 4H), and 1.17-1.60 (m, 23H).

Ethyl 3-(5-(bis(7-(1,3-dioxoisoindolin-2-yl)heptyl) carbamoyl)-2-(3-hydroxy-3,3-diphenylpropyl)-1-(3-(hydroxymethyl)benzyl)-1H-pyrrol-3-yl)propanoate (7)

The compound 6 (4 mg) obtained above was subsequently reduced by passing $H_2$ through a stirred suspension in EtOAc (2 mL) and 10% Pd—C (4 mg) for 6 hours (or until the reaction completed by NMR). The catalyst was filtered off (Celite), the filtrate was evaporated in vacuo to give 4 mg of the title compound as a crude mixture; $^1H$ NMR (400 MHz, $CDCl_3$) δ 7.82 (m, 4H), 7.70 (m, 4H), 7.20-7.32 (m, 14H), 6.10 (s, 1H), 5.10 (s, 2H), 4.56 (s, 2H), 4.04 (m, 2H), 3.64 (m 4H), 3.25 (m, 4H), 2.09-2.62 (m, 8H), and 1.17-1.62 (m, 23H).

Example 6

Synthesis of E6

E6 was synthesized according to the scheme in FIG. 6.

Methyl 1H-pyrrole-2-carboxylate (2)

To a stirred solution of 2-(trichloroacetyl)pyrrole (1) (10.00 g, 47.1 mmol) in MeOH (20 mL) was added $K_2CO_3$ (8.44 g, 61.2 mmol). The resulting mixture was stirred under reflux for 3 hours, cooled to room temperature and filtered. The filtrate was concentrated in vacuo to give 2 as a dark brown solid (5.50 g, 93%). $^1$H NMR (400 MHz, $CDCl_3$) δ 9.49 (brs, 1H), 6.92-6.96 (m, 2H), 6.26 (m, 1H), and 3.86 (s, 3H); $^{13}$C NMR (100 MHz, $CDCl_3$) δ 162.05, 123.33, 122.79, 115.56, 110.66, and 51.72.

Methyl 4-formyl-1H-pyrrole-2-carboxylate (3)

To a solution of 2 (4.50 g, 36.0 mmol) in $CH_2Cl_2$:$CH_3NO_2$ (1:1, 40 mL) at −40° C., was added $AlCl_3$ (12.48 g, 93.6 mmol) followed by α,α-dichloromethyl methyl ether (4.15 mL, 46.8 mmol). The resulting mixture was allowed to warm to room temperature and stirred for 16 hours. The reaction mixture was slowly poured onto ice (10.00 g) and allowed to warm to room temperature. The aqueous phase was extracted with $CH_2Cl_2$ (3×50 mL). The combined organic layer was dried over anhydrous $MgSO_4$, filtered and concentrated to give 3 as a dark brown solid (3.40 g, 62%). $^1$H NMR (400 MHz, $CDCl_3$) δ 10.32 (bs, 1H), 9.83 (s, 1H), 7.59 (d, J=1.6 Hz, 1H), 7.30 (s, 1H), and 3.88 (s, 3H); $^{13}$C NMR (100 MHz, $CDCl_3$) δ 186.07, 161.71, 129.15, 127.71, 124.99, 114.56, and 52.34.

Methyl 4-formyl-5-iodo-1H-pyrrole-2-carboxylate (4)

To a stirred solution of 3 (3.40 g, 22.2 mmol) in $CHCl_3$ (20 mL) at 0° C. was added $CF_3CO_2Ag$ (5.40 g, 24.4 mmol) followed by $I_2$ (3.10 g, 24.4 mmol). The resulting mixture was stirred for 16 hours in the dark at room temperature. The reaction mixture was filtered through Celite and the filtrate was washed with saturated aqueous solution of $Na_2S_2O_3$ (2×20 mL). The organic layer was dried over anhydrous $MgSO_4$, filtered and concentrated in vacuo. MPLC purification ($CH_2Cl_2$:diethyl ether/95:5) of the residue gave 4 as a white solid (0.72 g, 32% based on the recovered starting material). Along with 4, two minor compounds methyl 4-formyl-5-iodo-1H-pyrrole-2-carboxylate, methyl 4-formyl-3,5-diiodo-1H-pyrrole-2-carboxylate and the starting material 3 were also isolated. $^1$H NMR (400 MHz, DMSO-$d_6$) δ 13.30 (brs, 1H), 9.52 (s, 1H), 7.04 (s, 1H), and 3.77 (s, 3H); $^{13}$C NMR (100 MHz, DMSO-$d_6$) δ 187.13, 160.36, 128.78, 127.79, 115.58, 87.40, and 52.42.

Methyl 1-benzyl-4-formyl-5-iodo-1H-pyrrole-2-carboxylate (5)

To a stirred solution of 4 (0.72 g, 2.6 mmol) in acetone (20 mL) was added $K_2CO_3$ (0.71 g, 5.1 mmol). The resulting mixture was stirred for 30 minutes at room temperature. Benzyl bromide (0.46 mL, 3.8 mmol) was added dropwise to the reaction mixture and the resulting mixture was refluxed for 16 hours. The reaction mixture was cooled to room temperature, concentrated and partitioned between ethyl acetate and water. The combined organic layer was dried over anhydrous $MgSO_4$, filtered and then concentrated in vacuo. MPLC purification (Hexanes:EtOAc/80:20) of the residue gave 5 as a white solid (0.85 g, 90%). $^1$H NMR (400 MHz, $CDCl_3$) δ 9.66 (s, 1H), 7.50 (s, 1H), 7.24-7.25 (m, 3H), 6.98 (d, J=7.6 Hz, 2H), 5.75 (s, 2H), and 3.72 (s, 3H); $^{13}$C NMR (100 MHz, $CDCl_3$) δ 186.98, 160.33, 136.43, 128.97, 128.22, 127.84, 127.10, 126.59, 119.32, 92.81, 52.81, and 52.11.

Methyl 1-benzyl-4-formyl-5-(3-hydroxy-3,3-diphenylprop-1-ynyl)-1H-pyrrole-2-carboxylate (6)

A solution of 5 (0.47 g, 1.3 mmol), 1,1-diphenylprop-2-yn-1-ol (0.66 g, 3.2 mmol), CuI (0.05 g, 0.3 mmol), $Pd(PPh_3)_2Cl_2$ (0.18 g, 0.3 mmol), $PPh_3$ (0.07 g, 0.3 mmol), and $Et_3N$ (4 mL) in anhydrous DMF (4 mL) was stirred for 16 hours at 70° C. under $N_2$ atmosphere. The reaction mixture was partitioned between water and EtOAc. The combined organic layer was dried over $MgSO_4$, filtered and concentrated in vacuo. MPLC purification (Hexanes:EtOAc/80:20) of the residue gave 6 as a pale yellow solid (0.49 g, 87%). $^1$H NMR (400 MHz, $CDCl_3$) δ 9.88 (s, 1H), 7.50-7.52 (m, 4H), 7.36 (s, 1H), 7.24-7.30 (m, 8H), 7.04 (m, 2H), 5.69 (s, 2H), 3.80 (s, 3H), and 3.65 (s, 1H); $^{13}$C NMR (100 MHz, $CDCl_3$) δ 185.16, 160.72, 144.07, 136.84, 128.91, 128.72, 128.33, 127.91, 127.79, 127.05, 126.23, 124.96, 116.97, 103.35, 75.37, 75.27, 52.15, and 50.38.

1-Benzyl-4-formyl-5-(3-hydroxy-3,3-diphenylprop-1-ynyl)-1H-pyrrole-2-carboxylic acid (7)

To a solution of 6 (0.49 g, 1.1 mmol) in MeOH (20 mL) and water (6 mL) was added KOH (0.18 g, 3.3 mmol) and stirred at 60° C. for 2 hours. The solvent was removed in vacuo. The residue obtained was acidified with 2N HCl to pH 2-3 and extracted with EtOAc (3×15 mL). The combined organic layer was dried over $MgSO_4$, filtered and then concentrated in vacuo to give 7 as a light brown solid. The crude product was subjected to the next reaction without further purification. $^1$H NMR (400 MHz, $CDCl_3$) δ 9.82 (s, 1H), 7.50-7.52 (m, 4H), 7.45 (s, 1H), 7.21-7.26 (m, 7H), 7.02-7.03 (m, 2H), and 5.64 (s, 2H).

1-Benzyl-N-(3,5-bis(6-(1,3-dioxoisoindolin-2-yl)hexyl)-4-(6-(1,3-dioxoisoindolin-2-yl)hexyloxy)phenyl)-4-formyl-5-(3-hydroxy-3,3-diphenylprop-1-ynyl)-1H-pyrrole-2-carboxamide (8)

A solution of 7 (0.11 g, 0.25 mmol), 14 (0.24 g, 0.30 mmol), BOP (benzotriazol-1-yloxytris(dimethylamino)phosphonium hexafluorophosphate) (0.22 g, 0.51 mmol), HOBt (1-hydroxybenzotriazole) (0.07 g, 0.51 mmol) in anhydrous DMF (3 mL) and NMM (N-methylmorpholine) (2 mL) was stirred at room temperature for 16 hours. The reaction mixture was partitioned between water (20 mL) and EtOAc (20 mL). The aqueous layer was washed with EtOAc (2×20 mL). The combined organic layer was dried over $MgSO_4$, filtered and then concentrated in vacuo. MPLC purification (Hexanes:EtOAc/50:50) of the residue gave 8 as a pale yellow oil. (0.20 g, 65%). $^1$H NMR (400 MHz, $CDCl_3$) δ 9.74 (s, 1H), 9.18 (s, 1H), 7.59 (m, 6H), 7.49 (m, 6H), 7.35-7.37 (m, 4H), 7.17-7.19 (m, 2H), 6.93-7.09 (m, 11H), 6.14 (s, 1H), 5.61 (s, 2H), 3.45-3.49 (m, 8H), 2.37 (m, 4H), 1.38-1.54 (m, 14H), and 1.19 (m, 10H).

Ethyl 3-(1-benzyl-5-(3,5-bis(6-(1,3-dioxoisoindolin-2-yl)hexyl)-4-(6-(1,3-dioxoisoindolin-2-yl)hexyloxy)phenylcarbamoyl)-2-(3-hydroxy-3,3-diphenylprop-1-ynyl)-1H-pyrrol-3-yl)acrylate (9)

To a stirred solution of 8 (0.20 g, 0.17 mmol) in benzene (20 mL) was added (ethoxycarbonylmethylene)triphenyl phosphorane (0.14 g, 0.41 mmol). The resulting mixture was stirred under reflux for 16 hours. The reaction mixture was cooled to room temperature and the solvent was removed in vacuo. MPLC purification (Hexanes:EtOAc/50:50) of the residue gave 9 as a pale yellow oily liquid (0.08 g, 35%). $^{1}$H NMR (400 MHz, $CDCl_3$) δ 8.17 (s, 1H), 7.74 (m, 6H), 7.59-7.64 (m, 7H), 7.49 (m, 4H), 7.21-7.24 (m, 7H), 7.13 (m, 3H), 7.00 (m, 2H), 6.91 (s, 1H), 6.20 (d, J=16.0 Hz, 1H), 5.64 (s, 2H), 4.03-4.14 (m, 2H), 3.82 (s, 1H), 3.61-3.82 (m, 8H), 2.52 (m, 4H), 1.54-1.72 (m, 14H), and 1.23-1.34 (m, 13H).

Ethyl 3-(1-benzyl-5-(3,5-bis(6-(1,3-dioxoisoindolin-2-yl)hexyl)-4-(6-(1,3-dioxoisoindolin-2-yl)hexyloxy)phenylcarbamoyl)-2-(3-hydroxy-3,3-diphenylprop-1-ynyl)-1H-pyrrol-3-yl)propanoate (10)

To a stirred solution of 9 (0.07 g, 0.06 mmol) in EtOAc (20 mL) was added 10% dry Pd—C (0.007 g). The resulting mixture was stirred at room temperature for 48 hours under a $H_2$ balloon. Pd—C was filtered off and the filtrate was concentrated to give 10 as colorless oil (0.06 g, 74%). The crude product was subjected to the next reaction without further purification. $^{1}$H NMR of the crude product is as follows. $^{1}$H NMR (400 MHz, $CDCl_3$) δ 7.78-7.80 (m, 4H), 7.63-7.68 (m, 5H), 7.21-7.28 (m, 6H), 7.12-7.20 (m, 8H), 6.76-6.77 (d, J=7.2 Hz, 1H), 6.59 (s, 1H), 5.52 (s, 2H), 4.03-4.09 (m, 2H), 3.62-3.69 (m, 8H), 2.60-2.62 (m, 2H), 2.42-2.53 (m, 8H), 2.19-2.22 (m 2H), 1.42-1.72 (m, 14H), 1.35-1.40 (m, 10H), and 1.24 (m, 3H).

1-Benzyl-N-(3,5-bis(6-(1,3-dioxoisoindolin-2-yl)hexyl)-4-(6-(1,3-dioxoisoindolin-2-yl)hexyloxy)phenyl)-5-(3-hydroxy-3,3-diphenylprop-1-ynyl)-4-(3-(hydroxyamino)-3-oxopropyl)-1H-pyrrole-2-carboxamide trifluoroacetic acid salt [E6•(TFA)$_3$]

To a stirred solution of 10 (0.05 g, 0.04 mmol) in MeOH:THF (1:1, 4 mL) was added 50% aqueous hydroxylamine (4 mL) followed by a catalytic amount of KCN. The resulting mixture was stirred at 35° C. for 24 hours. After the solvent was removed in vacuo, the residue was subjected to HPLC purification which gave E6•(TFA)$_3$ as colorless oil (0.011 g, 22%). HPLC purification condition: Phenomenex hyperclone 5μ, C18, 4.60×250 mm, eluting with linear gradient of 20% of solution B to 100% of solution B (Solution A is 1000 mL of $H_2O$ and 1 mL of TFA and solution B is 100 mL of $H_2O$, 900 mL of $CH_3CN$ and 1 mL of TFA) over 20 minutes, and a flow rate of 1.0 mL/min with a retention time of 11.68 min for E6•(TFA)$_3$. $^{1}$H NMR (400 MHz, DMSO-$d_6$) 10.35 (s, 1H), 9.48 (s, 1H), 7.67 (bs, 9H), 7.67 (brs, 9H), 7.38-7.40 (m, m, 4H), 7.13-7.27 (m, 9H), 6.89 (s, 1H), 6.67-6.69 (d, J=7.2 Hz, 2H), 5.74 (s, 2H), 3.62 (t, 2H), 2.74 (m, 6H), 2.48 (m, 6H), 2.28 (m, 4H), 2.15 (t, J=7.2 Hz, 2H), 1.67 (m, 2H), 1.49 (m, 12H), and 1.29 (m, 10H).

2-(6-(2,6-Dibromo-4-nitrophenoxy)hexyl)isoindoline-1,3-dione (12)

To a solution of 2,6-dibromo-4-nitrophenol (2.00 g, 6.74 mmol) in acetonitrile (10 mL) was added potassium carbonate (2.79 g, 20.22 mmol). The resulting mixture was stirred for 0.5 h under reflux conditions. To this was added 6-bromohexylphthalimide (2.30 g, 7.41 mmol) and continued stirring for another 72 hours at 80° C. The reaction mixture was cooled to room temperature and filtered through Celite. The filtrate was concentrated in vacuo. MPLC purification (Hexanes:EtOAc/80:20) of the residue gave 12 as a white amorphous solid (1.10 g, 60%). $^{1}$H NMR (400 MHz, $CDCl_3$) δ 8.38 (s, 2H), 7.82-7.84 (m, 2H), 7.69-7.72 (m, 2H), 4.07 (t, J=6.4 Hz, 2H), 3.70 (t, J=7.2 Hz, 2H), 1.87-1.91 (m, 2H), 1.72-1.75 (m, 2H), 1.58-1.62 (m, 2H), and 1.43-1.47 (m, 2H).

2,2'-(6,6'-(2-(6-(1,3-Dioxoisoindolin-2-yl)hexyloxy)-5-nitro-1,3-phenylene)bis(hex-5-yne-6,1-diyl))diisoindoline-1,3-dione (13)

A solution of 12 (0.50 g, 0.95 mmol), 2-(hex-5-ynyl)isoindoline-1,3-dione (0.86 g, 3.80 mmol), CuI (0.07 g, 0.38 mmol), $Pd(PPh_3)_2Cl_2$ (0.13 g, 0.19 mmol) in anhydrous DMF (4 mL) and $Et_3N$ (4 mL) was stirred for 24 hours at 80° C. under $N_2$ atmosphere. The reaction mixture was partitioned between water and EtOAc. The combined organic layer was dried over $MgSO_4$, filtered and concentrated in vacuo. MPLC purification (Hexanes:EtOAc/50:50) of the residue gave 13 as a pale yellow liquid (0.55 g, 71%). $^{1}$H NMR (400 MHz, $CDCl_3$) δ 8.07 (s, 2H), 7.81 (m, 4H), 7.68-7.70 (m, 4H), 4.27 (t, 2H), 3.72 (t, 4H), 3.56 (t, 2H), 2.50 (t, 4H), 1.86 (m, 4H), 1.52-1.78 (m, 8H), 1.50-1.58 (m, 2H), and 1.34-1.42 (m, 2H).

2,2'-(6,6'-(5-Amino-2-(6-(1,3-dioxoisoindolin-2-yl)hexyloxy)-1,3-phenylene)bis(hexane-6,1-diyl))diisoindoline-1,3-dione (14)

To a stirred solution of 13 (0.50 g, 0.61 mmol) in EtOAc (20 mL) was added dry powdered 10% Pd—C (0.05 g). The resulting mixture was stirred at room temperature for 12 hours under a $H_2$ balloon. Pd—C was filtered off and the filtrate was concentrated to give 14 as pale yellow oil (0.46 g, 95%). The crude product was subjected to the next reaction without further purification. $^{1}$H NMR of the crude product is as follows. $^{1}$H NMR (400 MHz, $CDCl_3$) δ 7.70-7.83 (m, 4H), 7.68-7.69 (m, 4H), 6.33 (s, 2H), 3.61-3.68 (m, 8H), 2.47 (t, J=8.0 Hz 4H), 1.65-1.73 (m, 8H), 1.51-1.55 (m, 6H), and 1.37 (m, 10H).

Example 7

Synthesis of E1c

Figure 14:
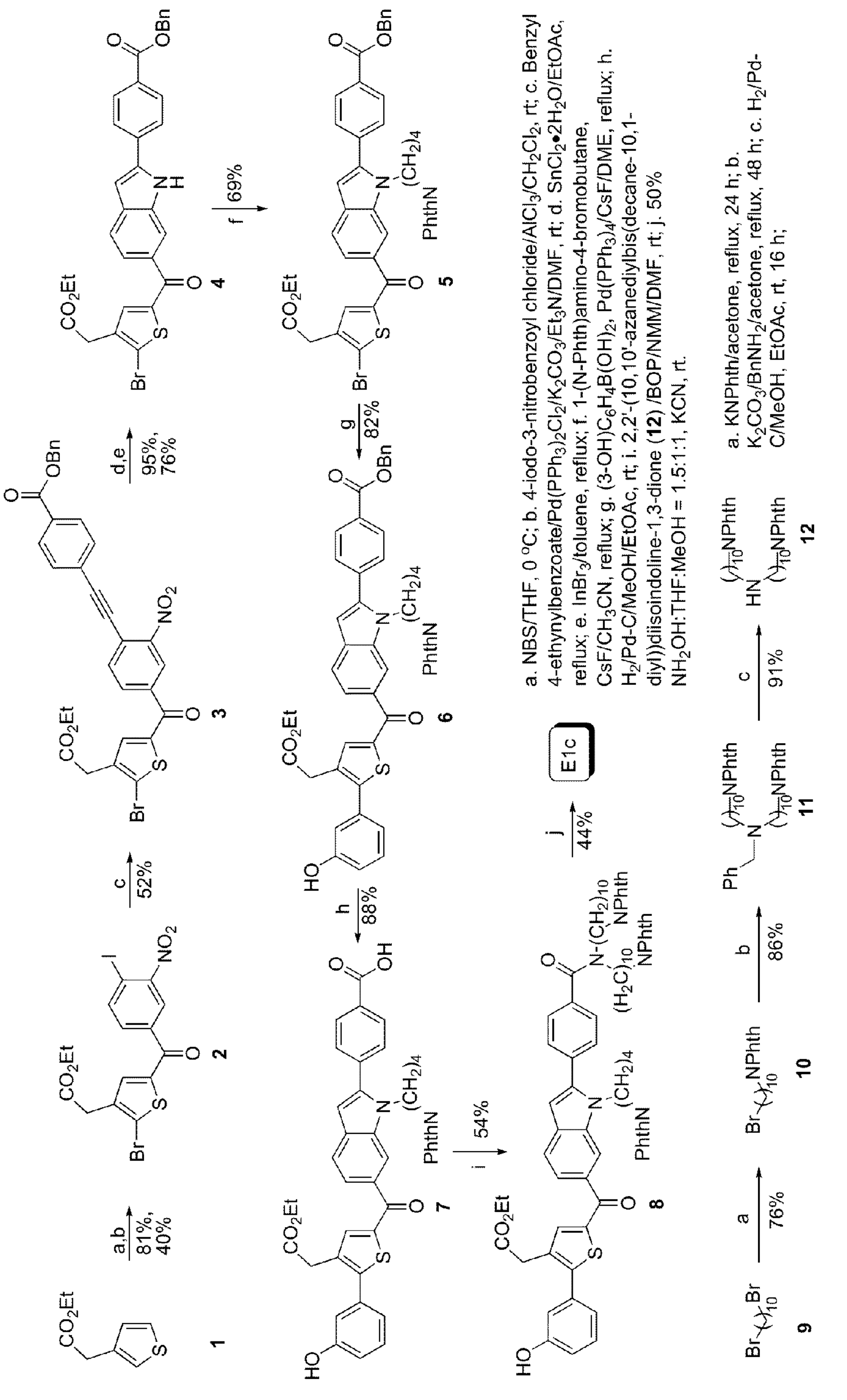
FIG. 14 is a scheme illustrating a synthesis of E1c.

E1c was synthesized according to the scheme in FIG. 14.

Ethyl 2-(2-bromo-5-(4-iodo-3-nitrobenzoyl)thiophen-3-yl)acetate (2)

To a solution of ethyl 2-(thiophen-3-yl)acetate (1, 20.30 g, 119.25 mmol) in THF (150 mL) was added NBS (21.23 g, 119.25 mmol) over a period of 5 hours at 0° C., and then the mixture was warmed up to room temperature, and stirring continued for 24 hours. The solvent was removed in vacuo, and the residue was dissolved in EtOAc (150 mL) and washed with brine (4×30 mL). The organic layer was dried over $MgSO_4$, filtered, and then concentrated in vacuo. MPLC purification (Hex/EtOAc 5:1) of the residue gave ethyl 2-(2-bromothiophen-3-yl)acetate as a colorless oil (24.00 g, 81%). $^{1}$H NMR (400 MHz, $CDCl_3$) δ 7.23 (d, J=5.4 Hz, 1H), 6.93 (d, J=5.4 Hz, 1H), 4.17 (q, J=7.2 Hz, 2H), 3.61 (s, 2H), and 1.27 (t, J=7.2 Hz, 3H); $^{13}$C NMR (100 MHz, $CDCl_3$) δ 170.37, 133.84, 128.90, 125.93, 111.78, 61.32, 35.30, and 14.43.

To a solution of ethyl 2-(2-bromothiophen-3-yl)acetate (24.00 g, 96.32 mmol) and 4-iodo-3-nitrobenzoyl chloride (30.00 g, 96.32 mmol) in anhydrous $CH_2Cl_2$ (100 mL) was added $AlCl_3$ (38.53 g, 288.96 mmol) during a period of 4 hours at room temperature. The resulting mixture was stirred for 2 days. The reaction mixture was slowly poured onto 200 g of ice and allowed to warm to room temperature. The aqueous phase was extracted with $Et_2O$ (4×30 mL), and the combined organic layer was dried over $MgSO_4$, filtered, and then concentrated in vacuo. MPLC purification of (Hex:EtOAc/4:1) of the residue gave 2 as a light yellow solid (20.00 g, 40%). $^1H$ NMR (400 MHz, $CDCl_3$) δ 8.26 (d, J=2.0 Hz, 1H), 8.21 (d, J=8.2 Hz, 1H), 7.69 (dd, J=2.0, 8.2 Hz, 1H), 7.48 (s, 1H), 4.19 (q, J=7.2 Hz, 2H), 3.66 (s, 2H), and 1.28 (t, J=7.2 Hz, 3H); $^{13}C$ NMR (100 MHz, $CDCl_3$) δ 183.84, 169.61, 153.25, 142.83, 141.87, 138.32, 136.49, 135.94, 133.07, 125.69, 124.50, 91.79, 61.76, 35.20, and 14.42.

Benzyl 4-((4-(5-bromo-4-(2-ethoxy-2-oxoethyl) thiophene-2-carbonyl)-2-nitrophenyl)ethynyl)benzoate (3)

A solution of 2 (952 mg, 1.82 mmol), benzyl 4-ethynylbenzoate (472 mg, 2.00 mmol), $Pd(PPh_3)_2Cl_2$ (128 mg, 0.18 mmol), $K_2CO_3$ (250 mg, 1.81 mmol), and $Et_3N$ (238 mg, 2.36 mmol) in DMF (4 mL) was stirred for 24 hours at room temperature. Water (5 mL) was added to the mixture and then extracted with EtOAc (3×30 mL). The combined organic layer was washed with brine, dried over $MgSO_4$, and concentrated in vacuo. MPLC purification (Hex:EtOAc/5:1) of the residue gave 3 as a solid foam (600 mg, 52%). $^1H$ NMR (400 MHz, $CDCl_3$) δ 8.55 (s, 1H), 8.11-8.06 (m, 3H), 7.87 (d, J=8.0 Hz, 1H), 7.68 (d, J=8.0 Hz, 2H), 7.52 (s, 1H), 7.47-7.34 (m, 5H), 5.38 (s, 3H), 4.19 (q, J=7.2 Hz, 2H), 3.67 (s, 2H), and 1.28 (t, J=7.2 Hz, 3H); $^{13}C$ NMR (100 MHz, $CDCl_3$) δ 183.86, 169.64, 165.88, 149.62, 142.04, 137.57, 136.41, 135.95, 135.92, 135.39, 133.02, 132.40, 131.08, 130.02, 129.93, 128.91, 128.66, 128.55, 126.69, 125.60, 124.44, 122.06, 99.57, 84.06, 67.32, 61.77, 35.25, and 14.42.

Benzyl 4-(6-(5-bromo-4-(2-ethoxy-2-oxoethyl) thiophene-2-carbonyl)-1H-indol-2-yl)benzoate (4)

To a solution of 3 (450 mg, 0.71 mmol) in EtOAc (10 mL) was added stannous chloride dihydrate (642 mg, 2.84 mmol). The resulting mixture was refluxed for one hour under $N_2$. The reaction mixture was poured onto ice (5 g), and basified with saturated $NaHCO_3$ solution to pH 8. The white milky mixture was filtered through a Celite pad to remove tin oxides. The organic layer from the filtrate was dried over $MgSO_4$, filtered, and then concentrated in vacuo. MPLC purification (Hex:EtOAc/4:1) of the crude product gave the desired intermediate benzyl 4-((2-amino-4-(5-bromo-4-(2-ethoxy-2-oxoethyl)thiophene-2-carbonyl)phenyl)ethynyl) benzoate as a yellow foam (450 mg, 95%). $^1H$ NMR (400 MHz, $CDCl_3$) δ 8.07 (d, J=8.0 Hz, 2H), 7.60 (d, J=8.0 Hz, 2H), 7.51-7.36 (m, 7H), 7.22-7.18 (m, 2H), 5.38 (s, 2H), 4.18 (q, J=7.2 Hz, 2H), 3.64 (s, 2H), and 1.27 (t, J=7.2 Hz, 3H); $^{13}C$ NMR (100 MHz, $CDCl_3$) δ 186.72, 169.84, 166.01, 148.31, 143.21, 138.58, 136.12, 136.05, 135.39, 132.55, 131.71, 130.02, 129.98, 128.90, 128.62, 128.51, 127.71, 122.93, 118.70, 114.66, 111.47, 96.66, 88.41, 67.21, 61.63, 53.75, 35.32, and 14.44.

To a 25 mL flask containing freshly distilled toluene (10 mL) was added benzyl 4-((2-amino-4-(5-bromo-4-(2-ethoxy-2-oxoethyl)thiophene-2-carbonyl)phenyl)ethynyl) benzoate (100 mg, 0.17 mmol) and indium tribromide (24 mg, 0.06 mmol) under $N_2$. The resulting mixture was refluxed for one hour. The solvent was removed in vacuo. MPLC purification (Hex:EtOAc/4:1) of the crude product gave 4 as a yellow solid (76 mg, 76%). $^1H$ NMR (400 MHz, $CDCl_3$) δ 9.50 (brs, 1H), 8.16 (d, J=8.0 Hz, 2H), 8.02 (s, 1H), 7.82 (d, J=8.4 Hz, 2H), 7.65 (q, J=8.4 Hz, 2H), 7.55 (s, 1H), 7.48-7.34 (m, 5H), 6.98 (s, 1H), 5.39 (s, 2H), 4.19 (q, J=7.2 Hz, 2H), 3.64 (s, 2H), and 1.28 (t, J=7.2 Hz, 3H); $^{13}C$ NMR (100 MHz, $CDCl_3$) δ 187.53, 170.09, 166.24, 143.98, 140.75, 136.91, 136.16, 136.07, 135.92, 135.09, 132.96, 131.53, 130.74, 129.74, 128.90, 128.59, 128.53, 125.56, 122.10, 121.94, 120.81, 113.74, 101.86, 67.14, 61.66, 35.37, and 14.43.

Benzyl 4-(6-(5-bromo-4-(2-ethoxy-2-oxoethyl) thiophene-2-carbonyl)-1-(4-(1,3-dioxoisoindolin-2-yl)butyl)-1H-indol-2-yl)benzoate (5)

To a stirred solution of 4 (76 mg, 0.13 mmol), N-(4-bromobutyl)-phthalimide (71 mg, 0.25 mmol) in 10 mL $CH_3CN$, CsF (96 mg, 0.63 mmol) was added. The resulting mixture was refluxed for 5 hours and then concentrated in vacuo. MPLC purification (Hex:EtOAc/4:1) of the residue gave 5 as a yellow amorphous solid (60 mg, 69%). $^1H$ NMR (400 MHZ, $CDCl_3$) δ 8.13 (d, J=8.4 Hz, 2H), 7.96 (s, 1H), 7.74-7.35 (m, 14H), 6.62 (s, 1H), 5.39 (s, 2H), 4.30 (t, J=7.2 Hz, 2H), 4.16 (q, J=7.2 Hz, 2H), 3.66 (s, 2H), 3.49 (t, J=6.8 Hz, 2H), 1.70-1.66 (m, 2H), 1.48-1.45 (m, 2H), and 1.26 (t, J=7.2 Hz, 3H); $^{13}C$ NMR (100 MHz, $CDCl_3$) δ 187.27, 169.94, 168.47, 166.11, 144.12, 143.76, 137.30, 137.13, 136.11, 135.81, 135.11, 134.22, 132.06, 131.88, 131.24, 130.37, 130.20, 129.31, 128.90, 128.61, 128.53, 123.43, 121.63, 120.86, 112.60, 104.17, 67.17, 61.49, 43.90, 37.22, 35.32, 27.38, 25.80, and 14.43.

Benzyl 4-(1-(4-(1,3-dioxoisoindolin-2-yl)butyl)-6-(4-(2-ethoxy-2-oxoethyl)-5-(3-hydroxy phenyl) thiophene-2-carbonyl)-1H-indol-2-yl)benzoate (6)

A mixture of 5 (60 mg, 0.075 mmol), $Pd(PPh_3)_4$ (17 mg, 0.015 mmol), CsF (34 mg, 0.22 mmol), 3-hydroxyphenylboronic acid (16 mg, 0.12 mmol), and $H_2O$ (80 μL) in DME (8 mL) was degassed with $N_2$ for 10 minutes and then refluxed. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex:EtOAc/5:1) of the residue gave 6 as a yellow amorphous solid (50 mg, 82%). $^1H$ NMR (400 MHz, $CDCl_3$) δ 8.13 (d, J=8.0 Hz, 2H), 8.04 (s, 1H), 7.74-7.61 (m, 7H), 7.56 (d, J=8.0 Hz, 2H), 7.49-7.26 (m, 6H), 7.13 (s, 1H), 7.03 (d, J=7.6 Hz, 1H), 6.92 (d, J=8.4 Hz, 1H), 6.63 (s, 1H), 5.40 (s, 2H), 4.32 (t, J=7.2 Hz, 2H), 4.16-4.06 (m, 2H), 3.72 (s, 2H), 3.51 (t, J=6.8 Hz, 2H), 1.72-1.69 (m, 2H), 1.49-1.46 (m, 2H), and 1.26 (t, J=7.2 Hz, 3H); $^{13}C$ NMR (100 MHz, $CDCl_3$) δ 188.62, 171.45, 168.65, 166.21, 157.16, 149.47, 143.69, 141.59, 138.00, 137.26, 137.23, 136.09, 134.28, 131.99, 131.82, 130.66, 130.37, 130.33, 130.12, 129.33, 128.90, 128.62, 128.53, 123.49, 121.88, 121.13, 120.87, 116.54, 116.46, 112.82, 104.20, 67.20, 61.46, 43.92, 37.36, 34.81, 27.45, 25.84, and 14.42.

4-(1-(4-(1,3-Dioxoisoindolin-2-yl)butyl)-6-(4-(2-ethoxy-2-oxoethyl)-5-(3-hydroxyphenyl)thiophene-2-carbonyl)-1H-indol-2-yl)benzoic acid (7)

A mixture of 6 (50 mg, 0.061 mmol) and 10% Pd—C (20 mg) in MeOH (8 mL) and EtOAc (3 mL) was stirred under 1 atm $H_2$ atmosphere until 6 was no longer detected by TLC. The resulting solution was filtered and concentrated in vacuo to give 7 as a yellow amorphous solid (39 mg, 88%). $^1H$ NMR (400 MHz, $CDCl_3$) δ 8.16 (d, J=8.4 Hz, 2H), 8.06 (s, 1H), 7.77-7.65 (m, 7H), 7.59 (d, J=8.0 Hz, 2H), 7.29 (t, J=8.0 Hz, 2H), 7.11 (s, 1H), 7.03 (d, J=7.6 Hz, 1H), 6.93 (d, J=8.0 Hz, 1H), 6.66 (s, 1H), 4.34 (brt, 2H), 4.15 (q, J=7.2 Hz, 2H), 3.72 (s, 2H), 3.52 (brt, 2H), 1.72-1.65 (m, 2H), 1.51-1.47 (m, 2H), and 1.24 (t, J=7.2 Hz, 3H); $^{13}C$ NMR (100 MHz, $CDCl_3$) δ 188.63, 171.67, 170.53, 168.73, 157.13, 149.52, 143.65, 141.52, 137.98, 137.73, 137.34, 134.34, 134.25, 131.97, 131.89, 131.84, 130.82, 130.56, 130.40, 129.55, 129.37, 123.54, 121.93, 121.17, 120.89, 116.52, 116.44, 112.83, 104.34, 61.59, 43.97, 37.38, 34.90, 27.46, 25.84, and 14.40.

Ethyl 2-(5-(2-(4-(bis(10-(1,3-dioxoisoindolin-2-yl)decyl)carbamoyl)phenyl)-1-(4-(1,3-dioxoisoindolin-2-yl)butyl)-1H-indole-6-carbonyl)-2-(3-hydroxyphenyl)thiophen-3-yl)acetate (8)

A mixture of 7 (54 mg, 0.074 mmol), BOP (43 mg, 0.097 mmol), NMM (11 mg, 0.109 mmol), and 2,2'-(10,10'-azanediylbis(decane-10,1-diyl))diisoindoline-1,3-dione (12) (65 mg, 0.110 mmol) in DMF (4 mL) was stirred at room temperature under $N_2$. When the reaction was over by TLC monitoring, the mixture was poured into $H_2O$ (10 mL) and then extracted with 70 mL $Et_2O$. The organic layer was washed with brine (2×10 mL), dried over $MgSO_4$, and then concentrated in vacuo. MPLC purification (Hex/EtOAc 5:1) of the residue gave 8 as a yellow amorphous solid (52 mg, 54%). $^1H$ NMR (400 MHz, $CDCl_3$) δ 8.01 (s, 1H), 7.84-7.60 (m, 15H), 7.53 (d, J=7.6 Hz, 2H), 7.47 (d, J=8.0 Hz, 2H), 7.28-7.24 (m, 1H), 7.07 (s, 1H), 7.00 (d, J=7.6 Hz, 1H), 6.91 (d, J=7.6 Hz, 1H), 6.58 (s, 1H), 4.30 (brt, 2H), 4.12 (q, J=7.2 Hz, 2H), 3.69-3.55 (m, 6H), 3.50 (t, J=6.4 Hz, 4H) 3.24 (brt, 2H), and 1.80-1.18 (m, 39H); $^{13}C$ NMR (100 MHz, $CDCl_3$) δ 188.37, 171.41, 171.32, 168.74, 168.58, 157.33, 149.24, 144.13, 141.61, 137.77, 137.33, 136.98, 134.29, 134.23, 134.12, 133.48, 132.34, 132.05, 131.84, 131.58, 130.60, 130.22, 129.54, 127.26, 123.48, 123.38, 121.78, 120.97, 120.62, 116.56, 116.42, 112.74, 103.64, 61.37, 49.42, 45.18, 43.79, 38.29, 38.21, 37.32, 34.79, 29.76, 29.66, 29.60, 29.39, 29.30, 28.96, 28.83, 27.74, 27.47, 27.31, 27.08, 27.02, 26.81, 25.84, and 14.41.

4-(1-(4-aminobutyl)-6-(4-(2-(hydroxyamino)-2-oxoethyl)-5-(3-hydroxyphenyl)thiophene-2-carbonyl)-1H-indol-2-yl)-N,N-bis(10-aminodecyl)benzamide (E1c)

To a stirred solution of 8 (26 mg, 0.020 mmol) in THF/MeOH (1 mL/1 mL), 1.5 mL of 50% aqueous $NH_2OH$ was added, followed by a catalytic amount of KCN (CAUTION: KCN is highly toxic and must be handled with extreme care by trained personnel). The resulting mixture was stirred for 24 hours at room temperature, and then filtered through a short Celite column. HPLC purification of the filtrate gave E1c•$(TFA)_3$ as a yellow amorphous solid (11 mg, 44%). HPLC purification conditions: Agilent ZORBAX RX-C18 5 mm, 4.6×250 mm, eluting with linear gradient of 80% of solution A (1000 mL of $H_2O$ and 1 mL of TFA) to 100% of solution solution B (100 mL of $H_2O$, 900 mL of $CH_3CN$, and 1 mL of TFA) over 120 minutes, and flow rate of 1.0 mL/min with a retention time of 37.87 minutes for E1c•$(TFA)_3$. $^1H$ NMR (400 MHz, $CD_3OD$) δ 8.12 (s, 1H), 7.82 (s, 1H), 7.75 (d, J=8.0 Hz, 1H), 7.70 (d, J=8.0 Hz, 2H), 7.66 (d, J=8.0 Hz, 1H), 7.53 (d, J=8.0 Hz, 2H), 7.32 (t, J=8.0 Hz, 1H), 7.00 (d, J=8.0 Hz, 1H), 6.97 (s, 1H), 6.89 (d, J=8.0 Hz, 1H), 6.72 (s, 1H), 4.42 (t, J=6.6 Hz, 2H), 3.55-3.51 (m, 4H), 3.30 (overlapped with $CD_3OD$, 2H), 2.91 (t, J=7.4 Hz, 2H), 2.81 (t, J=7.4 Hz, 4H), and 1.82-1.54 (m, 36H); $^{13}C$ NMR ($CD_3OD$) δ 189.12, 172.16, 169.15, 161.49 (q, $CF_3CO_2H$, $^2J_{CF}$=35.1 Hz), 158.00, 149.17, 144.03, 141.68, 137.61, 137.14, 137.00, 134.12, 133.72, 132.02, 131.39, 131.31, 130.05, 129.47, 126.97, 120.84, 120.21, 116.90 (q, $CF_3CO_2H$, $^1J_{CF}$=288.1 Hz), 115.96, 115.91, 113.05, 103.52, 49.26, 45.19, 43.49, 39.55, 39.49, 39.17, 32.26, 29.45, 29.38, 29.33, 29.07, 28.92, 28.36, 27.42, 27.38, 27.22, 26.94, 26.30, and 24.74; IR $cm^{-1}$ 3109.2, 1674.9, 1200.9, and 1143.7; LRMS-El m/z 894 (94%, $[M+H^+]$), 328 (100%); HRMS-ESI calculated for $C_{52}H_{74}N_6O_5S$ $[M+2H^+]$ 447.2715. found 447.2718.

2-(10-Bromodecyl)isoindoline-1,3-dione (10)

To a stirred solution of 1,10-dibromodecane (9) (16.2 g, 54 mmol) in acetone (100 mL) was added potassium phthalimide (5.00 g, 27.0 mmol). The resulting mixture was refluxed for 12 hours. The reaction mixture was cooled to room temperature and the solvent was removed in vacuo. MPLC purification of the residue (Hexanes:EtOAc/70:30) gave 10 as a colorless oily liquid (7.5 g, 76%). $^1H$ NMR (400 MHz, $CDCl_3$) δ 7.85-7.83 (m, 2H), 7.71-7.69 (m, 2H), 3.67 (t, J=7.2 Hz, 2H), 3.39 (t, J=6.8 Hz, 2H), 1.85-1.78 (m, 2H), 1.70-1.60 (m, 2H), and 1.45-1.20 (m, 12H).

2,2'-(10,10'-(Benzylazanediyl)bis(decane-10,1-diyl))diisoindoline-1,3-dione (11)

To a stirred solution of 10 (7.5 g, 20.5 mmol) in acetonitrile (200 mL) was added $K_2CO_3$ (5.36 g, 38.8 mmol) and benzyl amine (1.04 g, 9.7 mmol). The resulting solution was refluxed for 48 hours. The reaction mixture was cooled to room temperature, filtered and the filtrate was concentrated in vacuo. MPLC purification of the residue (Hexanes:EtOAc/70:30) gave 11 as a yellow viscous oil (5.67 g, 86%). $^1H$ NMR (400 MHz, $CDCl_3$) δ 7.86-7.80 (m, 4H), 7.73-7.67 (m, 4H), 7.32-7.18 (m, 5H), 3.67 (t, J=7.2 Hz, 4H), 3.52 (s, 2H), 2.36 (t, J=7.2 Hz, 4H), 1.70-1.60 (m, 4H), 1.47-1.38 (m, 4H), and 1.38-1.18 (m, 24H).

2,2'-(10,10'-azanediylbis(decane-10,1-diyl))diisoindoline-1,3-dione (12)

To a stirred solution of 11 (1.5 g, 2.4 mmol) in MeOH:EtOAc (1:1, 40 mL) was added 10% Pd—C (0.15 g). The resulting mixture was stirred at room temperature for 16 hours under a hydrogen balloon. The reaction mixture was filtered off and the filtrate was concentrated in vacuo. MPLC purification of the residue gave 12 as an amorphous white solid (1.17 g, 91%). $^1H$ NMR (400 MHz, $CD_3OD$) δ 7.85-7.78 (m, 8H), 3.65 (t, J=7.2 Hz, 4H), 2.95 (t, J=7.8 Hz, 4H), 1.70-1.60 (m, 8H), and 1.44-1.28 (m, 24H).

Example 8

Synthesis of E6b

E6b was synthesized according to the scheme in FIG. 15.

Methyl 1H-pyrrole-2-carboxylate (2)

To a stirred solution of 2-(trichloroacetyl)pyrrole (10.00 g, 47.1 mmol) in MeOH (20 mL) was added $K_2CO_3$ (8.44 g, 61.2 mmol). The resulting mixture was stirred under reflux for 3 hours, cooled to room temperature and filtered. The filtrate was concentrated in vacuo to give 2 as a dark brown solid (5.50 g, 93%). $^1H$ NMR ($CDCl_3$) δ 9.49 (bs, 1H), 6.92-6.96 (m, 2H), 6.26 (m, 1H), and 3.86 (s, 3H); $^{13}C$ NMR ($CDCl_3$) δ 162.05, 123.33, 122.79, 115.56, 110.66, and 51.72.

Methyl 4-formyl-1H-pyrrole-2-carboxylate (3)

To a solution of 2 (4.50 g, 36.0 mmol) in $CH_2Cl_2$:$CH_3NO_2$ (1:1, 40 mL) at −40° C., was added $AlCl_3$ (12.48 g, 93.6 mmol) followed by ∝,∝-dichloromethyl methyl ether (4.15 mL, 46.8 mmol). The resulting mixture was allowed to warm to room temperature and stirred for 16 hours. The reaction mixture was slowly poured onto ice (10.00 g) and allowed to warm to room temperature. The aqueous phase was extracted with $CH_2Cl_2$ (3×50 mL). The combined organic layer was dried over anhydrous $MgSO_4$, filtered and concentrated to give 3 as a dark brown solid (3.40 g, 62%). $^1$H NMR ($CDCl_3$) δ 10.32 (bs, 1H), 9.83 (s, 1H), 7.59 (d, J=1.6 Hz, 1H), 7.30 (s, 1H), and 3.88 (s, 3H); $^{13}$C NMR ($CDCl_3$) δ 186.07, 161.71, 129.15, 127.71, 124.99, 114.56, and 52.34.

Methyl 4-formyl-5-iodo-1H-pyrrole-2-carboxylate (4)

To a stirred solution of 3 (3.40 g, 22.2 mmol) in $CHCl_3$ (20 mL) at 0° C. was added $CF_3COOAg$ (5.40 g, 24.4 mmol) followed by $I_2$ (3.10 g, 24.4 mmol). The resulting mixture was stirred for 16 hours in the dark at room temperature. The reaction mixture was filtered through Celite and the filtrate was washed with saturated aqueous solution of $Na_2S_2O_3$ (2×20 mL). The organic layer was dried over anhydrous $MgSO_4$, filtered and concentrated in vacuo. MPLC purification ($CH_2Cl_2$:diethyl ether/95:5) of the residue gave 4 as a white solid (0.72 g, 32% based on the recovered starting material). Along with 4, two minor compounds methyl-4-formyl-5-iodo-1H-pyrrole-2-carboxylate, methyl 4-formyl-3,5-diiodo-1H-pyrrole-2-carboxylate and the starting material 3 were also isolated. $^1$H NMR (DMSO-$d_6$) δ 13.30 (bs, 1H), 9.52 (s, 1H), 7.04 (s, 1H), and 3.77 (s, 3H); $^{13}$C NMR (DMSO-$d_6$) δ 187.13, 160.36, 128.78, 127.79, 115.58, 87.40, and 52.42.

Methyl 1-benzyl-4-formyl-5-iodo-1H-pyrrole-2-carboxylate (5)

To a stirred solution of 4 (0.72 g, 2.6 mmol) in acetone (20 mL) was added $K_2CO_3$ (0.71 g, 5.1 mmol). The resulting mixture was stirred for 30 minutes at room temperature. Benzyl bromide (0.46 mL, 3.8 mmol) was added dropwise to the reaction mixture and was then refluxed for 16 hours. The reaction mixture was cooled to room temperature, concentrated and partitioned between ethyl acetate and water. The combined organic layer was dried over anhydrous $MgSO_4$, filtered and then concentrated in vacuo. MPLC purification (Hexanes:EtOAc/80:20) of the residue gave 5 as a white solid (0.85 g, 90%). $^1$H NMR ($CDCl_3$) δ 9.66 (s, 1H), 7.50 (s, 1H), 7.24-7.25 (m, 3H), 6.98 (d, J=7.6 Hz, 2H), 5.75 (s, 2H), and 3.72 (s, 3H); $^{13}$C NMR ($CDCl_3$) δ 186.98, 160.33, 136.43, 128.97, 128.22, 127.84, 127.10, 126.59, 119.32, 92.81, 52.81, and 52.11.

Methyl 1-benzyl-4-formyl-5-(3-hydroxy-3,3-diphenylprop-1-ynyl)-1H-pyrrole-2-carboxylate (6)

A solution of 5 (0.47 g, 1.3 mmol), 1,1-diphenylprop-2-yn-1-ol (0.66 g, 3.2 mmol), CuI (0.05 g, 0.3 mmol), $Pd(PPh_3)_2Cl_2$ (0.18 g, 0.3 mmol), $PPh_3$ (0.07 g, 0.3 mmol), and $Et_3N$ (4 mL) in anhydrous DMF (4 mL) was stirred for 16 hours at 70° C. under $N_2$ atmosphere. The reaction mixture was then partitioned between water and EtOAc. The combined organic layer was dried over $MgSO_4$, filtered and concentrated in vacuo. MPLC purification (Hexanes:EtOAc/80:20) of the residue gave 6 as a pale yellow solid (0.49 g, 87%). $^1$H NMR ($CDCl_3$) δ 9.88 (s, 1H), 7.50-7.52 (m, 4H), 7.36 (s, 1H), 7.24-7.30 (m, 8H), 7.04 (m, 2H), 5.69 (s, 2H), 3.80 (s, 3H), and 3.65 (s, 1H); $^{13}$C NMR ($CDCl_3$) δ 185.16, 160.72, 144.07, 136.84, 128.91, 128.72, 128.33, 127.91, 127.79, 127.05, 126.23, 124.96, 116.97, 103.35, 75.37, 75.27, 52.15, and 50.38.

1-Benzyl-4-formyl-5-(3-hydroxy-3,3-diphenylprop-1-ynyl)-1H-pyrrole-2-carboxylic acid (7)

To a solution of 6 (0.49 g, 1.1 mmol) in MeOH (20 mL) and water (6 mL) was added KOH (0.18 g, 3.3 mmol) and stirred at 60° C. for 2 hours. The solvent was then removed in vacuo. The residue obtained was acidified with 2N HCl to pH 2-3 and extracted with EtOAc (3×15 mL). The combined organic layer was dried over $MgSO_4$, filtered and then concentrated in vacuo to give 7 as a light brown solid. The crude product was subjected to the next reaction without further purification. $^1$H NMR ($CDCl_3$) δ 9.82 (s, 1H), 7.50-7.52 (m, 4H), 7.45 (s, 1H), 7.21-7.26 (m, 7H), 7.02-7.03 (m, 2H), and 5.64 (s, 2H).

1-Benzyl-N-(3,5-bis(6-(1,3-dioxoisoindolin-2-yl)hexyl)-4-(7-(1,3-dioxoisoindolin-2-yl)heptyloxy)phenyl)-4-formyl-5-(3-hydroxy-3,3-diphenylprop-1-ynyl)-1H-pyrrole-2-carboxamide (8)

A solution of 7 (0.20 g, 0.46 mmol), 14 (0.45 g, 0.55 mmol), BOP (benzotriazol-1-yloxytris(dimethylamino)phosphonium hexafluorophosphate) (0.41 g, 0.92 mmol), HOBt (1-hydroxybenzotriazole) (0.13 g, 0.92 mmol) in anhydrous DMF (3 mL) and NMM (N-methylmorpholine) (2 mL) was stirred at room temperature for 16 hours. The reaction mixture was partitioned between water (20 mL) and EtOAc (20 mL). The aqueous layer was washed with EtOAc (2×20 mL). The combined organic layer was dried over $MgSO_4$, filtered and then concentrated in vacuo. MPLC purification (Hexanes:EtOAc/50:50) of the residue gave 8 as a pale yellow oil. (0.11 g, 18%). $^1$H NMR ($CDCl_3$) δ 9.92 (s, 1H), 8.08 (s, 1H), 7.79-7.83 (m, 6H), 7.67-7.70 (m, 6H), 7.45-7.51 (m, 4H), 7.19-7.19 (m, 11H), 7.05-7.06 (m, 2H), 5.77 (s, 2H), 3.61-3.69 (m, 8H), 2.55-2.59 (m, 4H), and 1.25-1.76 (m, 26H).

Ethyl 3-(1-benzyl-5-(3,5-bis(6-(1,3-dioxoisoindolin-2-yl)hexyl)-4-(7-(1,3-dioxoisoindolin-2-yl)heptyloxy)phenylcarbamoyl)-2-(3-hydroxy-3,3-diphenylprop-1-ynyl)-1H-pyrrol-3-yl)acrylate (9)

To a stirred solution of 8 (0.11 g, 0.09 mmol) in benzene (20 mL) was added (ethoxycarbonylmethylene)triphenyl phosphorane (0.08 g, 0.23 mmol). The resulting mixture was stirred under reflux for 16 hours. The reaction mixture was cooled to room temperature and the solvent was removed in vacuo. MPLC purification (Hexanes:EtOAc/50:50) of the residue gave 9 as a pale yellow oily liquid (0.09 g, 73%). $^1$H NMR ($CDCl_3$) δ 8.01 (s, 1H), 7.76-7.82 (m, 6H), 7.62-7.69 (m, 7H), 7.50-7.51 (m, 4H), 7.16-7.31 (m, 10H), 7.01-7.02 (m, 2H), 6.91 (s, 1H), 6.24 (d, J=16.0 Hz, 1H), 5.68 (s, 2H), 4.17 (q, J=6.8 Hz, 2H), 3.62-3.69 (m, 8H), 3.31 (s, 1H), 2.55 (t, J=7.2 Hz 4H), 1.58-1.77 (m, 12H), and 1.23-1.36 (m, 17H).

Ethyl 3-(1-benzyl-5-(3,5-bis(6-(1,3-dioxoisoindolin-2-yl)hexyl)-4-(7-(1,3-dioxoisoindolin-2-yl)heptyloxy)phenylcarbamoyl)-2-(3-hydroxy-3,3-diphenylprop-1-ynyl)-1H-pyrrol-3-yl)propanoate (10)

To a stirred solution of 9 (0.07 g, 0.06 mmol) in EtOAc (20 mL) was added dry powdered 10% Pd—C (0.007 g). The resulting mixture was stirred at room temperature for 48 hours under $H_2$ balloon. Pd—C was filtered off and the filtrate was concentrated to give 10 as colorless oil (0.07 g, 80%). The crude product was subjected to the next reaction without further purification. $^1$H NMR ($CDCl_3$) δ 7.78-7.80 (m, 6H), 7.65-7.69 (m, 7H), 7.14-7.33 (m, 14H), 6.76 (d, J=7.2 Hz, 1H), 6.61 (s, 1H), 5.52 (s, 2H), 4.05 (q, J=6.8 Hz, 2H), 3.62-3.67 (m, 8H), 2.62 (m, 2H), 2.45-2.54 (m, 8H), 2.19-2.22 (m, 2H), 1.56-1.67 (m, 12H), and 1.22-1.35 (m, 17H), 1-Benzyl-N-(3,5-bis(6-(1,3-dioxoisoindolin-2-yl) hexyl)-4-(7-(1,3-dioxoisoindolin-2-yl)heptyloxy) phenyl)-5-(3-hydroxy-3,3-diphenylprop-1-ynyl)-4-(3-(hydroxyamino)-3-oxopropyl)-1H-pyrrole-2-carboxamide trifluoroacetic acid salt (E6b•(TFA)$_3$)

To a stirred solution of 10 (0.07 g, 0.05 mmol) in MeOH:THF (1:1, 4 mL) was added 50% aqueous hydroxylamine (4 mL) followed by catalytic amount of KCN (CAUTION: KCN is highly toxic and must be handled with extreme care by trained personnel). The resulting mixture was stirred at 35° C. for 24 hours. The solvent was removed under vacuum and the residue was subjected to HPLC for purification to give E6b•(TFA)$_3$ as colorless oil (0.019 g, 28%). HPLC purification condition: Phenomenex hyperclone 5μ, C18, 4.60×250 mm, eluting with linear gradient of 20% of solution B to 100% of solution B (solution A is 1000 mL of $H_2O$ and 1 mL of TFA and solution B is 100 mL of $H_2O$, 900 mL of $CH_3CN$ and 1 mL of TFA) over 20 minutes, and a flow rate of 1.0 mL/min with a retention time of 12.62 min for E6b•(TFA)$_3$. 10.35 (s, 1H), 9.48 (s, 1H), 7.38-7.40 (bs, 6H), 7.32 (s, 2H), 7.13-7.27 (m, 9H), 6.89 (s, 1H), 6.67-6.69 (d, J=7.2 Hz, 2H), 5.51 (s, 2H), 3.62 (t, J=6.0 Hz, 2H), 2.73-2.76 (m, 6H), 2.45-2.48 (m, 6H merged with DMSO-$d_6$), 2.29 (m, 4H), 2.16 (t, J=6.8 Hz, 2H), 1.67 (t, J=7.2 Hz, 2H), 1.42-1.49 (m, 12H), and 1.13-1.31 (m, 12H).

1,3-dibromo-2-(7-bromoheptyloxy)-5-nitrobenzene (11)

To a solution of 2,6-diiodo-4-nitrophenol (2.00 g, 5.13 mmol) in acetonitrile (50 mL) was added potassium carbonate (1.42 g, 10.27 mmol). The resulting mixture was stirred for 0.5 hours under reflux conditions. To this was added 1,7-dibromoheptane (3.98 g, 15.43 mmol) and stirring continued stirring for another 36 hours at 90° C. The reaction mixture was cooled to room temperature and filtered through Celite. The filtrate was concentrated in vacuo. MPLC purification (Hexanes:EtOAc/80:20) of the residue gave 11 as a yellow oil (1.50 g, 52%). $^1$H NMR ($CDCl_3$) δ 8.63 (s, 2H), 4.13 (t, J=6.4 Hz, 2H), 3.43 (t, J=6.8 Hz, 2H), 1.87-1.96 (m, 4H), and 1.44-1.61 (m, 2H).

2-(6-(2,6-dibromo-4-nitrophenoxy)heptyl)isoindoline-1,3-dione (12)

To a solution of 11 (1.33 g, 2.34 mmol) in acetone (30 mL) was added potassium phthalimide (0.56 g, 3.05 mmol). The resulting mixture was stirred for 24 hours under reflux conditions. The reaction mixture was cooled to room temperature and filtered through Celite. The filtrate was concentrated in vacuo. MPLC purification (Hexanes:EtOAc/80:20) of the residue gave 12 as a white amorphous solid (1.18 g, 80%). $^1$H NMR ($CDCl_3$) δ 8.63 (s, 2H), 7.83-7.85 (m, 2H), 7.70-7.72 (m, 2H), 4.02 (t, J=6.4 Hz, 2H), 3.70 (t, J=7.2 Hz, 2H), 1.91-1.95 (m, 2H), 1.69-1.73 (m, 2H), 1.55-1.58 (m, 2H), and 1.40-1.46 (m, 2H).

2,2'-(6,6'-(2-(7-(1,3-dioxoisoindolin-2-yl)heptyloxy)-5-nitro-1,3-phenylene)bis(hex-5-yne-6,1-diyl))di-isoindoline-1,3-dione (13)

A solution of 12 (0.50 g, 0.79 mmol) in anhydrous DMF (10 mL) was added 2-(hex-5-ynyl)isoindoline-1,3-dione (0.54 g, 2.38 mmol), $Cs_2CO_3$ (0.39 g, 1.18 mmol) and $Pd(OAc)_2$ (0.02 g, 0.09 mmol). The resulting mixture was flushed with $N_2$ and stirred for 2 hours at room temperature. The reaction mixture was then partitioned between water (20 mL) and EtOAc (20 mL). The aqueous layer was washed with EtOAc (2×20 mL). The combined organic layer was dried over $MgSO_4$, filtered and concentrated in vacuo. MPLC purification (Hexanes:EtOAc/50:50) of the residue gave 13 as a pale yellow liquid (0.64 g, 97%). $^1$H NMR ($CDCl_3$) δ 8.07 (s, 2H), 7.81 (m, 4H), 7.68-7.70 (m, 4H), 4.27 (t, 2H), 3.72 (t, 4H), 3.56 (t, 2H), 2.50 (t, 4H), 1.86 (m, 4H), 1.52-1.78 (m, 8H), 1.50-1.58 (m, 2H), and 1.34-1.42 (m, 2H).

2,2'-(6,6'-(5-amino-2-(7-(1,3-dioxoisoindolin-2-yl) heptyloxy)-1,3-phenylene)bis(hexane-6,1-diyl))di-isoindoline-1,3-dione (14)

To a stirred solution of 13 (0.75 g, 0.90 mmol) in EtOAc (50 mL) was added dry powdered 10% Pd—C (0.08 g). The resulting mixture was stirred at room temperature for 12 hours under a $H_2$ balloon. Pd—C was filtered off and the filtrate was concentrated to give 14 as pale yellow oil (0.70 g, 92%). The crude product was subjected to the next reaction without further purification. $^1$H NMR of the crude product is as follows. $^1$H NMR ($CDCl_3$) δ 7.81-7.82 (m, 4H), 7.68-7.70 (m, 4H), 6.41 (s, 2H), 3.60-3.69 (m, 8H), 2.46-2.50 (m, 4H), and 1.37-1.72 (m, 26H).

Example 9

Three-Dimensional Models of E4, E7-E10

The three-dimensional models BoNTAe in complex with inhibitors of Formula (IA), (IIA), (IIIA), and (IVA) were generated according to the following protocol.

MMDS Docking. Multiple molecular dynamics simulations (MMDSs) were performed by using the PMEMD module of AMBER 8.0 (Pearlman D A, Case D A, Caldwell J W, Ross W S, Cheatham III T E, et al. (1995) *Comput Phys Commun* 91: 1-41) with the AMBER force field (frcmod.ff99sb) (Hornak V, Abel R, Okur A, Strockbine B, Roitberg A, et al. (2006) *Proteins: Structure, Function & Genetics* 65: 712-725). The topology and coordinate files were generated by the PREP, LINK, EDIT, and PARM modules of AMBER 5.0 (Pearlman D A, Case D A, Caldwell J W, Ross W S, Cheatham III T E, et al. (1995) *Comput Phys Commun* 91: 1-41).

All simulations used (1) a dielectric constant of 1.0, (2) the Berendsen coupling algorithm (Berendsen H J C, Postma J P M, van Gunsteren W F, Di Nola A, Haak J R (1984) *J Chem Phys* 81: 3684-3690), (3) a periodic boundary condition at a constant temperature of 300 K and a constant pressure of 1 atm with isotropic molecule-based scaling, (4) the Particle Mesh Ewald method to calculate long-range electrostatic interactions (Darden T A, York D M, Pedersen L G (1993) *J Chem Phys* 98: 10089-10092), (5) a time step of 1.0 fs, (6) the SHAKE-bond-length constraints applied to all the bonds involving the H atom, (7) saving the image closest to the middle of the "primary box" to the restart and trajectory files, (8) formatted restart file, and (9) default values of all other inputs of the PMEMD module. The atomic charges of the inhibitors were obtained according to the RESP procedure with ab initio calculations at the HF/6-31G*//HF/6-31G* level using Gaussian98 (Frisch M J, Trucks G W, Schlegel H B, Gill P M W, Johnson B G, et al. (1999) GAUSSIAN 98, Revision A.7. Gaussian, Inc Pittsburgh, Pa.).

The starting structure of inhibitor•BoNTAe was generated by (1) manually docking the inhibitor into the active site of the BoNTAe crystal structure (PDB code: 3BOO (Silvaggi N R, Wilson D, Tzipori S, Allen K N (2008) *Biochemistry* 47: 5736-5745)), (2) replacing the zinc ion with tetrahedral zinc ion (Park J G, Sill P C, Makiyi E F, Garcia-Sosa A T, Millard C B, et al. (2006) *Bioorg Med Chem* 14: 395-408; Pang Y-P (2001) *Proteins* 45: 183-189), and (3) inserting $Pro^{62}Pro^{63}Glu^{64}Ala^{65}Lys^{66}Gln^{67}$ to the gap between $Pro^{61}$ and $Val^{68}$ of the crystal structure. For BoNTAe, His223 and His227 were treated as HIN; His39, His230, and His269 were treated as HID; all other H is residues were treated as HIP; Glu261 and Glu351 were treated as GLH. A total of 39 crystallographically determined water molecules (named HOH) that were located inside the enzyme were included in the BoNTAe structure for simulations.

The water-containing inhibitor•BoNTAe complex was refined by energy minimization using a dielectric constant of 1.0 and 100 cycles of steepest-descent minimization followed by 100 cycles of conjugate-gradient minimization. The resulting complex was solvated with 12,098 TIP3P water molecules (named WAT) (Jorgensen W L, Chandreskhar J, Madura J D, Impey R W, Klein M L (1982) *J Chem Phys* 79: 926-935), leading to a system of 43,279 atoms. The WAT molecules were obtained from solvating the complex using a pre-equilibrated box of 216,000 TIP3P molecules, whose hydrogen atom charge was set to 0.4170, where any water molecule was removed if it had an oxygen atom closer than 2.2 Å to any solute atom or a hydrogen atom closer than 2.0 Å to any solute atom, or if it was located further than 9.0 Å along the x-, y-, or z-axis from any solute atom. The solvated complex system were energy-minimized for 100 cycles of steepest-descent minimization followed by 100 cycles of conjugate-gradient minimization to remove close van der Waals contacts in the system, then heated from 0 to 300 K at a rate of 10 K/ps under constant temperature and volume, and finally simulated at 300 K under constant temperature and pressure.

All simulations were carried out on 300 Apple Xservers each equipped with two G5 processors at a clock rate of 2.0/2.3 GHz, and each of these simulations used a unique seed number for initial velocities. Average structures were obtained by using the CARNAL module of AMBER 5.0. Cluster analyses were performed by using the PTRAJ module (Shao J, Tanner S W, Thompson N, Cheatham III T E (2007) *J Chem Theory Comput* 3: 2312-2334) of AMBER 10 according to a published protocol (Ekstrom F, Hornberg A, Artursson E, Hammarstrom L G, Schneider G, et al. (2009) PLoS ONE 4(6): e5957).

Twenty different 10-ns-long simulations were carried out for each inhibitor. For each of the 20 simulations, 200 instantaneous structures were saved at 5-ps intervals during the last 1-ns period. A most populated instantaneous structure, which was identified by the cluster analysis using a total of 4000 structures obtained from the 20 simulations, was subjected to a second-round MMDSs (20 different 10-ns simulations). The most populated instantaneous structure, which was identified by the cluster analysis using a total of 4000 structures obtained from the second-round simulations, is used as a model of an inhibitor-bound BoNTAe.

Model of E4•BoNTAe

Figure 7:
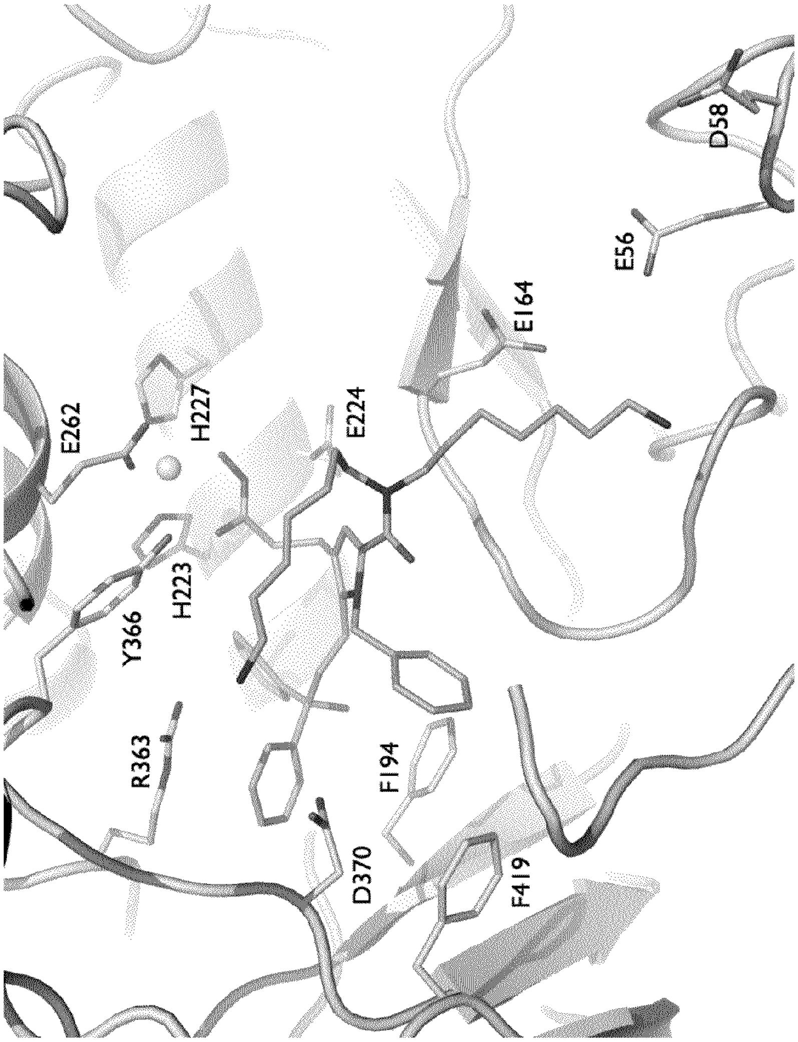
FIG. 7 shows a three-dimensional model of binding of E4 by BoNTAe.

As shown in FIG. 7, the hydroxamate group coordinates the zinc ion and has a hydrogen bond to E224, the diphenylmethyl group has cation-pi interactions with R363 and pi-pi interactions with Y366 and F194, the hydroxyl group has a hydrogen bond to D370, N-substituted benzyl group has pi-pi interactions with F419 and F194, one alkylamino group has an ionic interaction with D370, and the other alkylamino group has ionic interactions with E164, E56 and D58, indicating that E4 has a nanomolar affinity for BoNTAe.

Model of E7•BoNTAe

Figure 8:
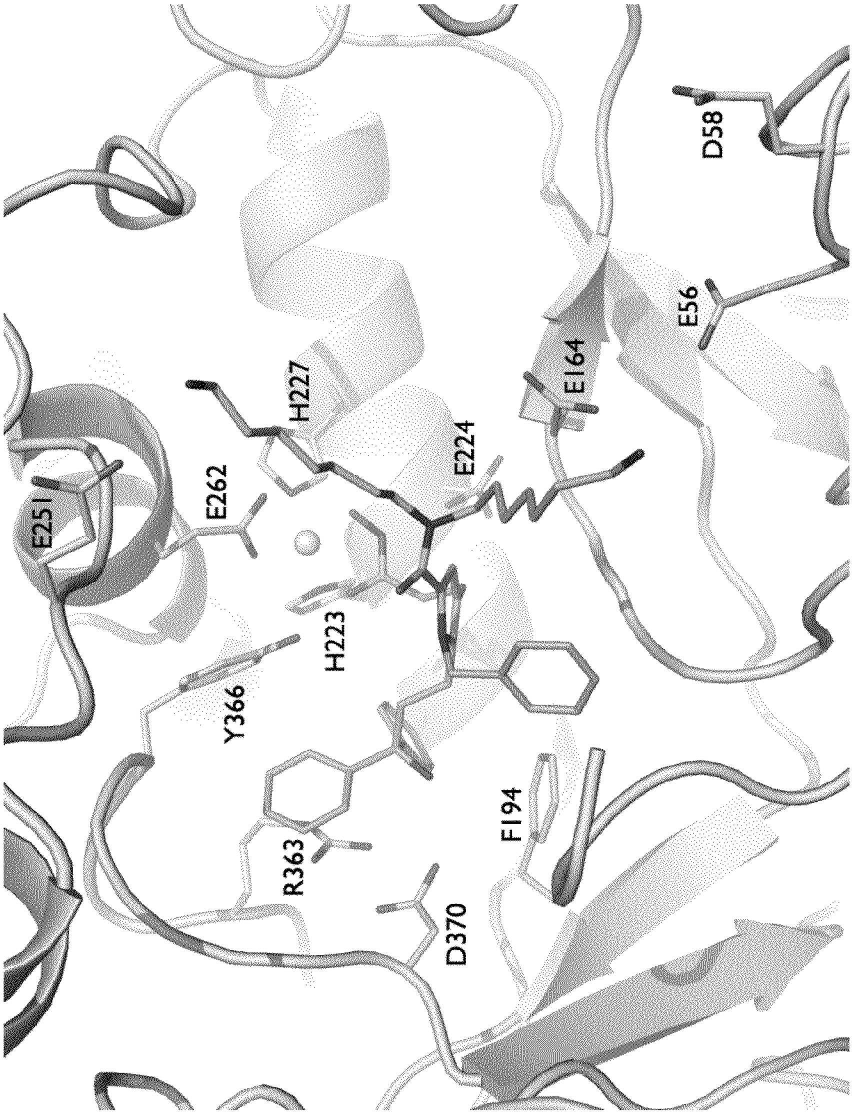
FIG. 8 shows a three-dimensional model of binding of E7 by BoNTAe.

As shown in FIG. 8, the hydroxamate group coordinates the zinc ion and has a hydrogen bond to E224, the diphenylmethyl group has cation-pi interactions with R363 and pi-pi interactions with Y366 and F194, the benzylic ammonium group has an ionic interaction with D370 and a cation-pi interaction with F194, N-substituted benzyl group has a pi-pi interaction with F194, one alkylamino group has an ionic interaction with E251, and the other alkylamino group has ionic interactions with E164, E56 and D58, indicating that E7 has a nanomolar affinity for BoNTAe.

Model of E8•BoNTAe

Figure 9:
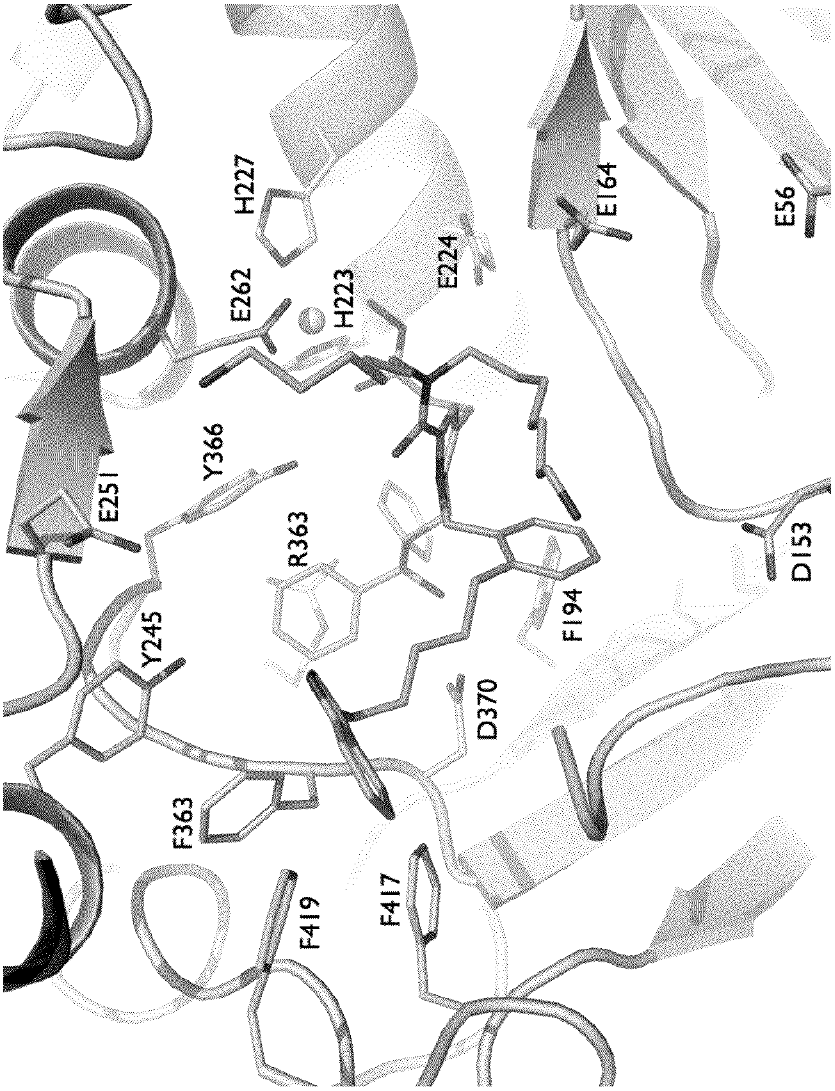
FIG. 9 shows a three-dimensional model of binding of E8 by BoNTAe.

As shown in FIG. 9, the hydroxamate group coordinates the zinc ion and has a hydrogen bond to E224, the diphenylmethyl group has cation-pi interactions with R363 and pi-pi interactions with Y366 and F194, the benzylic ammonium group has an ionic interaction with D370 and a cation-pi interaction with F194, N-substituted benzyl group has a pi-pi interaction with F194, the indole ring has pi-pi interactions with Y245, F363, F419, and F417, one alkylamino group has an ionic interaction with E251, and the other alkylamino group has ionic interactions with E164, E56 and D153, indicating that E8 has a nanomolar affinity for BoNTAe.

Model of E9•BoNTAe

Figure 10:
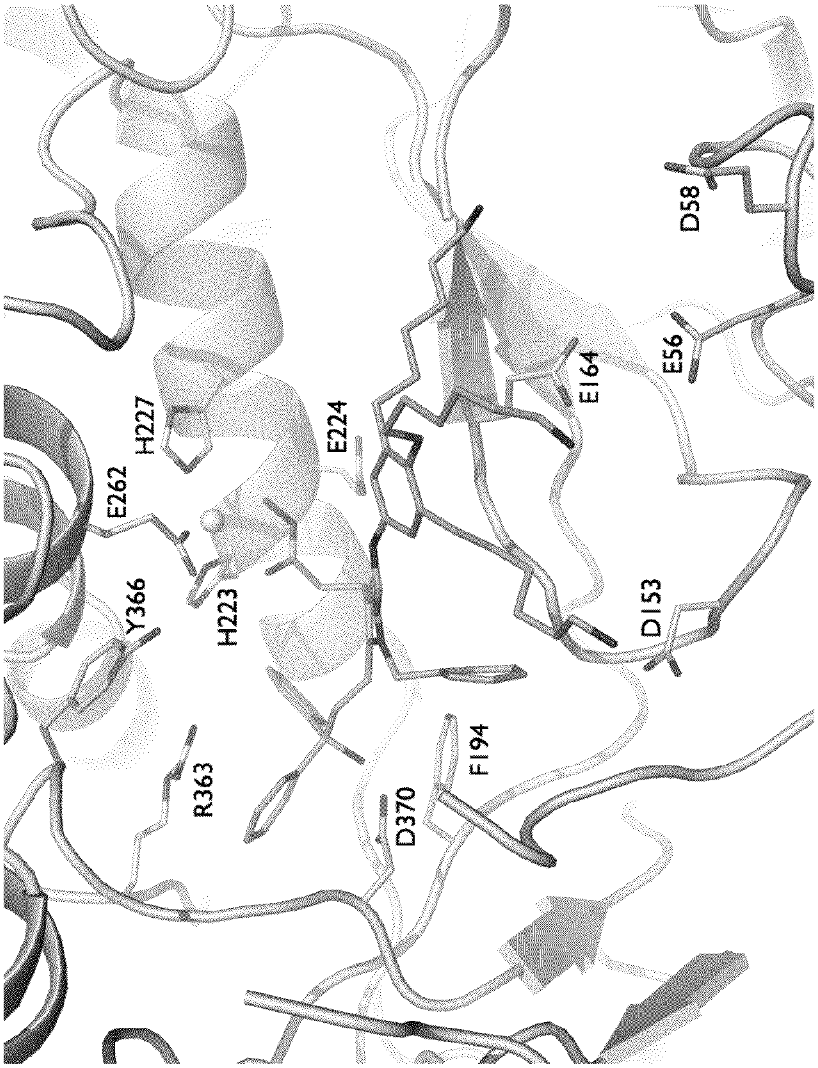
FIG. 10 shows a three-dimensional model of binding of E9 by BoNTAe.

As shown in FIG. 10, the hydroxamate group coordinates the zinc ion and has a hydrogen bond to E224, the diphenylmethyl group has cation-pi interactions with R363 and pi-pi interactions with Y366 and F194, the benzylic ammonium group has an ionic interaction with D370 and a cation-pi interaction with F194, N-substituted benzyl group has a pi-pi interaction with F194, the three alkylamino groups have ionic interactions with E164, E56, D153 and D58, indicating that E9 has a nanomolar affinity for BoNTAe.

Model of E10•BoNTAe

Figure 11:
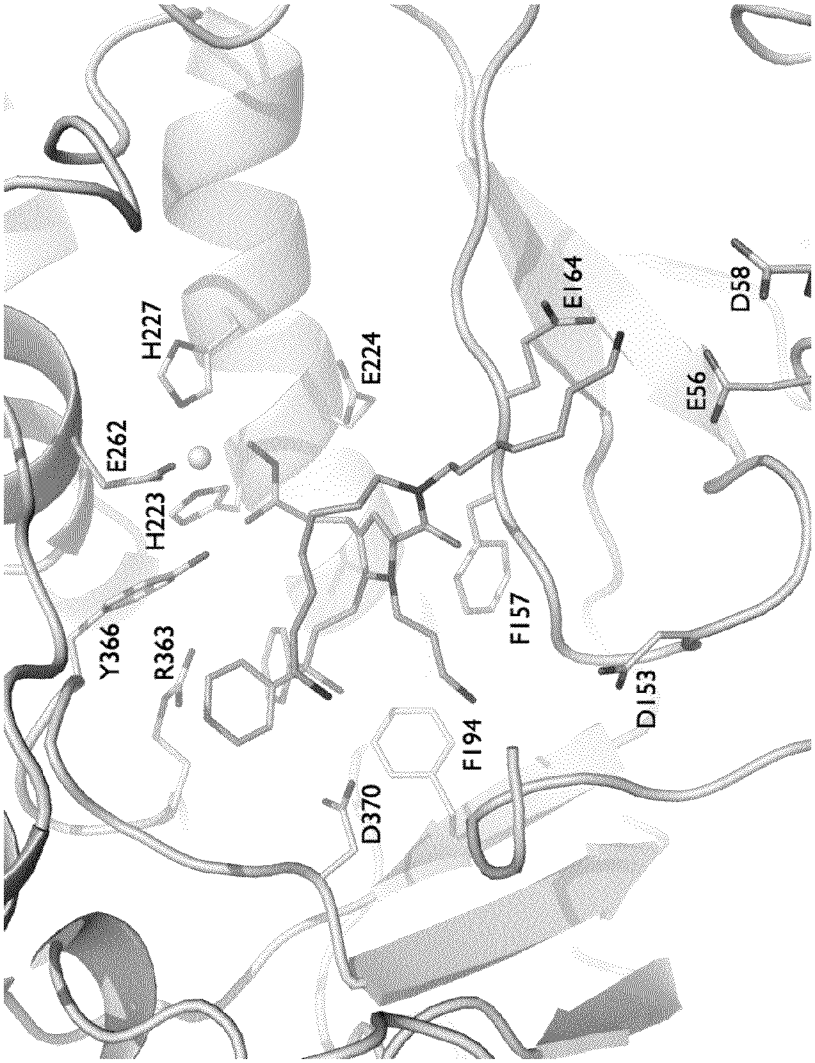
FIG. 11 shows a three-dimensional model of binding of E10 by BoNTAe.

As shown in FIG. 11, the hydroxamate group coordinates the zinc ion and has a hydrogen bond to E224, the diphenylmethyl group has cation-pi interactions with R363 and pi-pi interactions with Y366 and F194, the benzylic ammonium group has an ionic interaction with D370 and a cation-pi interaction with F194, the ammonium group attached to the pyrrole ring has ionic interactions with D370 and D153 and cation-pi interactions with F 194 and F157, one alkylamino group has an ionic interaction with D370, and the other alkylamino group has ionic interactions with E164, E56 and D58, indicating that E10 has a nanomolar affinity for BoNTAe.

Example 10

In Vitro Testing of E4, E6, E2, and E3

Relative Potency in Inhibiting BoNTAe

| Inhibitor | % inhibition of BoNTAe | Inhibitor concentration | $K_i$ |
|---|---|---|---|
| E4b | 79 ± 1 | 1 μM | 210 nM |
| E1e | 49 ± 0 | 1 μM | 360 nM |

-continued

Figure 12:
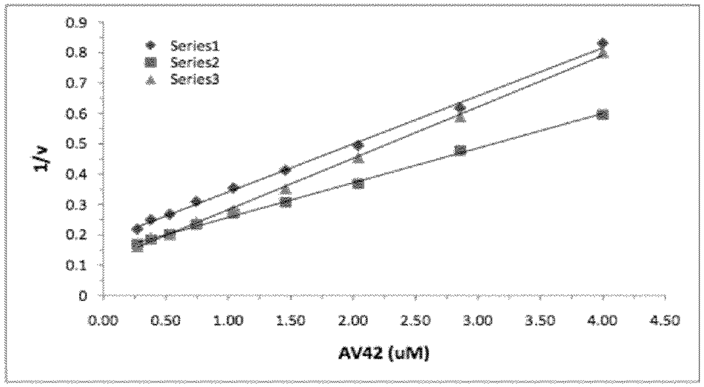
FIG. 12 is a Dixon plot illustrating the inhibition of BoNTAe by E4.

| Relative Potency in Inhibiting BoNTAe | | | |
|---|---|---|---|
| Inhibitor | % inhibition of BoNTAe | Inhibitor concentration | $K_i$ |
| E1d | 68 ± 1 | 1 μM | 340 nM |
| E1c | 75 ± 1 | 1 μM | 260 nM |
| E1h | 60 ± 1 | 1 μM | — |
| E1b | 48 ± 1 | 1 μM | — |
| E6b | 59 ± 2 | 1 μM | — |
| E6c | 55 ± 2 | 1 μM | — |
| E6g | 52 ± 1 | 1 μM | — |
| E4 (AV42 in FIG. 12) | 52 ± 1 | 1 μM | 760 nM |
| E6 | 50 ± 2 | 1 μM | — |
| E1g | 48 ± 0 | 1 μM | — |
| E1f | 47 ± 1 | 1 μM | — |
| E2 | 82 ± 6 | 20 μM | — |
| E3 | 47 ± 1 | 20 μM | — |

$K_i$ values were calculated from Dixon plots, using 7-9 concentrations of inhibitor. All inhibition assays were done in triplicate.

As an example, inhibition of BoNTAe by E4 was determined in three independent experiments using nine concentrations of E4 in each. $K_i$ was calculated from slopes of Dixon plots (FIG. 12) with the equation $K_i=K_m/[(\text{slope})(V_{max})(S)]$, where (S) was the substrate concentration (Segel I H (1975) Enzyme Kinetics. New York: Wiley and Sons. 170-178 p.). Kinetic constants for the substrate were taken from Schmidt J J, Stafford R G (2003) *Appl Environ Microbiol* 69: 297-303. The $K_i$ values obtained by using two other methods agreed well with the value obtained from the Dixon plots.

Example 11

In Vivo Testing of E2 and E3

The in vivo pharmacokinetic parameters of E2 and E3 were determined by dosing 6 Balb/c mice intraperitoneally with E2 or E3 at a dose of 2 mg/kg. Blood was collected by cardiac puncture at 0.5, 1, 2, 4, 8, and 24 hours and the plasma was separated and kept frozen at −80° C. until processing. Each experiment was repeated three times with each compound. The plasma was thawed and extracted with two volumes of ice-cold acetonitrile to precipitate plasma proteins and release the compound. The organic phase was analyzed by LC/MS and the concentration of E2 and E3 was determined based on a standard curve run in parallel. The stability of E2 and E3 in acetonitrile was determined prior to analyzing pharmacokinetic samples. Pharmacokinetic values were determined with WinNonLin software from Pharcite based on the plasma concentration curve.

| | $T_{1/2}$ ($hrs^{-1}$) | $T_{max}$ (hrs) | $C_{max}$ (ng/mL) | $AUC_{last}$ (hrs * ng/mL) | $V_d$ (L/kg) |
|---|---|---|---|---|---|
| E2 | 6.5 | 0.5 | 738.4 | 1386.4 | 14.95 |
| E3 | 6.25 | 1.0 | 255.99 | 1385.93 | 12.84 |

The pharmacokinetic data suggest that the exposure of the mice to the compounds as measured by the area under the time-concentration curve (AUC) is similar even though the maximum concentration ($C_{max}$) for each compound is different. The data also indicates that the apparent volume of distribution is large for both E2 and E3 indicating that both compounds readily leave the vasculature and enter tissue. The half-life of E2 and E3 are approximately equal and both are significantly shorter than the half-life of intraneuronal BoNTAe. This observation suggests that these and other reversible inhibitors of BoNTA should be administered repeatedly to ensure sufficient compound concentration is maintained to inhibit the enzymatic activity of BoNTAe.

Figure 13:
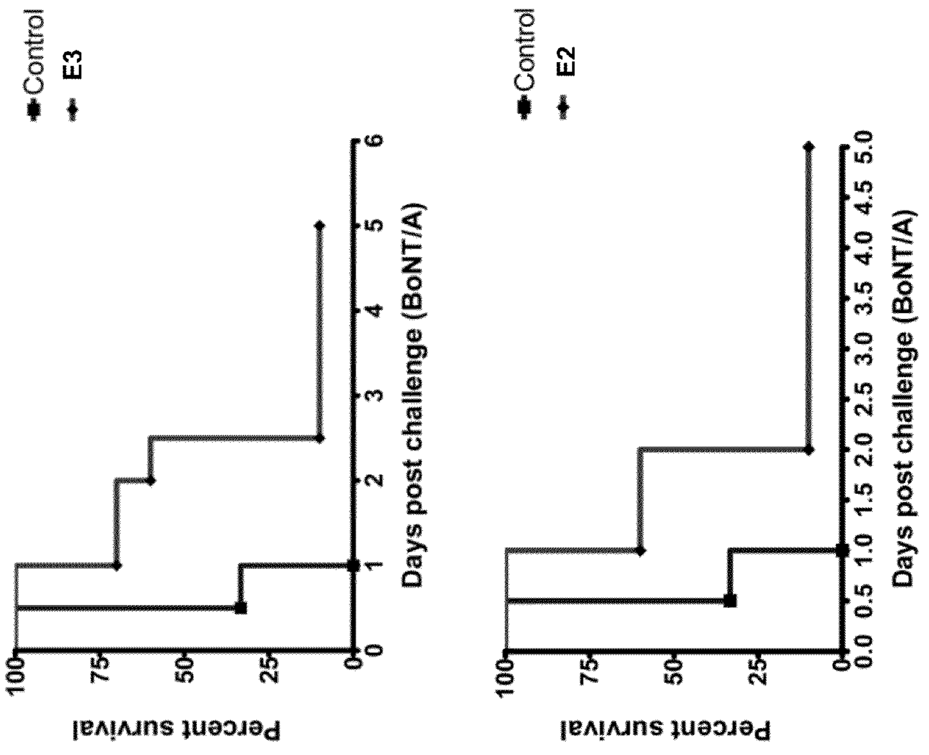
FIG. 13 details the survival curves for mice injected with BoNTA and those injected with BoNTA and compound E2 or E3.

The efficacy of E2 and E3 were evaluated in a mouse model of botulism. In this model, groups of 10 Balb/c mice were given an intraperitoneal injection of either E2 or E3, and after 30 minutes each mouse was injected with 5 $LD_{50}$ of botulinum neurotoxin serotype A. Control mice did not receive either compound but did receive an equal volume injection of the carrier vehicle used to solubilize E2 and E3; these mice then received a 5 $LD_{50}$ injection of botulinum neurotoxin serotype A. All mice were monitored twice daily for survival and signs/symptoms consistent with botulism. Survival curves (FIG. 13) were constructed based on the number of survivors and statistically analyzed using GraphPad Prism 5.0 (Graphpad Software, Inc.). Both E2 and E3 significantly ($p<0.05$) increased the proportion of survivors.

Example 12

Synthesis of E4b

E4b was synthesized according to the scheme in FIG. 17.

2,2-Diphenylbut-3-yn-1-ol (10)

Into a cooled (−78° C.) and stirred solution of 2,2-diphenyloxirane (0.98 g, 5.00 mmol) in anhydrous THF (15 mL) under nitrogen was added freshly distilled boron trifluoride etherate (1.0 mL). After 10 minutes of stirring acetylenemagnesium bromide (0.5 M solution in THF, 15 mL, 7.5 mmol) was added. Stirring was continued for another 30 minutes before warming to room temperature. The reaction was quenched by adding a saturated solution of $NH_4Cl$ (10 mL). Layers were separated and the aqueous layer was extracted with EtOAc (2×10 mL). The organic layers were combined, washed with brine (10 mL), dried over $MgSO_4$, and concentrated in vacuo. The residue was purified by MPLC on silica gel (gradient from Hex to EtOAc) to give 0.721 g (65%) of a light yellow solid. mp 73-74° C.; $^1$H NMR (400 MHz, $CDCl_3$) δ 7.39-7.23 (m, 10H), 5.08 (ddd, J=7.0, 6.3, 2.1 Hz, 1H, CHH), 4.27 (d, J=7.0 Hz, 1H, CHH), 2.46 (d, J=2.1 Hz, 1H), and 1.95 (d, J=6.3 Hz, 1H); $^{13}$C NMR (100 MHz, $CDCl_3$) δ 140.75, 140.04, 129.14, 129.10, 128.85, 128.69, 127.37, 127.27, 83.60, 75.37, 65.26, and 57.77; IR (KBr) 3358, 3277, 3027, 1491, and 1450 $cm^{-1}$; LRMS-El m/z 222 ([$M^+$], 2%), 167 ([$Ph_2CH_3^+$], 100%).

Benzyl 1-benzyl-4-formyl-5-(4-hydroxy-3,3-diphenylbut-1-ynyl)-1H-pyrrole-2-carboxylate (5)

A 7 mL vial was charged with 4 (0.23 g, 0.54 mmol), 2,2-Diphenylbut-3-yn-1-ol (0.24 g, 1.08 mmol), CuI (21 mg, 0.11 mmol), $Pd(PPh_3)_2Cl_2$ (76 mg, 0.11 mmol), $PPh_3$ (28 mg, 0.11 mmol), DMF (2 mL, regular) and $Et_3N$ (2 mL, regular). The vial was tightly capped, then heated at 65° C. for 17 hours. The solution was then cooled to room temperature, diluted with water (5 mL), and extracted with EtOAc (3×5 mL). The organic layers were combined, washed with brine (5 mL), dried over $MgSO_4$, and then purified twice by MPLC on silica gel (gradient from Hex to EtOAc) to afford 0.20 g (65%) of brown viscous syrupy matter. $^1$H NMR (400 MHz, $CDCl_3$) δ 9.60 (s, 1H), 7.43-7.10 (m, 19H), 7.00 (m 2H), 5.38 (s, 2H), 5.37-5.33 (m, 1H) 5.20 (s, 2H), 4.32 (d, J=7.8 Hz, 1H), and 3.04-2.99 (m, 1H); $^{13}$C NMR (100 MHz, $CDCl_3$) δ 185.42, 159.89, 140.54, 140.06, 137.02, 135.70, 129.12, 128.96, 128.90, 128.87, 128.84, 128.74, 128.61, 128.29, 127.87, 127.56, 127.50, 127.14, 124.74, 117.02, 100.68, 77.56, 74.90, 66.66, 66.11, 57.86, and 50.22; IR (KBr) 3416, 3023, 1715, and 1675 $cm^{-1}$; LRMS-El m/z 539 ([$M^+$], 1%), 167 ([$Ph_2CH_3^+$], 74%), and 91 ([$PhCH_2^+$], 100%).

(E)-Benzyl 1-benzyl-4-(3-ethoxy-3-oxoprop-1-enyl)-5-(4-hydroxy-3,3-diphenylbut-1-ynyl)-1H-pyrrole-2-carboxylate (6)

A 7-mL vial was charged with 5 (0.20 g, 0.37 mmol), (ethoxycarbonylmethylene)triphenylphosphorane (0.20 g, 0.56 mol) and benzene (3 mL). The vial was capped and heated at 80° C. for 12 hours. The solvent was evaporated and the residue was purified by MPLC on silica gel (gradient from Hex to EtOAc) to afford 0.20 g (86%) of a light tan foam. $^1$H NMR (400 MHz, $CDCl_3$) δ 7.64 (d, J=16.0 Hz, 1H), 7.39-7.16 (m 19H), 6.96 (m, 2H), 6.31 (d, J=16.0 Hz, 1H), 5.36-5.33 (m, 3H), 5.20 (s, 2H), 4.33 (d, J=7.4 Hz, 1H), 4.26 (q, J=7.1H, 2H), 2.94 (d, J=5.7 Hz, 1H), and 1.33 (t, J=7.1 Hz, 3H); $^{13}$C NMR (100 MHz, $CDCl_3$) δ 167.77, 159.94, 140.76, 140.25, 137.71, 136.38, 135.98, 129.12, 129.00, 128.99, 128.88, 128.85, 128.81, 128.73, 128.54, 128.41, 128.33, 128.20, 127.60, 127.33, 127.02, 124.27, 124.22, 123.65, 116.77, 115.89, 100.57, 77.58, 76.17, 66.43, 66.13, 60.64, 57.81, 50.18, and 14.66; IR (KBr) 3444, 3027, 1703, and 1634 $cm^{-1}$; LRMS-El m/z 592 ([$M-H_2O^+$], 100%).

1-Benzyl-4-(3-ethoxy-3-oxopropyl)-5-(4-hydroxy-3,3-diphenylbutyl)-1H-pyrrole-2-carboxylic acid (7)

A 25-mL flask was charged with 6 (21 mg, 0.03 mmol), 20% $Pd(OH)_2$ on carbon (nominally 50% in water, 7 mg), and 1 mL each of EtOAc and MeOH. The suspension was stirred under a hydrogen balloon at room temperature for 5-17 hours. The catalyst was filtered off (Celite), the residue concentrated to give 20 mg (quantitative) of a pale yellow foam, which was used without further purification. $^1$H NMR (400 MHz, $CDCl_3$) δ 7.30-7.15 (m, 13H), 6.95 (s, 1H), 6.90 (m, 2H), 5.45 (ABq, J=16.4 Hz, 2H), 4.21 (td, J=8.5, 2.1 Hz, 1H), 4.09 (q, J=7.0H, 2H), 3.75 (d, J=8.6 Hz, 1H), 2.72-2.58 (m, 4H), 2.46 (t, J=7.4 Hz, 2H), 1.06-1.51 (m, 2H), 1.48-1.44 (m, 2H), and 1.22 (t, J=7.0 Hz, 3H); $^{13}$C NMR (100 MHz, $CDCl_3$) δ 173.45, 165.67, 142.18, 141.36, 139.65, 138.95, 129.11, 128.99, 128.88, 128.72, 128.30, 127.20, 127.15, 126.94, 126.01, 120.86, 120.09, 119.67, 73.09, 60.66, 58.67, 48.23, 35.37, 34.81, 21.23, 20.70, and 14.50; IR (KBr) 3428, 3027, 2933, 1732, 1663, and 1450 $cm^{-1}$; LRMS-El m/z 481 ([$M-CO_2^+$], 64%), 167 ([$Ph_2CH_3^+$], 75%), and 91 ([$PhCH_2^+$], 100%).

Ethyl 3-(1-benzyl-5-(bis(7-(1,3-dioxoisoindolin-2-yl)heptyl)carbamoyl)-2-(4-hydroxy-3,3-diphenylbutyl)-1H-pyrrol-3-yl)propanoate (8)

The compound 7 (20 mg, 0.04 mmol) was charged into a 7-mL vial, followed by 2,2'-(7,7'-azanediylbis(heptane-7,1-diyl))diisoindoline-1,3-dione (38 mg, 0.12 mmol), BOP (50 mg, 0.12 mmol) and 1 mL each of NMM and dry DMF. The vial was capped and stirred at room temperature for 19 hours. Water (3 mL) was added into the reaction mixture, extracted with EtOAc (3×5 mL), the organic layers were combined, washed with brine (5 mL), dried over $MgSO_4$, and purified by MPLC (silica gel, gradient from Hex to EtOAc) to give 24 mg (63%) of a tan solid foam. $^1$H NMR (400 MHz, $CDCl_3$) δ 7.84-7.82 (m, 4H), 7.71-7.69 (m, 4H), 7.39-7.12 (m, 13H), 6.74-6.72 (m, 2H), 6.14 (s, 1H), 5.06 (ABq, J=16.6 Hz, 2H), 4.33 (br t, 1H), 4.06 (q, J=7.0H, 2H), 3.83 (d, J=8.6 Hz, 1H), 3.65 (t, J=7.2 Hz, 4H), 3.18 (m, 4H), 2.79-2.69 (m, 2H), 2.65 (t, J=8.4 Hz, 2H), 2.41 (t, J=7.5 Hz, 2H), 1.65-1.53 (m, 6H), 1.27-1.21 (m, 12H), and 1.22 (t, J=7.1 Hz, 3H), and 1.19 (m, 4H); $^{13}$C NMR (100 MHz, $CDCl_3$) δ 173.79, 168.75, 165.70, 142.15, 141.42, 139.16, 134.71, 134.16, 132.31, 129.07, 128.96, 128.87, 128.62, 128.30, 127.33, 127.14, 126.89, 126.28, 123.55, 123.43, 118.52, 112.44, 73.42, 60.68, 58.59, 47.78, 38.16, 35.93, 35.32, 29.08, 28.70, 26.92, 26.85, 21.40, 20.46, and 14.44; IR (KBr) 3460, 2929, 2856, and 1716; LRMS-El m/z 1011 ([$M^+$]).

N,N-Bis(7-aminoheptyl)-1-benzyl-5-(4-hydroxy-3,3-diphenylbutyl)-4-(3-(hydroxyamino)-3-oxopropyl)-1H-pyrrole-2-carboxamide (E4b)•$(TFA)_2$ A 20-mL scintillation vial was charged with 8 (51 mg, 0.05 mmol), 50% hydroxylamine in water (2 mL), KCN (16 mg, 0.25 mmol), and 2 mL each of MeOH and THF. The vial was capped, heated at 65° C. for 48 hours. The resulting mixture was directly used for HPLC purification on a reversed-phase column to afford 13 mg (27%) of the title compound as a colorless oily residue. Preparative HPLC conditions: Phenomenex Gemini C18, 21.2×250 mm, linear gradient from 20% solvent B and 80% solvent A to 100% solvent B over 40 minutes, solvent A=water (0.1% TFA), solvent B=9:1 mixture of MeCN/water (0.1% TFA), flow rate 10 mL/min, collected portion at $R_T$=18.56 minutes. Analytical HPLC condition: Phenomenex HyperClone BDS C18 column, 4.6×250 mm, linear gradient from 20% B to 100% B over 20 min, same solvent system as the preparative, $R_T$=12.18 minutes. $^1$H NMR (400 MHz, $CD_3OD$) δ 7.37-7.35 (m, 2H), 7.26-7.12 (m, 10H), 7.39-7.12 (m, 13H), 6.75-6.74 (m, 2H), 6.18 (s, 1H), 5.05 (ABq, J=16.6 Hz, 2H), 4.40 (t, J=8.2 Hz, 1H), 3.85 (d, J=9.4 Hz, 1H), 3.25 (t, J=7.2 Hz, 4H), 2.89 (t, J=7.5 Hz, 4H), 2.85-2.63 (m, 4H), 2.20-2.18 (m, 2H), 1.63-1.49 (m, 6H), 1.40-1.31 (m, 12H), and 1.20-1.10 (m, 4H); $^{13}$C NMR (100 MHz, $CD_3OD$) δ 231.42, 171.17, 165.58, 143.32, 142.97, 139.36, 134.21, 128.51, 128.35, 128.16, 126.98, 126.30, 126.08, 125.99, 124.53, 118.05, 111.85, 72.62, 58.54, 39.52, 36.33, 34.34, 28.57, 27.23, 26.23, 26.04, 21.52, and 19.93; IR (KBr) 3424, 2933, 2864, 1679, and 1205; LRMS-El m/z 738 ([$M^+$]).

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a compound of Formula (IIA):

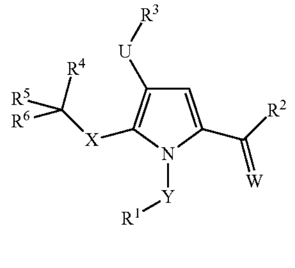

or a pharmaceutically acceptable salt or derivative thereof, wherein:

$R^1$ is chosen from $NH_2$, aryl, and heteroaryl;

$R^2$ is chosen from $NR^{2a}R^{2b}$;

$R^{2a}$ and $R^{2b}$ are chosen from $(CH_2)_mNH_2$;

m is an integer from 4 to 12;

$R^3$ is chosen from thiol, imidazole, sulfonamide, COOH, and CONHOH;

$R^4$ and $R^5$ are independently chosen from aryl and heteroaryl;

$R^6$ is chosen from H, OH, $CH_2OH$, $NH_2$, aryl and heteroaryl;

U and X are independently $(CH_2)_{m1}V(CH_2)_{m2}$;

V is chosen from C, C(OH), 0, S, and NH, or is absent;

m1 is an integer from 0 to 2;

m2 is an integer from 0 to 2;

W is chosen from 0 and S, or is absent;

Y is chosen from $CO(CH_2)_{m3}$, $(CH_2)_{m3}$, and $CONH(CH_2)_{m3}$;

m3 is an integer from 1 to 10; and all non-hydrogen atoms in the pyrrole ring can be substituted by N, S, or O provided the substitution maintain aromaticity.

2. The composition of claim 1, wherein the compound of Formula (II-A) is chosen from:

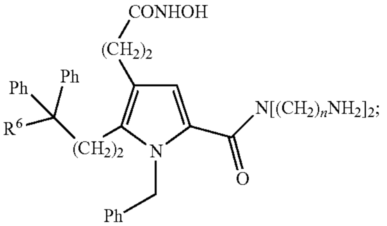

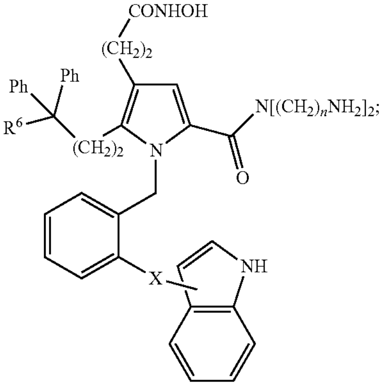

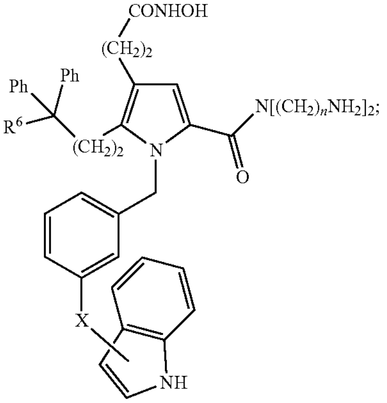

-continued

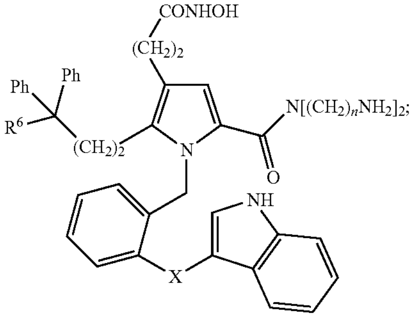

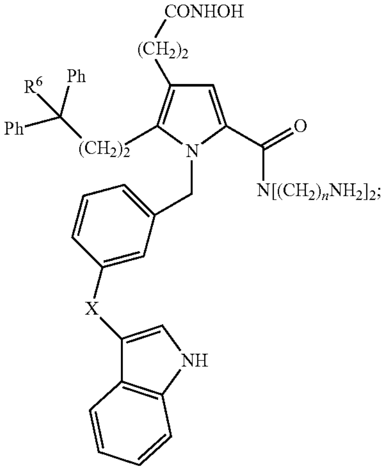

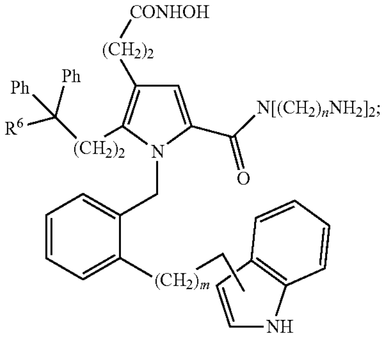

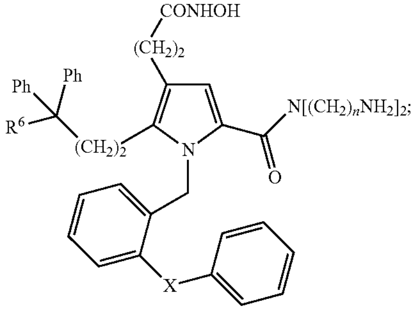

and

-continued

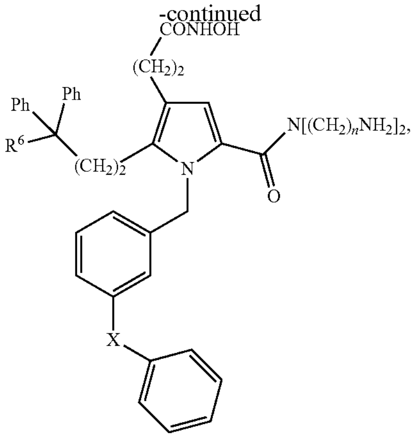

or a pharmaceutically acceptable salt or derivative thereof, wherein:

$R^6$ is chosen from H, OH, $CH_2OH$, and $NH_2$;

m is an integer from 3 to 10;

n is an integer from 5 to 10;

X is chosen from $(CH_2)_{m1}V^1(CH_2)_{m2}V^2(CH_2)_{m3}$;

$V^1$ and $V^2$ are independently chosen from C, C(OH), O, S, and NH, or are absent;

m1 is an integer from 0 to 4;

m2 is an integer from 0 to 4; and m3 is an integer from 0 to 4.

3. The composition of claim 1, wherein the compound of Formula (II-A) is chosen from:

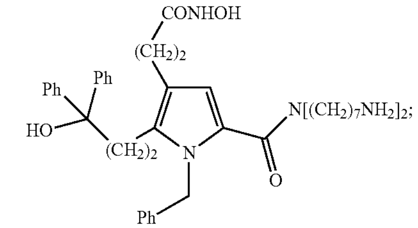

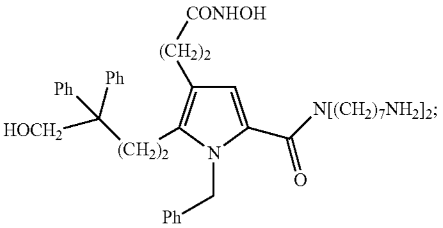

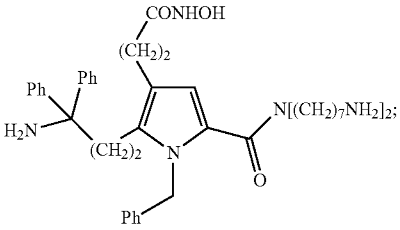

-continued

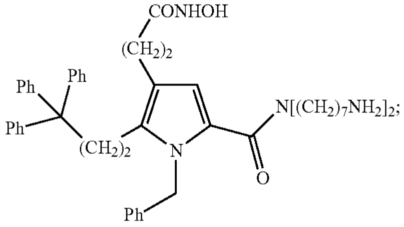

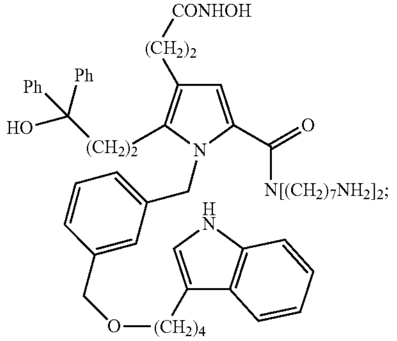

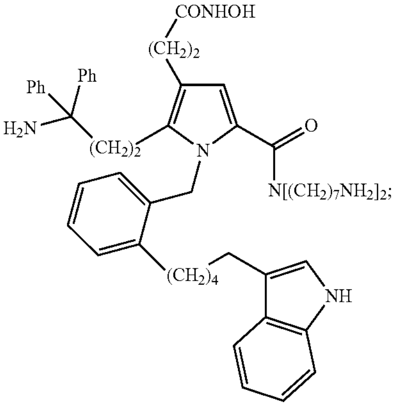

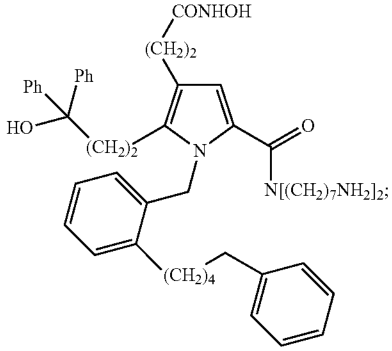

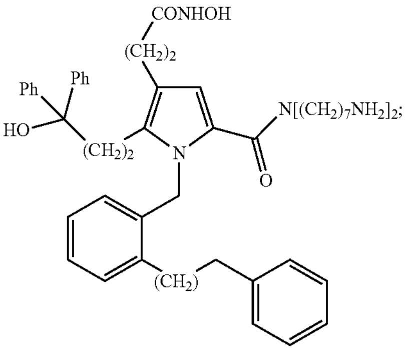

-continued

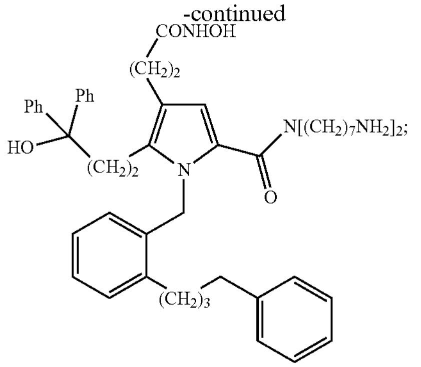

and

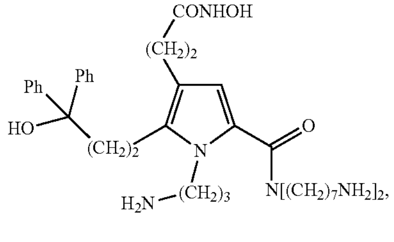

or a pharmaceutically acceptable salt or derivative thereof.

4. A kit comprising a composition according to claim 1.

5. The kit of claim 4, wherein the composition is in the form of an injectable composition.

6. A pharmaceutical composition comprising a composition of claim 1 and a pharmaceutically acceptable carrier, excipient, or adjuvant.

7. The compound of claim 1, wherein the compound of Formula (IIA) is:

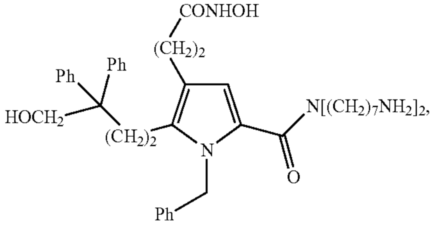

or a pharmaceutically acceptable salt thereof.

8. The compound of claim 1, wherein:

$R^1$ is phenyl;
$R^2$ is $N[(CH_2)_7NH_2]_2$;
$R^4$ is phenyl;
$R^5$ is phenyl;
$R^6$ is $CH_2OH$;
X is $(CH_2)_2$;
Y is $(CH_2)_2$;
W is O; and
U is $(CH_2)_2$,
or a pharmaceutically acceptable salt thereof.

9. The compound of claim 8, wherein $R^3$ is COOH.

10. The compound of claim 1, wherein:

$R^1$ is phenyl;
$R^2$ is $N[(CH_2)_7NH_2]_2$;
$R^3$ is COOH;
$R^4$ is phenyl;
$R^5$ is phenyl;
$R^6$ is $CH_2OH$;
X is $(CH_2)_2$;
Y is $(CH_2)_2$;
W is O; and
U is $(CH_2)_2$,
or a pharmaceutically acceptable salt thereof.

11. The kit of claim 4, wherein the compound of Formula (IIA) is:

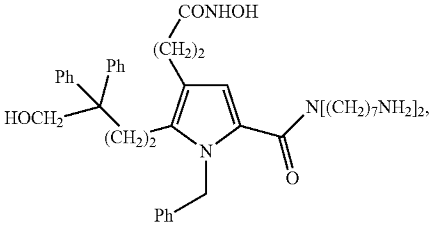

or a pharmaceutically acceptable salt thereof.

12. The kit of claim 4, wherein:

$R^1$ is phenyl;
$R^2$ is $N[(CH_2)_7NH_2]_2$;
$R^4$ is phenyl;
$R^5$ is phenyl;
$R^6$ is $CH_2OH$;
X is $(CH_2)_2$;
Y is $(CH_2)_2$;
W is O; and
U is $(CH_2)_2$,
or a pharmaceutically acceptable salt thereof.

13. The kit of claim 12, wherein $R^3$ is COOH.

14. The kit of claim 4, wherein:

$R^1$ is phenyl;
$R^2$ is $N[(CH_2)_7NH_2]_2$;
$R^3$ is COOH;
$R^4$ is phenyl;
$R^5$ is phenyl;
$R^6$ is $CH_2OH$;
X is $(CH_2)_2$;
Y is $(CH_2)_2$;
W is O; and
U is $(CH_2)_2$,
or a pharmaceutically acceptable salt thereof.

15. The pharmaceutical composition of claim 6, wherein the compound of Formula (IIA) is:

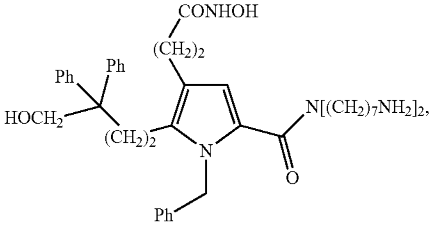

or a pharmaceutically acceptable salt thereof.

16. The pharmaceutical composition of claim 6, wherein:

$R^1$ is phenyl;
$R^2$ is $N[(CH_2)_7NH_2]_2$;
$R^4$ is phenyl;
$R^5$ is phenyl;
$R^6$ is $CH_2OH$;
X is $(CH_2)_2$;
Y is $(CH_2)_2$;
W is O; and
U is $(CH_2)_2$,
or a pharmaceutically acceptable salt thereof.

17. The pharmaceutical composition of claim 16, wherein $R^3$ is COOH.

18. The pharmaceutical composition of claim 6, wherein:

$R^1$ is phenyl;

$R^2$ is $N[(CH_2)_7NH_2]_2$;

$R^3$ is COOH;

$R^4$ is phenyl;

$R^5$ is phenyl;

$R^6$ is $CH_2OH$;

X is $(CH_2)_2$;

Y is $(CH_2)_2$;

W is O; and

U is $(CH_2)_2$, or a pharmaceutically acceptable salt thereof.

* * * * *

UNITED STATES PATENT AND TRADEMARK OFFICE

CERTIFICATE OF CORRECTION

PATENT NO. : 8,404,728 B2
APPLICATION NO. : 12/846187
DATED : March 26, 2013
INVENTOR(S) : Yuan-Ping Pang et al.

It is certified that error appears in the above-identified patent and that said Letters Patent is hereby corrected as shown below:

Title Page, item 73 (Assignees), delete "Material" and insert -- Materiel --, therefor;

Title Page, item 73 (Assignees), delete "Washington, DC" and insert -- Frederick, MD --, therefor;

In the Claims

Column 79, line 12 (Claim 1), delete "0" and insert -- O --, therefor;

Column 79, line 16 (Claim 1), delete "0" and insert -- O --, therefor.

Signed and Sealed this
Twenty-fourth Day of June, 2014

Michelle K. Lee
*Deputy Director of the United States Patent and Trademark Office*